(12) United States Patent
Yamamoto et al.

(10) Patent No.: US 7,517,996 B2
(45) Date of Patent: Apr. 14, 2009

(54) AZOLE COMPOUND

(75) Inventors: Takashi Yamamoto, Kawasaki (JP); Akira Chiba, Kawasaki (JP); Koichi Fujita, Kawasaki (JP); Yuka Kataba, Kawasaki (JP); Koji Ohsumi, Kawasaki (JP); Sayaka Asari, Kawasaki (JP); Naoyuki Fukuchi, Kawasaki (JP); Misato Noguchi, Kawasaki (JP); Itsuya Tanabe, Kawasaki (JP); Chiori Ijichi, Kawasaki (JP); Naoko Oomuta, Kawasaki (JP); Yuko Iida, Kawasaki (JP); Satoshi Iwayama, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/346,426

(22) Filed: Feb. 3, 2006

(65) Prior Publication Data

US 2006/0194850 A1    Aug. 31, 2006

Related U.S. Application Data

(63) Continuation of application No. PCT/JP2004/011565, filed on Aug. 5, 2004.

(30) Foreign Application Priority Data

| Aug. 5, 2003 | (JP) | ............................. 2003-287234 |
| Feb. 10, 2004 | (JP) | ............................. 2004-034300 |
| Jul. 2, 2004 | (JP) | ............................. 2004-197389 |

(51) Int. Cl.
C07D 261/04 (2006.01)
A01N 43/80 (2006.01)

(52) U.S. Cl. ........................ 548/245; 514/380

(58) Field of Classification Search .................. None
See application file for complete search history.

(56) References Cited

U.S. PATENT DOCUMENTS

| 4,502,881 | A | 3/1985 | Francese et al. |
| 6,964,975 | B2 | 11/2005 | Ueno et al. |
| 7,012,075 | B2 | 3/2006 | Prasit et al. |
| 2003/0114505 | A1 | 6/2003 | Ueno et al. |
| 2004/0067908 | A1 | 4/2004 | Nakade et al. |
| 2004/0171582 | A1 | 9/2004 | Nakade et al. |
| 2005/0197328 | A1 | 9/2005 | Bailey et al. |

FOREIGN PATENT DOCUMENTS

| CH | 68/779 | 7/1967 |
| EP | 0 120 821 | 10/1984 |
| GB | 1 210 602 | 10/1970 |
| JP | 7-149748 | 6/1995 |
| WO | 98/28282 | 7/1998 |
| WO | 01/60819 | * 8/2001 |
| WO | 02/40458 | 5/2002 |
| WO | 02/062389 | 8/2002 |
| WO | 02/069901 | 9/2002 |
| WO | 03/007991 | 1/2003 |
| WO | 03/013605 | 2/2003 |
| WO | 03/080610 | 10/2003 |

OTHER PUBLICATIONS

Prasit et al., "Preparation of N-cyanomethyl amides as cathepsin cystein protease inhibitors", CAPLUS AN 2002:695723, Published Sep. 12, 2002.*
http://www.nlm.nih.gov/ mdelineplus/liverdiseases.html.*
http://www.cancer.gov/cancertopics/wyntk/liver/page10.*
Zips et al., "In vitro and in vivo evaluation of new anticancer agents", in vivo, 19 (2005), 1-7 (8 pages).*
http://www.livercancertreatment.org/treatment/resection-ablation.asp.*
http://www.livercancertreatment.org/diagnosing/prevention.asp.*
http://www.itmonline.org/arts/fibrosis.htm.*
Bataller et al., "Liver fibrosis", the journal of clinical invenstigation, vol. 115, Feb. 2005, p. 209-218.*
L. L. Gumanov et al, "Thermal decomposition of benzotrifuroxan", *Izvestiya Akademil Nauk SSSR, Seriya Khimicheskaya*, 1991, No. 8, pp. 1914-1915.
I. V. Ovchinnikov et al, "The Curtius Rearrangement of Azidocarbonylfuroxans: Some Peculiarities and the Synthesis of Aminofuroxans", *Mendeleev Communications*, 1995, No. 2, pp. 58-60.
Y. C. Kong et al, "Exploratory Chemistry of 3-Aroylformamido-4-aryl-1,2,5-thiadiazoles", *Journal of Heterocyclic Chemistry*, 1999, vol. 36, No. 2, pp. 515-523.
M. Yanase et al, "Lysophosphatidic Acid Enhances Collagen Gel Contraction by Hepatic Stellate Cells: Association with Rho-Kinase", *Biochemical and Biophysical Research Communications*, 2000, vol. 277, pp. 72-78.
D. C. Rockey, "Hepatic Blood Flow Regulation by Stellate Cells in Normal and Injured Liver", *Seminars in Liver Disease*, 2001, vol. 21, No. 3, pp. 337-349.

(Continued)

*Primary Examiner*—Kamak A. Saeed
*Assistant Examiner*—Sun Jae Y Loewe
(74) *Attorney, Agent, or Firm*—Oblon, Spivak, McClelland, Maier & Neustadt, P.C.

(57) ABSTRACT

Azole compounds represented by formula I:

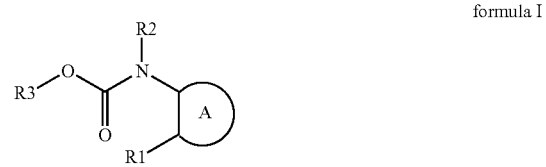

formula I wherein ring A is isoxazole and the like, R1 is a substituted or unsubstituted aryl group and the like, R2 is a hydrogen atom and the like, and R3 is a substituted or unsubstituted alkyl group and the like, and pharmaceutically acceptable salts thereof inhibit the physiological activity of lysophosphatidic acid (LPA), and are useful as for the prophylaxis or treatment of diseases in which inhibition of the physiological activity of LPA is useful for the prophylaxis or treatment thereof, such as diseases involving the LPA receptor.

4 Claims, No Drawings

OTHER PUBLICATIONS

H. Reynaert et al, "Hepatic stellate cells: role in microcirculation and pathophysiology of portal hypertension", *Gut*, 2002, vol. 50, pp. 571-581.

P. Tangkijvanich et al, "Rho and p38 MAP Kinase Signaling Pathways Mediate LPA-Stimulated Hepatic Myofibroblast Migration", *Journal of Biomedical Science*, 2003, vol. 10, pp. 352-358.

A. Tokumura et al, "Contractile actions of lysophosphatidic acids with a chemically-defined fatty acyl group on longitudinal muscle from guinea-pig ileum", *Journal of Pharmacy and Pharmacology*, 1982, vol. 34, pp. 514-516.

M. Mori et al, "Activation of Rho signaling contributes' to lysophosphatidic acid-induced contraction of intact ileal smooth muscle of guinea-pig", *Canadian Journal of Physiology and Pharmacology*, 2000, vol. 78, pp. 729-736.

B. P. Kropp et al, "Characterization of Cultured Bladder Smooth Muscle Cells: Assessment of In Vitro Contractility", *The Journal of Urology*, 1999, vol. 162, pp. 1779-1784.

C. Guo et al, "Mitogenic Signaling in Androgen Sensitive and Insensitive Prostate Cancer Cell Line", *The Journal of Urology*, 2000, vol. 163, pp. 1027-1032.

A. Tokumura et al, "Lysophosphatidic acids induce proliferation of cultured vascular smooth muscle cells from rat aorta", *The American Journal of Physiology*, 1994, vol. 267, pp. C204-C210.

S. Seewald et al, "Lysophosphatidic acid and intracellular signaling in vascular smooth muscle cells", *Atherosclerosis*, 1997, vol. 130, pp. 121-131.

C. N. Inoue et al, "Lysophospatidic acid and mesangial cells: implications for renal diseases", *Clinical Science*, 1999, vol. 96, pp. 431-436.

F. Imamura et al, "Induction of In Vitro Tumor Cell Invasion of Cellular Monolayers By Lysophosphatidic Acid or Phospholipase D", *Biochemical and Biophysical Research Communications*, 1993, vol. 193, No. 2, pp. 497-503.

H. Ikeda et al, "Effects of Lysophosphatidic Acid on Proliferation of Stellate Cells and Hepatocytes in Culture", *Biochemical and Biophysical Research Communications*, 1998, vol. 248, pp. 436-440.

F. Pietruck et al, "Signalling properties of lysophosphatidic acid in primary human skin fibroblasts: role of pertussis toxin-sensitive GTP-binding proteins", *Naunyn-Schmiedeberg's Archives of Pharmacology*, 1997, vol. 355, pp. 1-7.

D. Zhou et al, "Phosphatidic Acid and Lysophosphatidic Acid Induce Haptotactic Migration of Human Monocytes", *The Journal of Biological Chemistry*, 1995, vol. 270, No. 43, pp. 25549-25556.

M. H. Gräler et al, "Lysophospholipids and their G protein-coupled receptors in inflammation and immunity", *Biochimica et Biophysica Acta*, 2002, vol. 1582, pp. 168-174.

F. W. Holtsberg et al, "Lysophosphatidic Acid Induces Necrosis and Apoptosis in Hippocampal Neurons", *Journal of Neurochemistry*, 1998, vol. 70, No. 1, pp. 66-76.

E. D. Weiler et al, "Isothiazoles X. 3-Alkoxyisothiazole Derivatives", *Journal of Heterocyclic Chemistry*, 1977, vol. 14, pp. 725-728.

R. Calvino et al, "An Analysis of the Lipophilicity of Furazan and Furoxan Derivatives using the CLOGP Algorithm", *Journal of the Chemical Society, Perkin Transactions 2*, 1992, pp. 1643-1646.

A. Gasco et al, "Alkyl N-Methylfuroxanylcarbamates. Synthesis and Structure. II", *Journal of Heterocyclic Chemistry*, 1972, vol. 9, pp. 837-841.

A. Gasco et al, "Furazans and Furazan Oxides. Part IV.[1,2] The Structures and Tautomerism of Some Unsymmetrically Substituted Furoxans", *Journal of the Chemical Society, Perkins Transactions 2*, 1973, pp. 1613-1617.

D.L. Pain et al, "Congeners of Pyridine-4-carboxyhydrazide. Part II. Derivatives of 1,2,3-Thiadiazole", *Journal of the Chemical Society*, 1965, pp. 5166-5177.

K. Masuda et al, "Studies on Mesoionic Compounds. XII.[1)] Synthesis of 1,2,3-Thiadiazolium-4-aminide Derivatives and Their Characterization", *Chemical and Pharmaceutical Bulletin*, 1981, vol. 29, No. 6, pp. 1743-1747.

A. Tokumura, "Lysophosphatidic Acids Induce Contraction of Rat Isolated Colon by Two Different Mechanisms", *Journal of Pharmacy and Pharmacology*, 1991, vol. 43, pp. 774-778.

T. L. Ediger et al, "Synergistic Stimulation of Airway Smooth Muscle Cell Mitogenesis", *The Journal of Pharmacology and Experimental Therapeutics*, 2000, vol. 294, No. 3, pp. 1076-1082.

N. R. Smalheiser, "Acute Neurite Retraction Elicited by Diverse Agents is Prevented by Genistein, a Tyrosine Kinase Inhibitor", *Journal of Neurochemistry*, 1993, vol. 61, pp. 340-343.

\* cited by examiner

AZOLE COMPOUND

CROSS REFERENCES TO RELATED APPLICATIONS

This application is a continuation of International Patent Application No. PCT/JP2004/011565, filed on Aug. 5, 2004, and claims priority to Japanese Patent Application No. 2003-287234, filed on Aug. 5, 2003, Japanese Patent Application No. 2004-034300, filed on Feb. 2, 2004, and Japanese Patent Application No. 2004-197389, filed on Jul. 2, 2004, all of which are incorporated herein by reference in their entireties.

BACKGROUND OF THE INVENTION

1. Field of the Invention

The present invention relates to novel azole compounds, salts thereof, and uses of such an azole compound as a pharmaceutical product. The compounds of the present invention inhibit the physiological activity of lysophosphatidic acid (LPA), and therefore, are useful as agents for the prophylaxis or treatment of diseases in which inhibition of the physiological activity of LPA is useful for the prophylaxis or treatment thereof, such as diseases in which LDA receptor participates. More specifically, the compounds are useful as agents for the prophylaxis or treatment of fibrosis of organs (liver, kidney, lung, and the like), liver diseases (acute or chronic hepatitis, liver fibrosis, liver cirrhosis, portal hypertension, regenerative failure, non-alcoholic steatohepatitis (NASH), liver hypofunction, hepatic blood flow disorder, and the like), cell proliferative disease (cancer (solid tumor, solid tumor metastasis, vascular fibroma, myeloma, multiple myeloma, Kaposi's sarcoma, leukemia, and the like) and invasive metastasis of cancer cell, and the like), inflammatory disease (psoriasis, nephropathy, pneumonia and the like), gastrointestinal tract disease (irritable bowel syndrome (IBS), inflammatory bowel disease (IBD), abnormal pancreatic secretion, and the like), renal disease, urinary tract-associated disease (benign prostatic hyperplasia or symptoms associated with neuropathic bladder disease, spinal cord tumor, hernia of intervertebral disk, spinal canal stenosis, symptoms derived from diabetes, lower urinary tract disease (obstruction of lower urinary tract, and the like), inflammatory disease of lower urinary tract, dysuria, frequent urination, and the like), pancreas disease, abnormal angiogenesis-associated disease (arterial obstruction and the like), brain-associated disease (cerebral infarction, cerebral hemorrhage, and the like), peripheral neuropathy, and the like. Particularly, the present compounds are useful as agents for the prophylaxis or treatment of fibrosis of organs (liver, kidney, lung, and the like) or liver diseases.

2. Discussion of the Background

Lysophosphatidic acid (LPA) exists in a trace amount in living organisms, and is a lysophospholipid that shows various physiological activities. LPA is produced and released from various cells stimulated by a physiologically active substance (*The Journal of Biological Chemistry*, (US), 1995, vol. 270, pp. 12949-12952 and *The Journal of Biological Chemistry*, (US), 1992, vol. 267, pp. 10988-10993). Since it is present in a small amount in plasma and in an abundant amount in serum in living organisms, the major site (cell) of production is considered to be platelets (*The Biochemical Journal*, (UK), 1993, vol. 291, pp. 677-680). Thus, LPA concentration is considered to increase in the topical site of inflammation or hemorrhage. In fact, it has been reported that LPA concentration increases in human arteriosclerosis lesion and in brain spinal fluid in intracerebral hemorrhage model (*Proceedings of the National Academy of Sciences USA*, (US), 1999, vol. 96, pp. 6931-6936 and *Journal of Neurochemistry*, (UK), 1996, vol. 67, pp. 2300-2305). Moreover, activation of platelets has been reported in acute or chronic hepatitis patients (*The Tokai Journal of Experimental and Clinical Medicine*, (JP), 2002, vol. 27, pp. 101-106, *Hepato-Gastroenterology*, (GK), 2001, vol. 48, pp. 818-822, and *Journal of Investigative Medicine*, (US), 2001, vol. 49, pp. 407-412), and an increase in the LPA concentration at a blood or liver topical site is suggested in both acute and chronic hepatitis patients. In addition, there is a report on an increased LPA concentration in ascites of intraperitoneal disseminated ovarian cancer patients and in the blood of multiple myeloma patients (*Gynecologic Oncology*, (US), 1998, vol. 71, pp. 364-368 and *Lipids*, (US), 1999, vol. 34, pp. 17-21).

It is being elucidated that LPA functions as an intercellular messenger that extracellularly acts via a cell surface receptor. The genes of the receptor, G-protein-coupled receptor, EDG2 (endothelial differentiation gene 2) (a.k.a. lpA1 (Lysophophatidic acid receptor 1) or VZG-1) (*Biochemical and Biophysical Research Communications*, (US), 1997, vol. 231, pp. 619-622), EDG4 (a.k.a. lpA2 (lysophophatidic acid receptor 2)) and EDG7 (a.k.a. lpA3 (lysophophatidic acid receptor 3)) gene have been cloned to the present date (*Molecular Pharmacology*, (US), 2000, vol. 58, pp. 1188-1196), and they have been reported to be LPA specific receptors (*FEBS Letters*, (DE), 2000, vol. 478, pp. 159-165 and *Prostaglandins & other Lipid Mediators* (US), 2001, vol. 64, pp. 21-32).

As the physiological activity of LPA, for example, cell growth promoting action, enhancing action on chemotactic and infiltrating activities, platelet aggregation action, action of cell contraction and the like are known, and LPA is particularly useful for the organs shown below, particularly for the disease/symptoms in organ shown below.

LPA has been reported to promote growth of stellate cell in the liver (*Biochemical and Biophysical Research Communications*, (US), 2000, vol. 248, pp. 436-440). LPA has also been reported to cause contraction of cultured activated stellate cells (*Biochemical and Biophysical Research Communications*, (US), 2000, vol. 277, pp. 72-78). When the contracting function of stellate cells is promoted by liver injury, it is considered that hepatic sinusoid microcirculation is impaired, the blood stream into the liver is prevented, causing portal hypertension and further esophageal varices (*Seminars in Liver Disease*, (US), 2001, vol. 21, pp. 337-349 and *Gut*, (UK), 2002, vol. 50, pp. 571-581). LPA has also been reported to induce chemotaxis of stellate cells (*Journal of Biomedical Science*, (CH), 2003, vol. 10, pp. 352-358). On the other hand, LPA has been reported to inhibit the growth of parenchymal cells stimulated by HGF (hepatic growth factor) (*Biochemical and Biophysical Research Communications*, (US), 2000, vol. 248, pp. 436-440).

As one of the pharmacological activities induced by LPA, the contracting phenomenon of rat colon and guinea pig ileum has been reported (*Journal of Pharmacy and Pharmacology*, (UK), 1982, vol. 34, pp. 514-516 and *Journal of Pharmacy and Pharmacology*, (UK), 1991, vol. 43, pp. 774-778). In recent years, it has been shown that LPA promotes the contraction of ileum, as do acetylcholine and high $K^+$ (*Canadian journal of physiology and pharmacology*, (CA), 2000, vol. 78, pp. 729-736).

With regard to pancreas, it has been described that LPA receptor antagonist has a decreasing action of pancreatic secretion (WO03/007991).

LPA has been reported to promote growth of vascular smooth muscle cell. WO01/060819 describes that the compound of Example 115 (methyl 3-([4-[4-([[1-(2-chlorophenyl)ethoxy]carbonyl]amino)-3-methyl-5-isoxazolyl]benzyl]-sulfanyl)propanoate) had a strong EDG2 antagonistic action and exhibited an improving action in peripheral circulation disorder model induced by lactic acid, which is an animal model of peripheral arterial obstruction.

There are reports that LPA has a contracting action on bladder smooth muscle cell isolated from bladder (*The Journal of urology*, (*US*), 1999, vol. 162, pp. 1779-1784), and promotes growth of prostate-derived epithelial cell (*The Journal of urology*, (*US*), 2000, vol. 163, pp. 1027-1032). In addition, WO02/062389 shows that LPA contracts the urinary tract and prostate in vitro and increases intraurethral pressure in vivo.

In addition, there is a report on the finding that, by LPA acting on a prostatic interstitial cell which expresses LPA receptor, the interstitial cell is grown and that the growth of the interstitial cell results in the progression of prostate hyperplasia (WO03/013605).

There are many reports on the involvement of LPA in the growth of cells responsible for the fibrosis of organs represented by fibroblasts in various organs. For example, smooth muscle cells (*The American journal of physiology*, (*US*), 1994, vol. 267, pp. C204-C210 and *Atherosclerosis*, (*IE*), 1997, vol. 130, pp. 121-131), renal mesangial cells (*Clinical science*, (*UK*), 1999, vol. 96, pp. 431-436), hepatic stellate cells (*Biochemical and Biophysical Research Communications*, (*US*), 2000, vol. 248, pp. 436-440), lung fibroblast (*The Journal of Pharmacology and Experimental Therapeutics*, (*US*), 2000, vol. 294, pp. 1076-1982), fibroblast (*Naunyn-Schmiedeberg's archives of pharmacology*, (*DE*), 1997, vol. 355, pp. 1-7) and the like can be mentioned. In general, when fibroblasts is proliferated, it is considered production of collagen is promoted, and also fibrosis of organs is considered to be promoted. Therefore, an LPA receptor antagonist is useful for the treatment or prophylaxis of fibrosis in various organs.

LPA promotes the growth of various cancer cells and is suggested to be related not only to diseases but also to infiltration and metastasis of cancer, because a promoting action of cancer cell infiltration and the like are observed (*Biochemical and Biophysical Research Communications*, (*US*), 1993, vol. 193, pp. 497-503).

LPA has been reported to promote the chemotactic ability of human monocytes (*The Journal of Biological Chemistry*, (*US*), 1995, vol. 270, pp. 25549-25556), and be involved in the growth and infiltration of T cells (*Biochimica et Biophysica Acta*, (*DE*), 2002, vol. 1582, pp. 168-174).

LPA has also been reported to cause neurite retraction and cell death in nerve cells, and is particularly suggested to be possibly involved in the injury of nerve cells during bleeding (*Journal of Neurochemistry*, (*UK*), 1993, vol. 61, pp. 340-343 and *Journal of Neurochemistry*, (*UK*), 1998, vol. 70, pp. 66-76).

A pharmaceutical agent that inhibits the above-mentioned physiological activities of LPA is considered to lead to the prophylaxis or treatment of fibrosis of organs (liver, kidney, lung, and the like), hepatic disease (acute or chronic hepatitis, liver fibrosis, liver cirrhosis, portal hypertension, regenerative failure, non-alcoholic steatohepatitis (NASH), liver hypofunction, hepatic blood flow disorder, and the like), cell proliferative disease (cancer (solid tumor, solid tumor metastasis, vascular fibroma, myeloma, multiple myeloma, Kaposi's sarcoma, leukemia, and the like) and invasive metastasis of cancer cell and the like), inflammatory disease (psoriasis, nephropathy, pneumonia, and the like), gastrointestinal tract disease (irritable bowel syndrome (IBS), inflammatory bowel disease (IBD), abnormal pancreatic secretion, and the like), renal disease, urinary tract-associated disease (benign prostatic hyperplasia or symptoms associated with neuropathic bladder disease, spinal cord tumor, hernia of intervertebral disk, spinal canal stenosis, symptoms derived from diabetes, lower urinary tract disease (obstruction of lower urinary tract and the like), inflammatory disease of lower urinary tract, dysuria, frequent urination, and the like), pancreas disease, abnormal angiogenesis-associated disease (arterial obstruction and the like), brain-associated disease (cerebral infarction, cerebral hemorrhage, and the like), peripheral neuropathy, and the like.

As a compound having an azole skeleton as in the present invention, for example, WO01/060819 discloses isoxazole compounds and isothiazole compounds represented by the following formulas, which have an LPA receptor antagonistic action. However, WO01/060819 does not disclose compounds in which either R1 or R2 is a hydrogen atom.

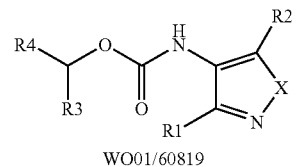

WO01/060819

X = O, S
R1 = alkyl group, aryl group, heterocyclic group, alkyloxy group, aryloxy group, alkythio group, arylthio group, each of which optionally having substituent(s), or halogen atom
R2 = alkyl group, aryl group, heterocyclic group, alkyloxy group, aryloxy group, each of which optionally having substituent(s), or halogen atom In addition, a production method of the isothiazole compound of the following formula has been reported (*Journal of Heterocyclic Chemistry*, (*US*), 1977, vol. 14, pp. 725), but its biological activity has not been described at all.

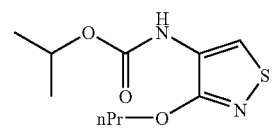

In addition, several production methods of compounds having a diazole skeleton as in the present invention have been reported.

For example, EP-A-0120821 discloses oxadiazole compounds of the following formula as a herbicide, but the pharmaceutical use of such a compound is not described at all in EP-A-0120821.

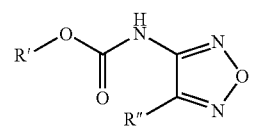

EP0120821

(R', R'') = (cyclohexyl, Me), (Et, Me), (Me, Me), (iPr, Me), (Ph, Me), (iBu, Me), (nBu, Me), (2-Et-hexyl, Me), (Et, Ph), (sec-Bu, Me), (allyl, Me)

As for such oxadiazole compounds, other references (*Journal of the Chemical Society, Perkin Transactions* 2, (*UK*), 1992, p. 1643, *Farmaco, Edizione Scientifica*, (*IT*), 1971, vol.

26, p. 241, etc.) report production methods thereof and the like, but do not describe their biological activities at all.

Furthermore, ZA-6800779 describes an oxadiazole compound of the following formula as one of the compounds having a central nervous system suppressing action, an anti-convulsion action, and a muscle relaxation action, but does not describe activity for any disease based on inhibition of the physiological activity of LPA as described in the present specification.

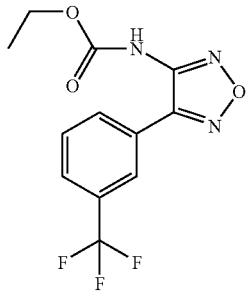

ZA6800779

While a production method of N-oxy-oxadiazole compounds of the following formula has been reported (*Journal of Heterocyclic Chemistry*, (US), 1972, vol. 9, p. 837 and *Journal of the Chemical Society, Perkin Transactions 2*, (UK), 1973, p. 1613), its biological activity has not been described at all.

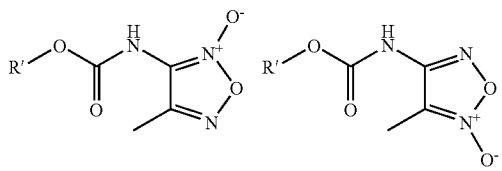

R' = Et, nPr, iPr, nBu, iBu, Bn

While a production method of thiadiazole compounds of the following formula has been reported (*Journal of the Chemical Society*), (UK), 1965, p. 5166), its biological activity has not been described at all.

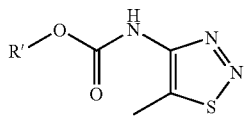

R' = Et, Bn

While a production method of thiadiazole compounds of the following formula has been described (*Chemical and Pharmaceutical Bulletin*, (UK), 1981, vol. 29, p. 1743), its biological activity has not been described at all.

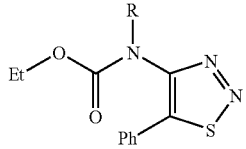

R = H, Me

SUMMARY OF THE INVENTION

Accordingly, it is one object of the present invention to provide novel compounds which are pharmaceutically active.

It is another object of the present invention to provide novel compounds which inhibit the physiological activity of LPA (hereinafter to be simply referred to as LPA inhibitory action).

It is another object of the present invention to provide novel methods for making such compounds.

It is another object of the present invention to provide novel pharmaceutical compositions which contain such a compound.

It is another object of the present invention to provide novel methods of using such a compound.

It is another object of the present invention to provide novel methods of using such a pharmaceutical composition.

It is another object of the present invention to provide novel methods for the prophylaxis or treatment of fibrosis of organs (liver, kidney, lung, and the like), hepatic disease (acute or chronic hepatitis, liver fibrosis, liver cirrhosis, portal hypertension, regenerative failure, non-alcoholic steatohepatitis (NASH), liver hypofunction, hepatic blood flow disorder, and the like), cell proliferative disease (cancer (solid tumor, solid tumor metastasis, vascular fibroma, myeloma, multiple myeloma, Kaposi's sarcoma, leukemia, and the like) and invasive metastasis of cancer cell and the like), inflammatory disease (psoriasis, nephropathy, pneumonia, and the like), gastrointestinal tract disease (irritable bowel syndrome (IBS), inflammatory bowel disease (IBD), abnormal pancreatic secretion, and the like), renal disease, urinary tract-associated disease (benign prostatic hyperplasia or symptoms associated with neuropathic bladder disease, spinal cord tumor, hernia of intervertebral disk, spinal canal stenosis, symptoms derived from diabetes, lower urinary tract disease (obstruction of lower urinary tract and the like), inflammatory disease of lower urinary tract, dysuria, frequent urination, and the like), pancreas disease, abnormal angiogenesis-associated disease (arterial obstruction and the like), brain-associated disease (cerebral infarction, cerebral hemorrhage, and the like), peripheral neuropathy, and the like by the use of such a compound or such a pharmaceutical composition.

These and other objects, which will become apparent during the following detailed description, have been achieved by the inventors' synthesizing of various azole compounds and the examination of the inhibitory activity thereof using the evaluation system (evaluation system of intracellular $Ca^{2+}$ concentration increasing action by LPA) described in this specification. As a result, we have surprisingly found that such compounds show a strong inhibitory activity.

Accordingly, the present invention provides the following:

(1) An azole compound represented by the following formula I:

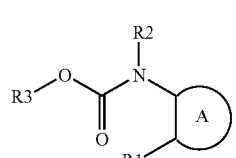

formula I wherein ring A is

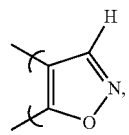

ring-1

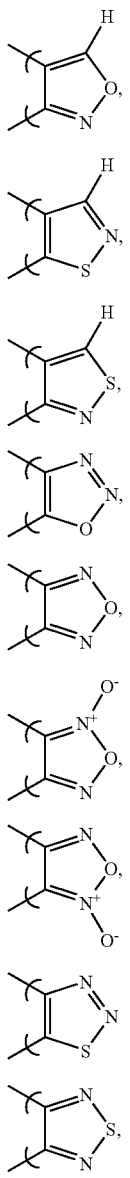

ring-2 ring-3 ring-4 ring-5 ring-6 ring-7 ring-8 ring-9 ring-10

R1 is any of a substituted or unsubstituted alkyl group, a substituted or unsubstituted cycloalkyl group, a substituted or unsubstituted cycloalkenyl group, a substituted or unsubstituted aryl group, a substituted or unsubstituted heteroaryl group, a substituted or unsubstituted heterocyclic group, a substituted or unsubstituted aralkyl group, a substituted or unsubstituted alkenyl group, a substituted or unsubstituted alkynyl group, a halogen atom, a substituted or unsubstituted alkoxy group, a substituted or unsubstituted aryloxy group, a substituted or unsubstituted heteroaryloxy group, a substituted or unsubstituted alkylthio group, a substituted or unsubstituted arylthio group, a substituted or unsubstituted heteroarylthio group, a substituted or unsubstituted alkylamino group, a substituted or unsubstituted dialkylamino group, a substituted or unsubstituted cycloalkylamino group, a substituted or unsubstituted dicycloalkylamino group, a substituted or unsubstituted arylamino group, a substituted or unsubstituted heteroarylamino group, a substituted or unsubstituted alkanoyl group, a substituted or unsubstituted carboxylic acid ester group, a substituted or unsubstituted carbamoyl group, and an amino group optionally substituted by amino-protecting group(s);

R2 is any of a hydrogen atom, a substituted or unsubstituted lower alkyl group, a substituted or unsubstituted aralkyl group, a substituted or unsubstituted aryl group, a substituted or unsubstituted heteroaryl group, and a hydroxyl group; and R3 is any of a substituted or unsubstituted alkyl group, a substituted or unsubstituted cycloalkyl group, a substituted or unsubstituted aryl group, a substituted or unsubstituted heteroaryl group, a substituted or unsubstituted heterocyclic group, and a group represented by the following formula II:

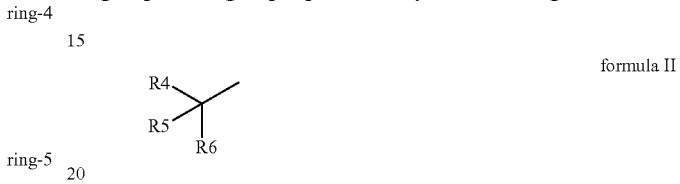

formula II wherein

R4 is any of a substituted or unsubstituted alkyl group, a substituted or unsubstituted cycloalkyl group, a substituted or unsubstituted cycloalkenyl group, a substituted or unsubstituted aryl group, a substituted or unsubstituted heteroaryl group, a substituted or unsubstituted heterocyclic group, a substituted or unsubstituted aralkyl group, a substituted or unsubstituted alkenyl group, a substituted or unsubstituted alkynyl group, a halogen atom, a substituted or unsubstituted alkoxy group, a substituted or unsubstituted aryloxy group, a substituted or unsubstituted heteroaryloxy group, a substituted or unsubstituted alkylthio group, a substituted or unsubstituted arylthio group, a substituted or unsubstituted heteroarylthio group, a substituted or unsubstituted alkylamino group, a substituted or unsubstituted dialkylamino group, a substituted or unsubstituted cycloalkylamino group, a substituted or unsubstituted dicycloalkylamino group, a substituted or unsubstituted arylamino group, a substituted or unsubstituted heteroarylamino group, and an amino group optionally substituted by amino-protecting group(s); and R5 and R6 may be the same or different and each is any of a hydrogen atom, a substituted or unsubstituted lower alkyl group, a substituted or unsubstituted aryl group, a substituted or unsubstituted heteroaryl group, a substituted or unsubstituted heterocyclic group, and a substituted or unsubstituted aralkyl group, or R5 and R6 optionally form, together with the carbon atom bonded thereto, a 3- to 8-membered ring, provided that the following (i) to (viii) are excluded:

(i) a compound wherein ring A is ring-4, R1 is a normal propoxy group, R2 is a hydrogen atom, and R3 is a isopropyl group;

(ii) a compound wherein ring A is ring-6, and R1 is a methyl group;

(iii) a compound wherein ring A is ring-6, R1 is a phenyl group, R2 is a hydrogen atom, and R3 is an ethyl group;

(iv) a compound wherein ring A is ring-6, R1 is a m-trifluoromethylphenyl group, and R2 is a hydrogen atom, R3 is an ethyl group;

(v) a compound wherein ring A is ring-7, and R1 is a methyl group;

(vi) a compound wherein ring A is ring-8, and R1 is a methyl group;

(vii) a compound wherein ring A is ring-9, and R1 is a methyl group, R2 is a hydrogen atom, and R3 is an ethyl group or a benzyl group; and (viii) a compound wherein ring A is ring-9, R1 is a phenyl group, R2 is a hydrogen atom or a methyl group, and R3 is an ethyl group, or a pharmaceutically acceptable salt thereof.

(2) The azole compound of the above-mentioned (1), wherein, in formula I,

R1 is any of a substituted or unsubstituted alkyl group, a substituted or unsubstituted cycloalkyl group, a substituted or unsubstituted aryl group, a substituted or unsubstituted heteroaryl group, a substituted or unsubstituted heterocyclic group, a substituted or unsubstituted aralkyl group, a substituted or unsubstituted alkenyl group, a substituted or unsubstituted alkynyl group, a halogen atom, a substituted or unsubstituted alkoxy group, a substituted or unsubstituted aryloxy group, a substituted or unsubstituted heteroaryloxy group, a substituted or unsubstituted alkylthio group, a substituted or unsubstituted arylthio group, a substituted or unsubstituted heteroarylthio group, a substituted or unsubstituted alkylamino group, a substituted or unsubstituted dialkylamino group, a substituted or unsubstituted cycloalkylamino group, a substituted or unsubstituted dicycloalkylamino group, a substituted or unsubstituted arylamino group, a substituted or unsubstituted heteroarylamino group, a substituted or unsubstituted alkanoyl group, a substituted or unsubstituted carboxylic acid ester group, a substituted or unsubstituted carbamoyl group, and an amino group optionally substituted by amino-protecting group(s); and R4 is any of a substituted or unsubstituted alkyl group, a substituted or unsubstituted cycloalkyl group, a substituted or unsubstituted aryl group, a substituted or unsubstituted heteroaryl group, a substituted or unsubstituted heterocyclic group, a substituted or unsubstituted aralkyl group, a substituted or unsubstituted alkenyl group, a substituted or unsubstituted alkynyl group, a halogen atom, a substituted or unsubstituted alkoxy group, a substituted or unsubstituted aryloxy group, a substituted or unsubstituted heteroaryloxy group, a substituted or unsubstituted alkylthio group, a substituted or unsubstituted arylthio group, a substituted or unsubstituted heteroarylthio group, a substituted or unsubstituted alkylamino group, a substituted or unsubstituted dialkylamino group, a substituted or unsubstituted cycloalkylamino group, a substituted or unsubstituted dicycloalkylamino group, a substituted or unsubstituted arylamino group, a substituted or unsubstituted heteroarylamino group, and an amino group optionally substituted by amino-protecting group(s), or a pharmaceutically acceptable salt thereof.

(3) The azole compound of the above-mentioned (1), wherein, in formula I,

R2 is any of a hydrogen atom, a substituted or unsubstituted lower alkyl group, a substituted or unsubstituted aralkyl group, and a hydroxyl group; and R3 is a group represented by the following formula II:

formula II wherein

R4 is any of a substituted or unsubstituted alkyl group, a substituted or unsubstituted cycloalkyl group, a substituted or unsubstituted cycloalkenyl group, a substituted or unsubstituted aryl group, a substituted or unsubstituted heteroaryl group, a substituted or unsubstituted heterocyclic group, a substituted or unsubstituted aralkyl group, a substituted or unsubstituted alkenyl group, a substituted or unsubstituted alkynyl group, a halogen atom, a substituted or unsubstituted alkoxy group, a substituted or unsubstituted aryloxy group, a substituted or unsubstituted heteroaryloxy group, a substituted or unsubstituted alkylthio group, a substituted or unsubstituted arylthio group, a substituted or unsubstituted heteroarylthio group, a substituted or unsubstituted alkylamino group, a substituted or unsubstituted dialkylamino group, a substituted or unsubstituted arylamino group, a substituted or unsubstituted heteroarylamino group, and an amino group optionally substituted by amino-protecting group(s); and R5 and R6 may be the same or different and each is any of a hydrogen atom and a substituted or unsubstituted lower alkyl group, or R5 and R6 optionally form, together with the carbon atom bonded thereto, a 3- to 8-membered ring, or a pharmaceutically acceptable salt thereof.

(4) The azole compound of the above-mentioned (3), wherein, in formula I,

R1 is any of a substituted or unsubstituted alkyl group, a substituted or unsubstituted cycloalkyl group, a substituted or unsubstituted aryl group, a substituted or unsubstituted heteroaryl group, a substituted or unsubstituted heterocyclic group, a substituted or unsubstituted aralkyl group, a substituted or unsubstituted alkenyl group, a substituted or unsubstituted alkynyl group, a halogen atom, a substituted or unsubstituted alkoxy group, a substituted or unsubstituted aryloxy group, a substituted or unsubstituted heteroaryloxy group, a substituted or unsubstituted alkylthio group, a substituted or unsubstituted arylthio group, a substituted or unsubstituted heteroarylthio group, a substituted or unsubstituted alkylamino group, a substituted or unsubstituted dialkylamino group, a substituted or unsubstituted cycloalkylamino group, a substituted or unsubstituted dicycloalkylamino group, a substituted or unsubstituted arylamino group, a substituted or unsubstituted heteroarylamino group, a substituted or unsubstituted alkanoyl group, a substituted or unsubstituted carboxylic acid ester group, a substituted or unsubstituted carbamoyl group, and an amino group optionally substituted by amino-protecting group(s); and R4 is any of a substituted or unsubstituted alkyl group, a substituted or unsubstituted cycloalkyl group, a substituted or unsubstituted aryl group, a substituted or unsubstituted heteroaryl group, a substituted or unsubstituted heterocyclic group, a substituted or unsubstituted aralkyl group, a substituted or unsubstituted alkenyl group, a substituted or unsubstituted alkynyl group, a halogen atom, a substituted or unsubstituted alkoxy group, a substituted or unsubstituted aryloxy group, a substituted or unsubstituted heteroaryloxy group, a substituted or unsubstituted alkylthio group, a substituted or unsubstituted arylthio group, a substituted or unsubstituted heteroarylthio group, a substituted or unsubstituted alkylamino group, a substituted or unsubstituted dialkylamino group, a substituted or unsubstituted arylamino group, a substituted or unsubstituted heteroarylamino group, and an amino group optionally substituted by amino-protecting group(s), or a pharmaceutically acceptable salt thereof.

(5) The azole compound of the above-mentioned (3), wherein, in formula I, the substituent of the group for R1 is any of a cyano group and a group represented by the following formula III:

Z-Y—X—  formula III wherein

X and Y may be the same or different and each is any of a substituted or unsubstituted lower alkylene group, a substituted or unsubstituted lower alkenylene group, a substituted or unsubstituted lower alkynylene group, a substituted or unsubstituted cycloalkylene group, a substituted or unsubstituted arylene group, a substituted or unsubstituted heteroarylene group, a substituted or unsubstituted heterocyclylene group, a carbonyl group, an oxygen atom, an sulfur atom, a sulfinyl group, a sulfonyl group, a substituted or unsubstituted amino group, and a bond; and Z is any of a substituted or unsubstituted lower alkyl group, a substituted or unsubstituted lower alkenyl group, a substituted or unsubstituted lower alkynyl group, a substituted or unsubstituted alkanoyl group, a substituted or unsubstituted aryl group, a substituted or unsubstituted heteroaryl group, a substituted or unsubstituted heterocyclic group, a substituted or unsubstituted alkoxy group, a substituted or unsubstituted aryloxy group, a substituted or unsubstituted heteroaryloxy group, a substituted or unsubstituted alkylthio group, a substituted or unsubstituted arylthio group, a substituted or unsubstituted heteroarylthio group, a substituted or unsubstituted alkylamino group, a substituted or unsubstituted dialkylamino group, a substituted or unsubstituted cycloalkylamino group, a substituted or unsubstituted dicycloalkylamino group, a substituted or unsubstituted arylamino group, a substituted or unsubstituted heteroarylamino group, and a substituted or unsubstituted carbamoyl group, wherein the substituent of the group for Z is any of a carboxyl group, a carboxylic acid ester group, a substituted or unsubstituted carbamoyl group, a cyano group, a hydroxyl group, a sulfonic acid group, a sulfonamido group, a phosphoric acid group, phosphoric acid monoester group, phosphoric acid diester group, an amino group optionally substituted by amino-protecting group(s), a thiol group, a halogen atom, a substituted or unsubstituted aryl group, a substituted or unsubstituted heteroaryl group, a substituted or unsubstituted heterocyclic group, a substituted or unsubstituted alkanoyl group, a substituted or unsubstituted arylcarbonyl group, and a substituted or unsubstituted heteroarylcarbonyl group, and the group for Z optionally has multiple substituents described above that may be the same or different;

R2 is any of a hydrogen atom, a substituted or unsubstituted lower alkyl group, and a substituted or unsubstituted aralkyl group;

R4 is any of a substituted or unsubstituted alkyl group, a substituted or unsubstituted cycloalkyl group, a substituted or unsubstituted cycloalkenyl group, a substituted or unsubstituted aryl group, a substituted or unsubstituted heteroaryl group, a substituted or unsubstituted heterocyclic group, a substituted or unsubstituted aralkyl group, a substituted or unsubstituted alkenyl group, a substituted or unsubstituted alkynyl group, and a halogen atom; and R5 and R6 may be the same or different and each is any of a hydrogen atom and a substituted or unsubstituted lower alkyl group, or a pharmaceutically acceptable salt thereof.

(6) The azole compound of the above-mentioned (3), wherein, in formula I, the substituent of the group for R1 is any of a hydroxyl group and a group represented by the following formula III:

Z-Y-X—         formula III wherein

X is any of an oxygen atom, a substituted or unsubstituted amino group, a sulfur atom, and a bond;

Y is any of a carbonyl group, a sulfonyl group, and a bond; and

Z is any of a substituted or unsubstituted alkyl group, a substituted or unsubstituted alkenyl group, a substituted or unsubstituted alkynyl group, a substituted or unsubstituted alkanoyl group, a substituted or unsubstituted aryl group, a substituted or unsubstituted heteroaryl group, a substituted or unsubstituted heterocyclic group, a substituted or unsubstituted alkoxy group, a substituted or unsubstituted aryloxy group, a substituted or unsubstituted heteroaryloxy group, a substituted or unsubstituted alkylthio group, a substituted or unsubstituted arylthio group, a substituted or unsubstituted heteroarylthio group, a substituted or unsubstituted alkylamino group, a substituted or unsubstituted dialkylamino group, a substituted or unsubstituted cycloalkylamino group, a substituted or unsubstituted dicycloalkylamino group, a substituted or unsubstituted arylamino group, and a substituted or unsubstituted heteroarylamino group, wherein the substituent of the group for Z is any of a lower alkyl group, a carboxyl group, a carboxylic acid ester group, a substituted or unsubstituted alkanoyloxy group, a substituted or unsubstituted carbamoyl group, a cyano group, a hydroxyl group, a sulfonic acid group, a sulfonamido group, a phosphoric acid group, a phosphoric acid monoester group, a phosphoric acid diester group, an amino group optionally substituted by amino-protecting group(s), a thiol group, a halogen atom, a substituted or unsubstituted aryl group, a substituted or unsubstituted heteroaryl group, a substituted or unsubstituted heterocyclic group, a substituted or unsubstituted alkanoyl group, a substituted or unsubstituted arylcarbonyl group, and a substituted or unsubstituted heteroarylcarbonyl group, and the group for Z optionally has multiple substituents described above that may be the same or different;

R2 is any of a hydrogen atom, a substituted or unsubstituted lower alkyl group, and a substituted or unsubstituted aralkyl group;

R4 is any of a substituted or unsubstituted alkyl group, a substituted or unsubstituted cycloalkyl group, a substituted or unsubstituted cycloalkenyl group, a substituted or unsubstituted aryl group, a substituted or unsubstituted heteroaryl group, a substituted or unsubstituted heterocyclic group, a substituted or unsubstituted aralkyl group, a substituted or unsubstituted alkenyl group, a substituted or unsubstituted alkynyl group, and a halogen atom; and R5 and R6 may be the same or different and each is any of a hydrogen atom and a substituted or unsubstituted lower alkyl group, or a pharmaceutically acceptable salt thereof.

(7) The azole compound of the above-mentioned (5), wherein, in formula I,

R1 is any of a substituted or unsubstituted alkyl group, a substituted or unsubstituted cycloalkyl group, a substituted or unsubstituted aryl group, a substituted or unsubstituted heteroaryl group, a substituted or unsubstituted heterocyclic group, a substituted or unsubstituted aralkyl group, a substituted or unsubstituted alkenyl group, a substituted or unsubstituted alkynyl group, a halogen atom, a substituted or unsubstituted alkoxy group, a substituted or unsubstituted aryloxy group, a substituted or unsubstituted heteroaryloxy group, a substituted or unsubstituted alkylthio group, a substituted or unsubstituted arylthio group, a substituted or unsubstituted heteroarylthio group, a substituted or unsubstituted alkylamino group, a substituted or unsubstituted dialkylamino group, a substituted or unsubstituted cycloalkylamino group, a substituted or unsubstituted dicycloalkylamino group, a substituted or unsubstituted arylamino group, a substituted or unsubstituted heteroarylamino group, a substituted or unsubstituted alkanoyl group, a substituted or unsubstituted carboxylic acid ester group, a substituted or unsubstituted carbamoyl group, and an amino group optionally substituted by amino-protecting group(s); and R4 is any of a substituted or unsubstituted alkyl group, a substituted or unsubstituted cycloalkyl group, a substituted or unsubstituted aryl group, a substituted or unsubstituted heteroaryl group, a substituted or unsubstituted heterocyclic group, a substituted or unsubstituted aralkyl group, a substituted or unsubstituted alkenyl group, a substituted or unsubstituted alkynyl group, and a halogen atom, or a pharmaceutically acceptable salt thereof.

(8) The azole compound of the above-mentioned (5) or (7), wherein, in formula I, R1 is any of a substituted or unsubstituted alkyl group, a substituted or unsubstituted cycloalkyl group, a substituted or unsubstituted aryl group, a substituted or unsubstituted heteroaryl group, a substituted or unsubstituted heterocyclic group, and a substituted or unsubstituted aralkyl group, or a pharmaceutically acceptable salt thereof.

(9) The azole compound of the above-mentioned (2), wherein, in formula I,

R1 is a substituted phenyl group, wherein the substituent of the group for R1 is any of a cyano group and a group represented by the following formula III:

Z-Y—X—          formula III wherein

X is any of a methylene group and an ethylene group,

Y is any of a sulfur atom, a sulfinyl group, a sulfonyl group, an oxygen atom, a substituted or unsubstituted amino group, and a methylene group, and Z is any of a substituted or unsubstituted lower alkyl group, a substituted or unsubstituted lower alkenyl group, a substituted or unsubstituted alkanoyl group, a substituted or unsubstituted triazole group, and a substituted or unsubstituted tetrazole group, wherein the substituent of the group for Z is any of a carboxyl group, an alkoxycarbonyl group, a furyl group, a phenyl group, a hydroxyl group, a carbamoyl group, a carbamoyl group substituted by lower alkyl group(s), a carbamoyl group substituted by carboxy lower alkyl group(s), a carbamoyl group substituted by lower alkyl group(s) substituted by a furyl group, an amino group optionally substituted by amino-protecting group(s), a sulfonic acid group, a pyrrolylcarbonyl group, a pyridyl group, and a halogen atom, and the group for Z optionally has multiple substituents described above that may be the same or different;

R2 is a hydrogen atom; and

R3 is a group represented by the following formula II:

formula II wherein

R4 is a substituted or unsubstituted phenyl group wherein the substituent of the group for R4 is a halogen atom, R5 is any of a hydrogen atom, a lower alkyl group, and a lower alkyl group substituted by 1 to 3 halogen atoms, and R6 is a hydrogen atom, or a pharmaceutically acceptable salt thereof.

(10) The azole compound of the above-mentioned (6), wherein, in formula I,

R1 is any of a substituted or unsubstituted phenyl group, a substituted or unsubstituted heteroaryl group, a substituted or unsubstituted heterocyclic group, a substituted or unsubstituted cycloalkyl group, and a substituted or unsubstituted cycloalkenyl group wherein the substituent of the group for R1 is any of a hydroxyl group and a group represented by the following formula III:

Z-Y—X—          formula III wherein

X is any of an oxygen atom, a substituted or unsubstituted amino group, a sulfur atom, and a bond, Y is any of a carbonyl group, a sulfonyl group, and a bond, and Z is a substituted or unsubstituted alkyl group, wherein the substituent of the group for Z is any of a lower alkyl group, a carboxyl group, a carboxylic acid ester group, a substituted or unsubstituted alkanoyloxy group, a substituted or unsubstituted carbamoyl group, a cyano group, a hydroxyl group, a sulfonic acid group, a sulfonamido group, a phosphoric acid group, a phosphoric acid monoester group, a phosphoric acid diester group, an amino group optionally substituted by amino-protecting group(s), a thiol group, a halogen atom, a substituted or unsubstituted aryl group, a substituted or unsubstituted heteroaryl group, a substituted or unsubstituted heterocyclic group, a substituted or unsubstituted alkanoyl group, a substituted or unsubstituted arylcarbonyl group, and a substituted or unsubstituted heteroarylcarbonyl group, and the group for Z optionally has multiple substituents described above that may be the same or different, or a pharmaceutically acceptable salt thereof.

(11) The azole compound of the above-mentioned (5), wherein, in formula I,

R1 is any of a substituted or unsubstituted aryl group, a substituted or unsubstituted heteroaryl group, a substituted or unsubstituted heterocyclic group, a substituted or unsubstituted cycloalkyl group, and a substituted or unsubstituted cycloalkenyl group, wherein the substituent of the group for R1 is a group represented by the following formula III:

Z-Y—X—          formula III wherein each symbol is as defined in the above-mentioned (5), R2 is a hydrogen atom;

R4 is any of a substituted or unsubstituted aryl group, a substituted or unsubstituted heteroaryl group, a substituted or unsubstituted heterocyclic group, a substituted or unsubstituted cycloalkyl group, and a substituted or unsubstituted cycloalkenyl group;

R5 is a substituted or unsubstituted lower alkyl group; and

R6 is a hydrogen atom, or a pharmaceutically acceptable salt thereof.

(12) The azole compound of the above-mentioned (11), wherein, in formula I,

R4 is a substituted or unsubstituted cycloalkenyl group, or a pharmaceutically acceptable salt thereof.

(13) The azole compound of any of the above-mentioned (1) to (12), wherein, in formula I, ring A is ring-1, or a pharmaceutically acceptable salt thereof.

(14) The azole compound of any of the above-mentioned (1) to (12), wherein, in formula I, ring A is ring-2, or a pharmaceutically acceptable salt thereof.

(15) The azole compound of any of the above-mentioned (1) to (12), wherein, in formula I, ring A is ring-3, or a pharmaceutically acceptable salt thereof.

(16) The azole compound of any of the above-mentioned (1) to (12), wherein, in formula I, ring A is ring-4, or a pharmaceutically acceptable salt thereof.

(17) The azole compound of any of the above-mentioned (1) to (12), wherein, in formula I, ring A is ring-5, or a pharmaceutically acceptable salt thereof.

(18) The azole compound of any of the above-mentioned (1) to (12), wherein, in formula I, ring A is ring-6, or a pharmaceutically acceptable salt thereof.

(19) The azole compound of any of the above-mentioned (1) to (12), wherein, in formula I, ring A is ring-7, or a pharmaceutically acceptable salt thereof.

(20) The azole compound of any of the above-mentioned (1) to (12), wherein, in formula I, ring A is ring-8, or a pharmaceutically acceptable salt thereof.

(21) The azole compound of any of the above-mentioned (1) to (12), wherein, in formula I, ring A is ring-9, or a pharmaceutically acceptable salt thereof.

(22) The azole compound of any of the above-mentioned (1) to (12), wherein, in formula I, ring A is ring-10, or a pharmaceutically acceptable salt thereof.

(23) The azole compound of the above-mentioned (10), wherein, in formula I, ring A is any of ring-1 and ring-2; and R1 is a substituted phenyl group, wherein the substituent of the group for R1 is any of a hydroxyl group and a group represented by the following formula III:

$$Z-Y-X- \qquad \text{formula III}$$

wherein

X is any of an oxygen atom and a substituted or unsubstituted amino group,

Y is any of a carbonyl group and a bond, and

Z is a substituted or unsubstituted alkyl group wherein the substituent of the group for Z is any of a lower alkyl group, a carboxyl group, a carboxylic acid ester group, a substituted or unsubstituted alkanoyloxy group, a substituted or unsubstituted carbamoyl group, a cyano group, a hydroxyl group, a sulfonic acid group, a sulfonamido group, a phosphoric acid group, a phosphoric acid monoester group, a phosphoric acid diester group, an amino group optionally substituted by amino-protecting group(s), a thiol group, a halogen atom, a substituted or unsubstituted aryl group, a substituted or unsubstituted heteroaryl group, a substituted or unsubstituted heterocyclic group, a substituted or unsubstituted alkanoyl group, a substituted or unsubstituted arylcarbonyl group, and a substituted or unsubstituted heteroarylcarbonyl group, and the group for Z optionally has multiple substituents described above that may be the same or different, or a pharmaceutically acceptable salt thereof.

(24) The azole compound of the above-mentioned (11), wherein, in formula I, ring A is any of ring-1 and ring-2;

R1 is a substituted phenyl group;

X is any of a substituted or unsubstituted methylene group, a substituted or unsubstituted ethylene group and a substituted or unsubstituted vinylene group;

Y is any of a sulfur atom, a sulfonyl group, a substituted or unsubstituted methylene group, and an oxygen atom;

Z is any of a substituted methyl group, a substituted ethyl group, a substituted propyl group, and a substituted carbamoyl group, wherein the substituent of the group for Z is any of a carboxyl group, a carboxylic acid ester group, an acetylamino group, a sulfonic acid group, and a hydroxyl group, and the group for Z optionally has multiple substituents described above that may be the same or different;

R4 is any of a substituted phenyl group, a substituted cyclopentenyl group, a substituted cyclohexenyl group, and a substituted thienyl group, wherein the substituent of the group for R4 is any of a chlorine atom, a bromine atom and a substituted or unsubstituted lower alkyl group; and R5 is a methyl group, or a pharmaceutically acceptable salt thereof.

(25) The azole compound of the above-mentioned (23), wherein, in formula I, the substituent of the group for R1 is any of a hydroxyl group and a group represented by the following formula III:

$$Z-Y-X- \qquad \text{formula III}$$

wherein

X is any of an oxygen atom and a substituted or unsubstituted amino group,

Y is any of a carbonyl group and a bond, and

Z is a substituted or unsubstituted alkyl group,
wherein the substituent of the group for Z is any of a lower alkyl group, a carboxyl group, a carboxylic acid ester group, an alkanoyloxy group, a hydroxyl group, a sulfonic acid group, and an amino group optionally substituted by amino-protecting group(s), and the group for Z optionally has multiple substituents described above that may be the same or different, or a pharmaceutically acceptable salt thereof.

(26) The azole compound of the above-mentioned (24), wherein, in formula I,

X is any of a methylene group, a ethylene group, and a vinylene group;

Y is any of a sulfur atom, a sulfonyl group, a methylene group, and an oxygen atom;

Z is any of a substituted methyl group, a substituted ethyl group, a substituted propyl group, and a substituted carbamoyl group,
wherein the substituent of the group for Z is any of a carboxyl group, a carboxylic acid ester group, an acetylamino group, and a sulfonic acid group, and the group for Z optionally has multiple substituents described above that may be the same or different; and R4 is any of a substituted phenyl group, a substituted cyclopentenyl group, and a substituted cyclohexenyl group,
wherein the substituent of the group for R4 is any of a chlorine atom and a bromine atom, or a pharmaceutically acceptable salt thereof.

(27) A pharmaceutical agent comprising the compound of any of the above-mentioned (1) to (26) as an active ingredient.

(28) The pharmaceutical agent of the above-mentioned (27), which is an inhibitor of the physiological activity of LPA.

(29) The pharmaceutical agent of the above-mentioned (27), which is an agent for the prophylaxis or treatment of liver disease.

(30) The pharmaceutical agent of the above-mentioned (27), which is an agent for the prophylaxis or treatment of organ fibrosis.

(31) The pharmaceutical agent of the above-mentioned (27), which is an agent for improving liver function.

(32) A pharmaceutical composition comprising the compound of any of the above-mentioned (1) to (26) as an active ingredient and a pharmaceutically acceptable carrier.

(33) A method of inhibiting the physiological activity of LPA, which comprises administering an effective amount of the compound of any of the above-mentioned (1) to (26) to a mammal.

(34) A method for the prophylaxis or treatment of hepatic disease, which comprises administering an effective amount of the compound of any of the above-mentioned (1) to (26) to a mammal.

(35) A method for the prophylaxis or treatment of organ fibrosis, which comprises administering an effective amount of the compound of any of the above-mentioned (1) to (26) to a mammal.

(36) A method of improving liver function, which comprises administering an effective amount of the compound of any of the above-mentioned (1) to (26) to a mammal.

(37) Use of the compound of any of the above-mentioned (1) to (26) for the production of an inhibitor of the physiological activity of LPA.

(38) Use of the compound of any of the above-mentioned (1) to (26) for the production of an agent for the prophylaxis or treatment of hepatic disease.

(39) Use of the compound of any of the above-mentioned (1) to (26) for the production of an agent for the prophylaxis or treatment of organ fibrosis.

(40) Use of the compound of any of the above-mentioned (1) to (26) for the production of an agent for improving liver function.

(41) A commercial package comprising the pharmaceutical composition of the above-mentioned (32), and a written matter associated therewith, the written matter stating that the pharmaceutical composition can or should be used for inhibiting the physiological activity of LPA.

(42) A commercial package comprising the pharmaceutical composition of the above-mentioned (32), and a written matter associated therewith, the written matter stating that the pharmaceutical composition can or should be used for the prophylaxis or treatment of liver disease.

(43) A commercial package comprising the pharmaceutical composition of the above-mentioned (32), and a written matter associated therewith, the written matter stating that the pharmaceutical composition can or should be used for the prophylaxis or treatment of organ fibrosis.

(44) A commercial package comprising the pharmaceutical composition of the above-mentioned (32), and a written matter associated therewith, the written matter stating that the pharmaceutical composition can or should be used for improving liver function.

EFFECT OF THE INVENTION

The present invention provides compounds which inhibit the physiological activity of LPA and pharmaceutically acceptable salts thereof. Such compounds are useful for the prophylaxis or treatment of fibrosis of organs (liver, kidney, lung, and the like), hepatic disease (acute or chronic hepatitis, liver fibrosis, liver cirrhosis, portal hypertension, regenerative failure, non-alcoholic steatohepatitis (NASH), liver hypofunction, hepatic blood flow disorder, and the like), cell proliferative disease (cancer (solid tumor, solid tumor metastasis, vascular fibroma, myeloma, multiple myeloma, Kaposi's sarcoma, leukemia, and the like) and invasive metastasis of cancer cell and the like), inflammatory disease (psoriasis, nephropathy, pneumonia, and the like), gastrointestinal tract disease (irritable bowel syndrome (IBS), inflammatory bowel disease (IBD), abnormal pancreatic secretion, and the like), renal disease, urinary tract-associated disease (benign prostatic hyperplasia or symptoms associated with neuropathic bladder disease, spinal cord tumor, hernia of intervertebral disk, spinal canal stenosis, symptoms derived from diabetes, lower urinary tract disease (obstruction of lower urinary tract and the like), inflammatory disease of lower urinary tract, dysuria, frequent urination, and the like), pancreas disease, abnormal angiogenesis-associated disease (arterial obstruction and the like), brain-associated disease (cerebral infarction, cerebral hemorrhage, and the like), peripheral neuropathy, and the like. Such compounds and pharmaceutical compositions are particularly useful for the prophylaxis or treatment of fibrosis of organs (liver, kidney, lung, and the like) and liver diseases.

DETAILED DESCRIPTION OF THE PREFERRED EMBODIMENTS

The action to "inhibit the physiological activity of LPA" in the present invention may be any as long as the physiological activity of LPA is finally inhibited (LPA inhibitory action). For example, it may be an action to suppress production of LPA itself, or an action to antagonize LPA receptors. Preferably, the compounds of the present invention inhibit the physiological activity of LPA by an LPA receptor antagonistic action.

In the present invention, the "improvement of liver function" means improving test value that worsens when suffering a hepatic disease. For example, improvement of an increase in γ-GTP, improvement of a decrease in total protein and albumin value, improvement of a prolonged prothrombin time, improvement of a decrease in the total cholesterol value, improvement of an increase in bile acid value, improvement of an increase in hyaluronic acid value, improvement of a decrease in platelet count, and the like can be mentioned.

As the "alkyl group" in the present invention, for example, a straight or branched chain $C_{1-10}$ alkyl group such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl, 2-ethylbutyl, n-heptyl, 1-methylheptyl, 1-ethylhexyl, n-octyl, 1-methylheptyl, nonyl, and the like, and the like can be mentioned.

In addition, as the "lower alkyl group" in the present invention, for example, a straight $C_{1-6}$ alkyl group such as methyl, ethyl, n-propyl, n-butyl, n-pentyl, n-hexyl, and the like, a branched chain $C_{1-6}$ alkyl group such as isopropyl, isobutyl, neopentyl, sec-butyl, tert-butyl, and the like, and the like can be mentioned.

As the "cycloalkyl group" in the present invention, for example, a $C_{3-9}$ cycloalkyl group such as cyclopropyl, cyclobutyl, cyclopentyl, cyclohexyl, cycloheptyl, cyclooctyl, cyclononyl, and the like, and the like can be mentioned.

The cycloalkyl moiety of the "cycloalkylene group" in the present invention is as defined for the above-mentioned cycloalkyl group.

As the "cycloalkenyl group" in the present invention, for example, a $C_{3-9}$ cycloalkenyl group such as cyclopropenyl, cyclobutenyl, cyclopentenyl, cyclohexenyl, cycloheptenyl, cyclooctenyl, cyclononenyl, and the like, and the like can be mentioned.

As the "alkenyl group" in the present invention, for example, a straight or branched chain $C_{2-8}$ alkenyl group such as vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, 1-heptenyl, 1-octenyl, and the like, and the like can be mentioned.

In addition, as the "lower alkenyl group" in the present invention, a straight or branched chain $C_{2-6}$ alkenyl group and the like can be mentioned.

As the "alkynyl group" in the present invention, for example, a straight or branched chain $C_{2-8}$ alkynyl group such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl, and the like can be mentioned.

In addition, as the "lower alkynyl group" in the present invention, a straight or branched chain $C_{2-6}$ alkyl group and the like can be mentioned.

The alkyl moiety of the "alkoxy group" in the present invention is as defined for the above-mentioned alkyl group, and similarly, the alkyl moiety of the "lower alkoxy group" is as defined for the above-mentioned lower alkyl group.

The "aryl group" in the present invention is preferably a monocyclic to tricyclic aromatic hydrocarbon group having 6 to 14 carbon atoms. More preferably, phenyl, naphthyl, indenyl, and the like can be mentioned.

Moreover, the phenyl group may be condensed with a 5- to 8-membered cycloalkyl ring to form indanyl or tetrahydronaphthyl group.

The aryl moiety of the "arylene group" in the present invention is as defined for the above-mentioned aryl group.

The aryl moiety of the "aryloxy group" in the present invention is as defined for the above-mentioned aryl group.

The aryl moiety of the "arylcarbonyl group" in the present invention is as defined for the above-mentioned aryl group.

The "aralkyl group" in the present invention means an arylalkyl group, wherein the aryl moiety and the alkyl moiety are as defined for the above-mentioned aryl group and the above-mentioned alkyl group, respectively. For example, a $C_{7-10}$ aralkyl group such as benzyl, phenethyl and the like, and the like can be mentioned.

As the "heteroaryl group" in the present invention, a 5- to 8-membered, monocyclic to tricyclic aromatic heterocyclic group containing, as ring atom(s) besides carbon atom(s), 1 to 4 heteroatoms selected from an oxygen atom, a sulfur atom, and a nitrogen atom can be mentioned, wherein a sulfur atom or a nitrogen atom may be oxidized to form an oxide. Preferably, pyridyl, pyridazinyl, pyrimidyl, pyrazinyl, furyl, thienyl, pyrrolyl, isoxazolyl, oxazolyl, isothiazolyl, thiazolyl, pyrazolyl, imidazolyl, oxadiazolyl, thiadiazolyl, triazolyl, tetrazolyl, benzofuranyl, benzothienyl, indolyl, isoindolyl, benzoxazolyl, benzothiazolyl, benzimidazolyl, indazolyl, benzisoxazolyl, benzisothiazolyl, benzofurazanyl, benzothiadiazolyl, purinyl, quinolyl, isoquinolyl, cinnolinyl, phthalazinyl, quinazolinyl, quinoxalinyl, pteridinyl, imidazoxazolyl, imidazothiazolyl, imidazoimidazolyl, dibenzofuranyl, dibenzothienyl, carbazolyl, acridinyl, and the like can be mentioned.

The heteroaryl moiety of the "heteroarylene group" in the present invention is as defined for the above-mentioned heteroaryl group.

The heteroaryl moiety of the "heteroaryloxy group" in the present invention is as defined for the above-mentioned heteroaryl group.

The heteroaryl moiety of the "heteroarylcarbonyl group" in the present invention is as defined for the above-mentioned heteroaryl group.

As the "heterocyclic group" in the present invention, a 5- to 8-membered, monocyclic to tricyclic heterocyclic group containing, as ring atom(s) besides carbon atom(s), 1 to 4 heteroatoms selected from an oxygen atom, a sulfur atom, and a nitrogen atom can be mentioned, wherein any carbon atom, which is a ring atom, may be substituted by an oxo group, and a sulfur atom or a nitrogen atom may be oxidized to form oxide. In addition, the heterocyclic group may be condensed with a benzene ring, may be crosslinked, and may form a spiro ring. Preferably, pyridyl, pyridazinyl, pyrimidyl, pyrazinyl, furyl, thienyl, pyrrolyl, isoxazolyl, oxazolyl, isothiazolyl, thiazolyl, pyrazolyl, imidazolyl, oxadiazolyl, thiadiazolyl, triazolyl, tetrazolyl, benzofuranyl, benzothienyl, indolyl, isoindolyl, benzoxazolyl, benzothiazolyl, benzimidazolyl, indazolyl, benzisoxazolyl, benzisothiazolyl, benzofurazanyl, benzothiadiazolyl, purinyl, quinolyl, isoquinolyl, cinnolinyl, phthalazinyl, quinazolinyl, quinoxalinyl, pteridinyl, imidazoxazolyl, imidazothiazolyl, imidazimidazolyl, dibenzofuranyl, dibenzothienyl, carbazolyl, acridinyl, pyrrolidinyl, pyrazolidinyl, imidazolidinyl, pyrrolinyl, pyrazolinyl, imidazolinyl, tetrahydrofuranyl, tetrahydrothiophenyl, thiazolidinyl, piperidinyl, piperazinyl, quinuclidinyl, tetrahydropyranyl, morpholinyl, dioxolanyl, homopiperidinyl, homopiperazinyl, indolinyl, isoindolinyl, chromanyl, isochromanyl, 8-azabicyclo[3.2.1]octan-3-yl, 9-azabicyclo[3.3.1]nonan-3-yl, 3-azabicyclo[3.2.1]octan-6- yl, 7-azabicyclo[2.2.1]heptan-2-yl, 2-azatricyclo[3.3.1.1]decan-4-yl, 1-azabicyclo[2.2.2]octan-2-yl, 1-azabicyclo[2.2.2]octan-3-yl, 1-azabicyclo[2.2.2]octan-4-yl, 3-azaspiro[5.5]undecan-9-yl, 2-azaspiro[4.5]decan-8-yl, 2-azaspiro[4.4]nonan-7-yl, 8-azaspiro[4.5]decan-2-yl, and the like can be mentioned.

The heterocyclic moiety of the "heterocyclylene group" in the present invention is as defined for the above-mentioned heterocyclic group.

The alkyl moiety of the "alkylthio group" in the present invention is as defined for the above-mentioned alkyl group.

The aryl moiety of the "arylthio group" in the present invention is as defined for the above-mentioned aryl group.

The heteroaryl moiety of the "heteroarylthio group" in the present invention is as defined for the above-mentioned heteroaryl group.

The "alkanoyl group" in the present invention refers to an aliphatic acyl group and, for example, a $C_{1-6}$ alkanoyl group such as formyl, acetyl, propionyl, butyryl, isobutyryl, valeryl, isovaleryl, pivaloyl, hexanoyl, and the like, and the like can be mentioned.

The alkanoyl moiety of the "alkanoyloxy group" in the present invention is as defined for the above-mentioned alkanoyl group.

As the "alkylamino group" in the present invention, an alkylamino group wherein one hydrogen atom of the amino group is substituted by the above-mentioned alkyl group can be mentioned. As the "dialkylamino group" in the present invention, a dialkylamino group wherein two hydrogen atoms of the amino group are substituted by the above-mentioned alkyl groups can be mentioned.

As the "cycloalkylamino group" in the present invention, a cycloalkylamino group wherein one hydrogen atom of the amino group is substituted by the above-mentioned cycloalkyl group can be mentioned. As the "dicycloalkylamino group" in the present invention, a dicycloalkylamino group wherein two hydrogen atoms of the amino group are substituted by the above-mentioned cycloalkyl groups can be mentioned.

As the "arylamino group" in the present invention, an arylamino group wherein one hydrogen atom of the amino group is substituted by the above-mentioned aryl group can be mentioned.

As the "heteroarylamino group" in the present invention, a heteroarylamino group wherein one hydrogen atom of the amino group is substituted by the above-mentioned heteroaryl group can be mentioned.

As the "carboxylic acid ester group" in the present invention, for example, an alkoxycarbonyl group, an aryloxycarbonyl group, an aralkyloxycarbonyl group, and the like can be mentioned. The alkoxy moiety, aryl moiety and aralkyl moiety of these are as defined for the above-mentioned "alkoxy group," "aryl group," and "aralkyl group," respectively. For example, methoxycarbonyl, ethoxycarbonyl, phenoxycarbonyl, benzyloxycarbonyl, and the like can be mentioned.

As the "phosphoric acid diester group" in the present invention, for example, a dialkoxyphosphono group, a diaryloxyphosphono group, a diaralkyloxyphosphono group, and the like can be mentioned.

As the "phosphoric acid monoester group" in the present invention, for example, an alkoxy-hydroxy-phosphono group, an aryloxy-hydroxy-phosphono group, an aralkyloxy-hydroxy-phosphono group, and the like can be mentioned.

The alkoxy moiety, the aryl moiety and the aralkyl moiety of these are as defined for the above-mentioned "alkoxy group," "aryl group," and "aralkyl group," respectively.

The "halogen atom" in the present invention refers to each atom of fluorine, chlorine, bromine, and iodine.

As the "lower alkylene group" in the present invention, for example, a straight or branched chain $C_{1-6}$ alkylene group such as methylene, ethylene, propylene, butylene, pentamethylene, hexamethylene, and the like, and the like can be mentioned.

As the "lower alkenylene group" in the present invention, for example, a straight or branched chain $C_{2-6}$ alkenylene group such as vinylene, propenylene, 1-butenylene, 2-butenylene, 1-pentenylene, 2-pentenylene, 3-pentenylene, 1-hexenylene, and the like, and the like can be mentioned.

As the "lower alkynylene group" in the present invention, for example, a straight or branched chain $C_{2-6}$ alkynylene group such as ethynylene, propynylene, 1-butynylene, 2-butynylene, 1-pentynylene, 2-pentynylene, 3-pentynylene, 1-hexynylene, and the like, and the like can be mentioned.

As the "3- to 8-membered ring formed by R5 and R6 together with the carbon atom bonded thereto" in the present invention, for example, a saturated or unsaturated hydrocarbon ring such as a cycloalkane (e.g., cyclopropane, cyclobutane, cyclopentane, cyclohexane, cycloheptane, cyclooctane, etc.), a cycloalkene (e.g., cyclopropene, cyclobutene, cyclopentene, cyclohexene, cycloheptene, cyclooctene, etc.), and the like, and a saturated or unsaturated heterocycle further containing, besides carbon atom(s), a nitrogen atom, an oxygen atom or a sulfur atom, such as pyrrolidine, tetrahydrofuran, tetrahydrothiophene, piperidine, morpholine, thiomorpholine, piperazine, and the like can be mentioned.

The "amino-protecting group" of "amino group optionally substituted by amino-protecting group(s)" in the present invention refers to a protecting group generally used for protecting an amino group from various reactions. For example, an acyl group such as a formyl group, an acetyl group, a trifluoroacetyl group, a pivaloyl group, and the like; an alkoxycarbonyl group such as a methoxycarbonyl group, a ethoxycarbonyl group, a tert-butoxycarbonyl group, a (fluoren-9-yl)methoxycarbonyl group, and the like; and the like can be mentioned.

As the substituent of the substituted alkyl group (including lower alkyl group), substituted alkoxy group and substituted alkanoyl group in the present invention, for example, a lower alkyl group, a lower alkoxy group, a lower alkoxycarbonyl group, a hydroxy group, a halogen atom, an amino group, a thio group, a lower alkylamino group, a lower alkylthio group, a carboxyl group, a nitro group, a cyano group, an amido group, an aryl group, a substituted aryl group, a heterocyclic group, a substituted heterocyclic group, a group represented by the following formula III:

$$Z\text{-}Y\text{---}X\text{---} \qquad \text{formula III}$$

wherein X and Y may be the same or different and each is any of a substituted or unsubstituted lower alkylene group, a substituted or unsubstituted lower alkenylene group, a substituted or unsubstituted lower alkynylene group, a substituted or unsubstituted cycloalkylene group, a substituted or unsubstituted arylene group, a substituted or unsubstituted heteroarylene group, a substituted or unsubstituted heterocyclylene group, a carbonyl group, an oxygen atom, a sulfur atom, a sulfinyl group, a sulfonyl group, a substituted or unsubstituted amino group, and a bond, and Z is any of a substituted or unsubstituted alkyl group, a substituted or unsubstituted alkenyl group, a substituted or unsubstituted alkynyl group, a substituted or unsubstituted alkanoyl group, a substituted or unsubstituted aryl group, a substituted or unsubstituted heteroaryl group, a substituted or unsubstituted heterocyclic group, a substituted or unsubstituted alkoxy group, a substituted or unsubstituted aryloxy group, a substituted or unsubstituted heteroaryloxy group, a substituted or unsubstituted alkylthio group, a substituted or unsubstituted arylthio group, a substituted or unsubstituted heteroarylthio group, a substituted or unsubstituted alkylamino group, a substituted or unsubstituted dialkylamino group, a substituted or unsubstituted cycloalkylamino group, a substituted or unsubstituted dicycloalkylamino group, a substituted or unsubstituted arylamino group, a substituted or unsubstituted heteroarylamino group, and a substituted or unsubstituted carbamoyl group, wherein the substituent of the group for Z is any of a lower alkyl group, a carboxyl group, a carboxylic acid ester group, a substituted or unsubstituted alkanoyloxy group, a substituted or unsubstituted carbamoyl group, a cyano group, a hydroxyl group, a sulfonic acid group, a sulfonamido group, a phosphoric acid group, a phosphoric acid monoester group, a phosphoric acid diester group, an amino group optionally substituted by amino-protecting group(s), a thiol group, a halogen atom, a substituted or unsubstituted aryl group, a substituted or unsubstituted heteroaryl group, a substituted or unsubstituted heterocyclic group, a substituted or unsubstituted alkanoyl group, a substituted or unsubstituted arylcarbonyl group, and a substituted or unsubstituted heteroarylcarbonyl group, and the group for Z optionally has the same or different multiple substituents selected from the substituents, and the like can be mentioned.

The lower alkyl, lower alkoxy, aryl and heterocyclic group here are as defined above, respectively. In addition, each group for each symbol in formula III is also as defined above.

The number of the substituents of the substituted alkyl group, substituted alkoxy group and substituted alkanoyl group is preferably 1 to 3, and when multiple substituents are used, they may be the same or different.

As the substituent of the substituted alkenyl group or substituted alkynyl group in the present invention, a substituted or unsubstituted lower alkyl group, a substituted or unsubstituted aryl group, a substituted or unsubstituted heteroaryl group, a carboxyl group, a carboxylic acid ester group, an amido group, a nitro group, a cyano group, a halogen atom, a hydroxyl group, a group represented by the following formula III:

Z-Y—X—                         formula III wherein each symbol is as defined above, and the like can be mentioned.

The lower alkyl group, aryl group, heteroaryl group, carboxylic acid ester group, and halogen atom here are as defined above.

The number of the substituents of the substituted alkenyl group and the substituted alkynyl group is preferably 1 to 3, and when multiple substituents are used, they may be the same or different.

As the substituent of the substituted cycloalkyl group, the substituted cycloalkenyl group, the substituted aryl group, the substituted heteroaryl group, and the substituted heterocyclic group in the present invention, for example, a substituted or unsubstituted lower alkyl group, a substituted or unsubstituted lower alkenyl group, a substituted or unsubstituted lower alkynyl group, a substituted or unsubstituted lower alkoxy group, a substituted or unsubstituted lower alkylthio group, a substituted or unsubstituted lower alkylsulfinyl group, a substituted or unsubstituted lower alkylsulfonyl group, a substituted or unsubstituted lower alkylamino group, a substituted or unsubstituted lower alkanoyl group, a halogen atom, a carboxyl group, a substituted or unsubstituted lower alkoxycarbonyl group, a hydroxyl group, a nitro group, a substituted or unsubstituted amino group, a cyano group, a substituted or unsubstituted amido group, a group represented by the following formula III:

Z-Y—X—                         formula III wherein each symbol is as defined above, and the like can be mentioned.

The number of the substituents of the substituted cycloalkyl group, the substituted cycloalkenyl group, the substituted aryl group, the substituted heteroaryl group, and the substituted heterocyclic group is preferably 1 to 6, and when multiple substituents are used, they may be the same or different.

As the substituent of the substituted lower alkylene group, the substituted lower alkenylene group, and the substituted lower alkynylene group in the present invention, a substituted or unsubstituted lower alkyl group, a substituted or unsubstituted aryl group, a substituted or unsubstituted heteroaryl group, a carboxyl group, a carboxylic acid ester group, an amido group, a nitro group, a cyano group, a halogen atom, a hydroxyl group, and the like can be mentioned. The lower alkyl group, aryl group, heteroaryl group, carboxylic acid ester group, and halogen atom here are as defined above.

The number of the substituents of the substituted lower alkylene group, the substituted lower alkenylene group, and the substituted lower alkynylene group is preferably 1 to 3, and when multiple substituents are used, they may be the same or different.

The substituents and the number thereof of the substituted alkyl moiety (including lower alkyl moiety) of the substituted alkylthio group (including lower alkylthio group), the substituted alkylamino group, the substituted dialkylamino group, and the substituted aralkyl group in the present invention are as defined with regard to the above-mentioned substituted alkyl group. In addition, the substituents and the number thereof of the substituted cycloalkyl moiety, substituted aryl moiety, and substituted heteroaryl moiety of the substituted cycloalkylamino group, the substituted dicycloalkylamino group, the substituted aralkyl group, the substituted arylamino group, the substituted aryloxy group, the substituted arylthio group, the substituted heteroaryloxy group, the substituted heteroarylthio group, and the substituted heteroarylamino group are as defined with regard to the above-mentioned substituted cycloalkyl group.

As the substituted carboxylic acid ester group in the present invention, a substituted alkoxycarbonyl group, a substituted aryloxycarbonyl group, a substituted aralkyloxycarbonyl group, and the like can be mentioned. The substituents and the number thereof of the substituted alkoxy moiety of the substituted alkoxycarbonyl group are as defined with regard to the above-mentioned substituted alkoxy group. The substituents and the number thereof of the substituted aryl moiety of the substituted aryloxycarbonyl group and the substituted aralkyloxycarbonyl group are as defined with regard to the above-mentioned substituted aryl group. The substituents and the number thereof of the substituted alkyl moiety of the substituted aralkyloxycarbonyl group are as defined with regard to the above-mentioned substituted alkyl group.

The substituent of the substituted methylene group in the present invention is as defined with regard to the above-mentioned substituted alkylene group. The number of substituents of these groups is 1 or 2.

As the substituent of the substituted carbamoyl group in the present invention, for example, a substituted or unsubstituted alkyl group, a substituted or unsubstituted aryl group, a substituted or unsubstituted heteroaryl group, a substituted or unsubstituted aralkyl group, or an alkyl group substituted by a substituted or unsubstituted heteroaryl group, and the like can be mentioned. Here, the alkyl group, aryl group, heteroaryl group, aralkyl group, and substituent thereof are as defined above.

As ring A in formula I, ring-1, ring-2, and ring-6 are preferable. Of these, ring-1 and ring-2 are particularly preferable.

As R1 in formula I, a substituted or unsubstituted alkyl group, a substituted or unsubstituted cycloalkyl group, a substituted or unsubstituted cycloalkenyl group, a substituted or unsubstituted aryl group, a substituted or unsubstituted heteroaryl group, a substituted or unsubstituted heterocyclic group, and a substituted or unsubstituted aralkyl group are preferable. Of these, a substituted or unsubstituted aryl group (particularly a substituted or unsubstituted phenyl group) and a substituted or unsubstituted heteroaryl group are particularly preferable.

As the substituent of the group for R1 in formula I, a cyano group, a hydroxyl group and a group represented by the following formula III:

Z-Y—X—  formula III wherein each symbol is as defined above, are preferable.

As X in formula III, a substituted or unsubstituted lower alkylene group, a substituted or unsubstituted lower alkenylene group, an oxygen atom, a substituted or unsubstituted amino group, a sulfur atom, and a bond are preferable. Of these, a substituted or unsubstituted methylene group, a substituted or unsubstituted ethylene group, a substituted or unsubstituted vinylene group, an oxygen atom, and a substituted or unsubstituted amino group are preferable, and a unsubstituted methylene group, a unsubstituted ethylene group, a unsubstituted vinylene group, an oxygen atom, and a unsubstituted amino group are particularly preferable.

As Y in formula III, a sulfur atom, a sulfinyl group, a sulfonyl group, an oxygen atom, a substituted or unsubstituted amino group, a substituted or unsubstituted lower alkylene group, a carbonyl group, and a bond are preferable. Of these, a sulfur atom, a sulfonyl group, an oxygen atom, a substituted or unsubstituted methylene group, a carbonyl group, and a bond are preferable; a sulfur atom, a sulfonyl group, a unsubstituted methylene group, a carbonyl group, and a bond are particularly preferable.

Those of ordinary skill in the art can understand possible combinations of X and Y in formula III and can make appropriate selection.

As Z in formula III, a substituted or unsubstituted alkyl group, a substituted or unsubstituted alkanoyl group, a substituted or unsubstituted aryl group, a substituted or unsubstituted heteroaryl group, and a substituted or unsubstituted heterocyclic group are preferable. Of these, a substituted methyl group, a substituted ethyl group, and a substituted propyl group are preferable.

As the substituent of the group for Z, a lower alkyl group, a carboxyl group, a carboxylic acid ester group, an alkanoyloxy group, an amino group optionally substituted by amino-protecting group(s) (including acetylamino group), a sulfonic acid group, and a hydroxyl group are preferable, and the number of the substituents is preferably 1 or 2.

As R2 in formula I, a hydrogen atom, a substituted or unsubstituted lower alkyl group, and a substituted or unsubstituted aralkyl group are preferable. Of these, a hydrogen atom is particularly preferable.

As R3 in formula I, a group represented by the following formula II:

 formula II wherein

R4 is any of a substituted or unsubstituted alkyl group, a substituted or unsubstituted cycloalkyl group, a substituted or unsubstituted cycloalkenyl group, a substituted or unsubstituted aryl group, a substituted or unsubstituted heteroaryl group, a substituted or unsubstituted heterocyclic group, a substituted or unsubstituted aralkyl group, a substituted or unsubstituted alkenyl group, a substituted or unsubstituted alkynyl group, a halogen atom, a substituted or unsubstituted alkoxy group, a substituted or unsubstituted aryloxy group, a substituted or unsubstituted heteroaryloxy group, a substituted or unsubstituted alkylthio group, a substituted or unsubstituted arylthio group, a substituted or unsubstituted heteroarylthio group, a substituted or unsubstituted alkylamino group, a substituted or unsubstituted dialkylamino group, a substituted or unsubstituted arylamino group, a substituted or unsubstituted heteroarylamino group, and an amino group optionally substituted by amino-protecting group(s), and R5 and R6 may be the same or different and each is any of a hydrogen atom and a substituted or unsubstituted lower alkyl group, or R5 and R6 optionally form, together with the carbon atom bonded thereto, a 3- to 8-membered ring, is preferable.

As R4 in formula II, a substituted or unsubstituted alkyl group, a substituted or unsubstituted cycloalkyl group, a substituted or unsubstituted cycloalkenyl group, a substituted or unsubstituted aryl group, a substituted or unsubstituted heteroaryl group, a substituted or unsubstituted heterocyclic group, a substituted or unsubstituted aralkyl group, a substituted or unsubstituted alkenyl group, a substituted or unsubstituted alkynyl group, and a halogen atom are preferable; a substituted or unsubstituted cycloalkenyl group, a substituted or unsubstituted aryl group, and a substituted or unsubstituted heteroaryl group are particularly preferable. Of these, a substituted phenyl group, a substituted cyclopentenyl group, a substituted cyclohexenyl group, and a substituted thienyl group are preferable, a substituted phenyl group, a substituted cyclopentenyl group and a substituted cyclohexenyl group are particularly preferable.

As the substituent of the group for R4, a halogen atom (particularly a chlorine atom, a bromine atom) and a substituted or unsubstituted lower alkyl group are preferable, and a chlorine atom and a bromine atom are particularly preferable.

As R5 in formula II, a hydrogen atom and a substituted or unsubstituted lower alkyl group are preferable. Of these, a substituted or unsubstituted lower alkyl group (particularly a methyl group) is particularly preferable.

As R6 in formula II, a hydrogen atom and a substituted or unsubstituted lower alkyl group are preferable. Of these, a hydrogen atom is particularly preferable.

As the compound of the present invention represented by formula I (hereinafter to be simply referred to as the compound of the present invention), the following compounds are preferable.

(Compound A-1)

In formula I, a compound wherein
R1 is as defined above,
R2 is any of a hydrogen atom, a substituted or unsubstituted lower alkyl group, a substituted or unsubstituted aralkyl group, and a hydroxyl group, and
R3 is a group represented by the following formula II:

formula II wherein
R4 is any of a substituted or unsubstituted alkyl group, a substituted or unsubstituted cycloalkyl group, a substituted or unsubstituted cycloalkenyl group, a substituted or unsubstituted aryl group, a substituted or unsubstituted heteroaryl group, a substituted or unsubstituted heterocyclic group, a substituted or unsubstituted aralkyl group, a substituted or unsubstituted alkenyl group, a substituted or unsubstituted alkynyl group, a halogen atom, a substituted or unsubstituted alkoxy group, a substituted or unsubstituted aryloxy group, a substituted or unsubstituted heteroaryloxy group, a substituted or unsubstituted alkylthio group, a substituted or unsubstituted arylthio group, a substituted or unsubstituted heteroarylthio group, a substituted or unsubstituted alkylamino group, a substituted or unsubstituted dialkylamino group, a substituted or unsubstituted arylamino group, a substituted or unsubstituted heteroarylamino group, and an amino group optionally substituted by amino-protecting group(s), and
R5 and R6 may be the same or different and each is any of a hydrogen atom and a substituted or unsubstituted lower alkyl group, or R5 and R6 optionally form, together with the carbon atom bonded thereto, a 3- to 8-membered ring.

Of the compounds A-1, the following Compound A-2 is preferable.

(Compound A-2)

A compound wherein the substituent of the group for R1 is any of a cyano group and a group represented by the following formula III:

Z-Y—X—  formula III wherein each symbol is as defined above,
R2 is any of a hydrogen atom, a substituted or unsubstituted lower alkyl group, and a substituted or unsubstituted aralkyl group,
R4 is any of a substituted or unsubstituted alkyl group, a substituted or unsubstituted cycloalkyl group, a substituted or unsubstituted cycloalkenyl group, a substituted or unsubstituted aryl group, a substituted or unsubstituted heteroaryl group, a substituted or unsubstituted heterocyclic group, a substituted or unsubstituted aralkyl group, a substituted or unsubstituted alkenyl group, a substituted or unsubstituted alkynyl group, and a halogen atom, and
R5 and R6 may be the same or different and each is any of a hydrogen atom and a substituted or unsubstituted lower alkyl group.

Of compounds A-2, the following Compound A-3 is preferable.

(Compound A-3)

A compound wherein

R1 is any of a substituted or unsubstituted alkyl group, a substituted or unsubstituted cycloalkyl group, a substituted or unsubstituted aryl group, a substituted or unsubstituted heteroaryl group, a substituted or unsubstituted heterocyclic group, and a substituted or unsubstituted aralkyl group.

Of compounds A-2, the following Compound A-4 is also preferable.

(Compound A-4)

A compound wherein

R1 is any of a substituted or unsubstituted aryl group, a substituted or unsubstituted heteroaryl group, a substituted or unsubstituted heterocyclic group, a substituted or unsubstituted cycloalkyl group, and a substituted or unsubstituted cycloalkenyl group,
wherein the substituent of the group for R1 is a group represented by the following formula III:

Z-Y—X—  formula III wherein each symbol is as defined above,
R2 is a hydrogen atom,
R4 is any of a substituted or unsubstituted aryl group, a substituted or unsubstituted heteroaryl group, a substituted or unsubstituted heterocyclic group, a substituted or unsubstituted cycloalkyl group, and a substituted or unsubstituted cycloalkenyl group,
R5 is a substituted or unsubstituted lower alkyl group, and
R6 is a hydrogen atom.

Of compounds A-4, the following Compound A-5 is preferable.

(Compound A-5)

A compound wherein R4 is a substituted or unsubstituted cycloalkenyl group.

Of compounds A-4, the following Compound A-6 is also preferable.

(Compound A-6)

A compound wherein ring A is any of ring-1 and ring-2,
R1 is a substituted phenyl group,
X is any of a substituted or unsubstituted methylene group, a substituted or unsubstituted ethylene group, and a substituted or unsubstituted vinylene group,
Y is any of a sulfur atom, a sulfonyl group, a substituted or unsubstituted methylene group, and an oxygen atom,
Z is any of a substituted methyl group, a substituted ethyl group, a substituted propyl group, and a substituted carbamoyl group,
wherein the substituent of the group for Z is any of a carboxyl group, a carboxylic acid ester group, an acetylamino group, a sulfonic acid group, and a hydroxyl group, and the group for Z optionally has multiple substituents selected from the substituents,
R4 is any of a substituted phenyl group, a substituted cyclopentenyl group, a substituted cyclohexenyl group, and a substituted thienyl group, wherein the substituent of the group for R4 is any of a chlorine atom, a bromine atom, and a substituted or unsubstituted lower alkyl group, and R5 is a methyl group.

Of compounds Compound A-6, the following Compound A-7 is preferable.

(Compound A-7)

A compound wherein

X is any of a methylene group, a ethylene group, and a vinylene group,

Y is any of a sulfur atom, a sulfonyl group, a methylene group, and an oxygen atom, Z is any of a substituted methyl group, a substituted ethyl group, a substituted propyl group, and a substituted carbamoyl group, wherein the substituent of the group for Z is any of a carboxyl group, a carboxylic acid ester group, an acetylamino group, and a sulfonic acid group, and the group for Z optionally has multiple substituents selected from the substituents, R4 is any of a substituted phenyl group, a substituted cyclopentenyl group, and a substituted cyclohexenyl group, wherein the substituent of the group for R4 is any of a chlorine atom and a bromine atom.

As the compound of the present invention, the following Compound B-1 is also preferable.

(Compound B-1)

In formula I, a compound wherein

R1 is any of a substituted or unsubstituted alkyl group, a substituted or unsubstituted cycloalkyl group, a substituted or unsubstituted aryl group, a substituted or unsubstituted heteroaryl group, a substituted or unsubstituted heterocyclic group, a substituted or unsubstituted aralkyl group, a substituted or unsubstituted alkenyl group, a substituted or unsubstituted alkynyl group, a halogen atom, a substituted or unsubstituted alkoxy group, a substituted or unsubstituted aryloxy group, a substituted or unsubstituted heteroaryloxy group, a substituted or unsubstituted alkylthio group, a substituted or unsubstituted arylthio group, a substituted or unsubstituted heteroarylthio group, a substituted or unsubstituted alkylamino group, a substituted or unsubstituted dialkylamino group, a substituted or unsubstituted cycloalkylamino group, a substituted or unsubstituted dicycloalkylamino group, a substituted or unsubstituted arylamino group, a substituted or unsubstituted heteroarylamino group, a substituted or unsubstituted alkanoyl group, a substituted or unsubstituted carboxylic acid ester group, a substituted or unsubstituted carbamoyl group, and an amino group optionally substituted by amino-protecting group(s), and R4 is any of a substituted or unsubstituted alkyl group, a substituted or unsubstituted cycloalkyl group, a substituted or unsubstituted aryl group, a substituted or unsubstituted heteroaryl group, a substituted or unsubstituted heterocyclic group, a substituted or unsubstituted aralkyl group, a substituted or unsubstituted alkenyl group, a substituted or unsubstituted alkynyl group, a halogen atom, a substituted or unsubstituted alkoxy group, a substituted or unsubstituted aryloxy group, a substituted or unsubstituted heteroaryloxy group, a substituted or unsubstituted alkylthio group, a substituted or unsubstituted arylthio group, a substituted or unsubstituted heteroarylthio group, a substituted or unsubstituted alkylamino group, a substituted or unsubstituted dialkylamino group, a substituted or unsubstituted cycloalkylamino group, a substituted or unsubstituted dicycloalkylamino group, a substituted or unsubstituted arylamino group, a substituted or unsubstituted heteroarylamino group, and an amino group optionally substituted by amino-protecting group(s).

Of Compounds B-1, the following Compound B-2 is preferable.

(Compound B-2)

A compound wherein

R1 is a substituted phenyl group, wherein the substituent of the group for R1 is any of a cyano group and a group represented by the following formula III:

$$Z\text{-}Y\text{---}X\text{---} \qquad \text{formula III}$$

wherein

X is any of a methylene group and an ethylene group,

Y is any of a sulfur atom, a sulfinyl group, a sulfonyl group, an oxygen atom, a substituted or unsubstituted amino group, and a methylene group, and Z is any of a substituted or unsubstituted lower alkyl group, a substituted or unsubstituted lower alkenyl group, a substituted or unsubstituted alkanoyl group, a substituted or unsubstituted triazole group, and a substituted or unsubstituted tetrazole group, wherein the substituent of the group for Z is any of a carboxyl group, an alkoxycarbonyl group, a furyl group, a phenyl group, a hydroxyl group, a carbamoyl group, a carbamoyl group substituted by lower alkyl group(s), a carbamoyl group substituted by carboxy lower alkyl group(s), a carbamoyl group substituted by lower alkyl group(s) substituted by a furyl group, an amino group optionally substituted by amino-protecting group(s), a sulfonic acid group, a pyrrolylcarbonyl group, a pyridyl group, and a halogen atom, and the group for Z optionally has the same or different multiple substituents selected from the substituents, R2 is a hydrogen atom, R3 is a group represented by the following formula II:

formula II wherein

R4 is a substituted or unsubstituted phenyl group, wherein the substituent of the group for R4 is a halogen atom, R5 is any of a hydrogen atom, a lower alkyl group, and a lower alkyl group substituted by 1 to 3 halogen atoms, and R6 is a hydrogen atom.

Of compounds A-1, the following Compound B-3 is also preferable.

(Compound B-3)

A compound wherein

R1 is any of a substituted or unsubstituted alkyl group, a substituted or unsubstituted cycloalkyl group, a substituted or unsubstituted aryl group, a substituted or unsubstituted heteroaryl group, a substituted or unsubstituted heterocyclic group, a substituted or unsubstituted aralkyl group, a substituted or unsubstituted alkenyl group, a substituted or unsubstituted alkynyl group, a halogen atom, a substituted or unsubstituted alkoxy group, a substituted or unsubstituted aryloxy group, a substituted or unsubstituted heteroaryloxy group, a substituted or unsubstituted alkylthio group, a substituted or unsubstituted arylthio group, a substituted or unsubstituted heteroarylthio group, a substituted or unsubstituted alkylamino group, a substituted or unsubstituted dialkylamino group, a substituted or unsubstituted cycloalkylamino group, a substituted or unsubstituted dicycloalkylamino group, a substituted or unsubstituted arylamino group, a substituted or unsubstituted heteroarylamino group, a substituted or unsubstituted alkanoyl group, a substituted or unsubstituted carboxylic acid ester group, a substituted or unsubstituted carbamoyl group, and an amino group optionally substituted by amino-protecting group(s), R4 is any of a substituted or unsubstituted alkyl group, a substituted or unsubstituted cycloalkyl group, a substituted or unsubstituted aryl group, a substituted or unsubstituted heteroaryl group, a substituted or unsubstituted heterocyclic group, a substituted or unsubstituted aralkyl group, a substituted or unsubstituted alkenyl group, a substituted or unsubstituted alkynyl group, a halogen atom, a substituted or unsubstituted alkoxy group, a substituted or unsubstituted aryloxy group, a substituted or unsubstituted heteroaryloxy group, a substituted or unsubstituted alkylthio group, a substituted or unsubstituted arylthio group, a substituted or unsubstituted heteroarylthio group, a substituted or unsubstituted alkylamino group, a substituted or unsubstituted dialkylamino group, a substituted or unsubstituted arylamino group, a substituted or unsubstituted heteroarylamino group, and an amino group optionally substituted by amino-protecting group(s).

Of compounds A-2, the following Compound B-4 is preferable.

(Compound B-4)

In formula I, a compound wherein

R1 is any of a substituted or unsubstituted alkyl group, a substituted or unsubstituted cycloalkyl group, a substituted or unsubstituted aryl group, a substituted or unsubstituted heteroaryl group, a substituted or unsubstituted heterocyclic group, a substituted or unsubstituted aralkyl group, a substituted or unsubstituted alkenyl group, a substituted or unsubstituted alkynyl group, a halogen atom, a substituted or unsubstituted alkoxy group, a substituted or unsubstituted aryloxy group, a substituted or unsubstituted heteroaryloxy group, a substituted or unsubstituted alkylthio group, a substituted or unsubstituted arylthio group, a substituted or unsubstituted heteroarylthio group, a substituted or unsubstituted alkylamino group, a substituted or unsubstituted dialkylamino group, a substituted or unsubstituted cycloalkylamino group, a substituted or unsubstituted dicycloalkylamino group, a substituted or unsubstituted arylamino group, a substituted or unsubstituted heteroarylamino group, a substituted or unsubstituted alkanoyl group, a substituted or unsubstituted carboxylic acid ester group, a substituted or unsubstituted carbamoyl group, and an amino group optionally substituted by amino-protecting group(s), and R4 is any of a substituted or unsubstituted alkyl group, a substituted or unsubstituted cycloalkyl group, a substituted or unsubstituted aryl group, a substituted or unsubstituted heteroaryl group, a substituted or unsubstituted heterocyclic group, a substituted or unsubstituted aralkyl group, a substituted or unsubstituted alkenyl group, a substituted or unsubstituted alkynyl group, and a halogen atom.

Of compounds B-4, the following Compound B-5 is preferable.

(Compound B-5)

A compound wherein

R1 is any of a substituted or unsubstituted alkyl group, a substituted or unsubstituted cycloalkyl group, a substituted or unsubstituted aryl group, a substituted or unsubstituted heteroaryl group, a substituted or unsubstituted heterocyclic group, and a substituted or unsubstituted aralkyl group.

Of compounds A-1, the following Compound C-1 is preferable.

(Compound C-1)

In formula I, a compound wherein the substituent of the group for R1 is any of a hydroxyl group and a group represented by the following formula III:

$$Z-Y-X-\qquad \text{formula III}$$

wherein

X is any of an oxygen atom, a substituted or unsubstituted amino group, a sulfur atom, and a bond, Y is any of a carbonyl group, a sulfonyl group, and a bond, and Z is any of a substituted or unsubstituted alkyl group, a substituted or unsubstituted alkenyl group, a substituted or unsubstituted alkynyl group, a substituted or unsubstituted alkanoyl group, a substituted or unsubstituted aryl group, a substituted or unsubstituted heteroaryl group, a substituted or unsubstituted heterocyclic group, a substituted or unsubstituted alkoxy group, a substituted or unsubstituted aryloxy group, a substituted or unsubstituted heteroaryloxy group, a substituted or unsubstituted alkylthio group, a substituted or unsubstituted arylthio group, a substituted or unsubstituted heteroarylthio group, a substituted or unsubstituted alkylamino group, a substituted or unsubstituted dialkylamino group, a substituted or unsubstituted cycloalkylamino group, a substituted or unsubstituted dicycloalkylamino group, a substituted or unsubstituted arylamino group, and a substituted or unsubstituted heteroarylamino group, wherein the substituent of the group for Z is any of a lower alkyl group, a carboxyl group, a carboxylic acid ester group, a substituted or unsubstituted alkanoyloxy group, a substituted or unsubstituted carbamoyl group, a cyano group, a hydroxyl group, a sulfonic acid group, a sulfonamido group, a phosphoric acid group, a phosphoric acid monoester group, a phosphoric acid diester group, an amino group optionally substituted by amino-protecting group(s), a thiol group, a halogen atom, a substituted or unsubstituted aryl group, a substituted or unsubstituted heteroaryl group, a substituted or unsubstituted heterocyclic group, a substituted or unsubstituted alkanoyl group, a substituted or unsubstituted arylcarbonyl group, and a substituted or unsubstituted heteroarylcarbonyl group, and the group for Z optionally has the same or different multiple substituents selected from the substituents, R2 is any of a hydrogen atom, a substituted or unsubstituted lower alkyl group, and a substituted or unsubstituted aralkyl group, R4 is any of a substituted or unsubstituted alkyl group, a substituted or unsubstituted cycloalkyl group, a substituted or unsubstituted cycloalkenyl group, a substituted or unsubstituted aryl group, a substituted or unsubstituted heteroaryl group, a substituted or unsubstituted heterocyclic group, a substituted or unsubstituted aralkyl group, a substituted or unsubstituted alkenyl group, a substituted or unsubstituted alkynyl group, and a halogen atom, and R5 and R6 may be the same or different and each is any of a hydrogen atom and a substituted or unsubstituted lower alkyl group.

Of compounds C-1, the following Compound C-2 is preferable.

(Compound C-2)

In formula I, a compound wherein

R1 is any of a substituted or unsubstituted phenyl group, a substituted or unsubstituted heteroaryl group, a substituted or unsubstituted heterocyclic group, a substituted or unsubstituted cycloalkyl group, and a substituted or unsubstituted cycloalkenyl group, wherein the substituent of the group for R1 is any of a hydroxyl group and a group represented by the following formula III:

Z-Y—X—  formula III wherein

X is any of an oxygen atom, a substituted or unsubstituted amino group, a sulfur atom, and a bond, Y is any of a carbonyl group, a sulfonyl group, and a bond, and Z is a substituted or unsubstituted alkyl group wherein the substituent of the group for Z is any of a lower alkyl group, a carboxyl group, a carboxylic acid ester group, a substituted or unsubstituted alkanoyloxy group, a substituted or unsubstituted carbamoyl group, a cyano group, a hydroxyl group, a sulfonic acid group, a sulfonamido group, a phosphoric acid group, a phosphoric acid monoester group, a phosphoric acid diester group, an amino group optionally substituted by amino-protecting group(s), a thiol group, a halogen atom, a substituted or unsubstituted aryl group, a substituted or unsubstituted heteroaryl group, a substituted or unsubstituted heterocyclic group, a substituted or unsubstituted alkanoyl group, a substituted or unsubstituted arylcarbonyl group, and a substituted or unsubstituted heteroarylcarbonyl group, and the group for Z optionally has the same or different multiple substituents selected from the substituents.

Of compounds C-2, the following Compound C-3 is preferable.

(Compound C-3)

In formula I, a compound wherein ring A is any of ring-1 and ring-2, and

R1 is a substituted phenyl group, wherein the substituent of the group for R1 is any of a hydroxyl group and a group represented by the following formula III:

Z-Y—X—  formula III wherein

X is any of an oxygen atom and a substituted or unsubstituted amino group,

Y is any of a carbonyl group and a bond, and

Z is a substituted or unsubstituted alkyl group, wherein the substituent of the group for Z is any of a lower alkyl group, a carboxyl group, a carboxylic acid ester group, a substituted or unsubstituted alkanoyloxy group, a substituted or unsubstituted carbamoyl group, a cyano group, a hydroxyl group, a sulfonic acid group, a sulfonamido group, a phosphoric acid group, a phosphoric acid monoester group, a phosphoric acid diester group, an amino group optionally substituted by amino-protecting group(s), a thiol group, a halogen atom, a substituted or unsubstituted aryl group, a substituted or unsubstituted heteroaryl group, a substituted or unsubstituted heterocyclic group, a substituted or unsubstituted alkanoyl group, a substituted or unsubstituted arylcarbonyl group, and a substituted or unsubstituted heteroarylcarbonyl group, and the group for Z optionally has the same or different multiple substituents selected from the substituents.

Of Compounds C-3, the following Compound C-4 is preferable.

(Compound C-4)

In formula I, a compound wherein the substituent of the group for R1 is any of a hydroxyl group and a group represented by the following formula III:

Z-Y—X—  formula III wherein

X is any of an oxygen atom and a substituted or unsubstituted amino group,

Y is any of a carbonyl group and a bond,

Z is a substituted or unsubstituted alkyl group, wherein the substituent of the group for Z is any of a lower alkyl group, a carboxyl group, a carboxylic acid ester group, alkanoyloxy group, a hydroxyl group, a sulfonic acid group, and an amino group optionally substituted by amino-protecting group(s), and the group for Z optionally has the same or different multiple substituents selected from the substituents.

Particularly preferable compound of the present invention is, methyl 3-(4-{4-[1-(2-chlorophenyl)ethoxycarbonylamino]-3-isoxazolyl}-benzylsulfanyl)propionate (Compound 1);

3-(4-{4-[1-(2-chlorophenyl)ethoxycarbonylamino]-3-isoxazolyl}benzylsulfanyl)propionic acid (Compound 2);

3-(4-{4-[(1R)-1-(2-chlorophenyl)ethoxycarbonylamino]-3-isoxazolyl}benzylsulfanyl)-propionic acid (Compound 3);

N-acetyl-S-(4-{4-[1-(2-chlorophenyl)ethoxycarbonylamino]-3-isoxazolyl}benzyl)-L-cysteine (Compound 4);

2-(4-{4-[1-(2-chlorophenyl)ethoxycarbonylamino]-3-isoxazolyl}benzylsulfanyl)-ethanesulfonic acid (Compound 5);

3-(4-{4-[(1R)-1-(2-bromophenyl)ethoxycarbonylamino]-3-isoxazolyl}benzylsulfanyl)-propionic acid (Compound 6);

N-acetyl-S-(4-{4-[(1R)-1-(2-bromophenyl)ethoxycarbonylamino]-3-isoxazolyl}benzyl)-L-cysteine (Compound 7);

3-(4-{4-[1-(2-chloro-1-cyclopentenyl)ethoxycarbonylamino]-3-isoxazolyl}-benzylsulfanyl)propionic acid (Compound 8);

3-(4-{4-[(1R)-1-(2-chloro-1-cyclopentenyl)ethoxycarbonylamino]-3-isoxazolyl}-benzylsulfanyl)propionic acid (Compound 9);

3-(4-{4-[1-(2-chloro-1-cyclohexenyl)ethoxycarbonylamino]-3-isoxazolyl}-benzylsulfanyl)propionic acid (Compound 10);

3-(4-{4-[1-(2-chlorophenyl)ethoxycarbonylamino]-3-isoxazolyl}benzylsulfonyl)-propionic acid (Compound 11);

3-(4-{4-[(1R)-1-(2-bromophenyl)ethoxycarbonylamino]-3-isoxazolyl}benzylsulfonyl)-propionic acid (Compound 12);

3-(4-{4-[1-(2-chloro-1-cyclohexenyl)ethoxycarbonylamino]-3-isoxazolyl}-benzylsulfonyl)propionic acid (Compound 13);

{[2-(4-{4-[1-(2-chlorophenyl)ethoxycarbonylamino]-3-isoxazolyl}phenyl)ethyl]thio}-acetic acid (Compound 14);

{3-[2-(4-{4-[1-(2-chlorophenyl)ethoxycarbonylamino]-3-isoxazolyl}phenyl)ethyl]thio}-propionic acid (Compound 15);

{[2-(4-{4-[1-(2-chlorocyclopentenyl)ethoxycarbonylamino]-3-isoxazolyl}-phenyl)ethyl]thio}acetic acid (Compound 16);

{[2-(4-{4-[1-(2-chlorocyclohexenyl)ethoxycarbonylamino]-3-isoxazolyl}-phenyl)ethyl]thio}acetic acid (Compound 17);

3-(4-{4-[1-(2-chlorophenyl)ethoxycarbonylamino]-5-isoxazolyl}benzylsulfanyl)propionic acid (Compound 18);

5-(4-{4-[1-(2-chlorophenyl)ethoxycarbonylamino]-3-isoxazolyl}phenyl)-4-pentanoic acid (Compound 19);

3-(4-{4-[1-(2-chlorophenyl)ethoxycarbonylamino]-3-isoxazolyl}-benzyloxycarbonylamino)propionic acid (Compound 20);

4-[(4-{4-[1-(2-chlorophenyl)ethoxycarbonylamino]-3-isoxazolyl}phenyl)amino]-(2R)-2-hydroxy-4-oxobutanoic acid (Compound 21);

4-[4-({[1-(2-chlorophenyl)ethoxy]carbonyl}amino)-3-isoxazolyl]phenyl acetate (Compound 22);

1-(2-chlorophenyl)ethyl 3-(4-hydroxyphenyl)-4-isoxazolylcarbamate (Compound 23);

5-(4-{4-[1-(2-chlorophenyl)ethoxycarbonylamino]-3-isoxazolyl}phenoxy)pentanoic acid (Compound 24);

4-[(4-{4-[1-(2-chlorophenyl)ethoxycarbonylamino]-3-isoxazolyl}phenyl)amino]-4-oxobutanoic acid (Compound 25);

(2R)-2-acetoxy-4-[(4-{4-[1-(2-chlorophenyl)ethoxycarbonylamino]-3-isoxazolyl}-phenyl)amino]-4-oxobutanoic acid (Compound 26);

{[2-(4-{4-[(1R)-1-(2-chlorophenyl)ethoxycarbonylamino]-3-isoxazolyl}-phenyl)ethyl]thio}acetic acid (Compound 27);

3-(4-{4-[(1R)-1-(2-chlorophenyl)ethoxycarbonylamino]-3-isoxazolyl}benzylsulfonyl)-propionic acid (Compound 28);

{3-[2-(4-{4-[(1R)-1-(2-chlorophenyl)ethoxycarbonylamino]-3-isoxazolyl}-phenyl)ethyl]thio}propionic acid (Compound 29);

5-(4-{4-[(1R)-1-(2-chlorophenyl)ethoxycarbonylamino]-3-isoxazolyl}phenyl)-4-pentenoic acid (Compound 30);

5-(4-{4-[(1R)-1-(2-chlorophenyl)ethoxycarbonylamino]-3-isoxazolyl}phenyl)-4-pentanoic acid (Compound 31);

6-(4-{4-[(1R)-1-(2-chlorophenyl)ethoxycarbonylamino]-3-isoxazolyl}phenyl)hexanoic acid (Compound 32);

5-(4-{4-[1-(2-chlorophenyl)ethoxycarbonylamino]-3-isoxazolyl}phenyl)-3,3-dimethylpentanoic acid (Compound 33); and 5-(4-{4-[(1R)-1-(2-chlorophenyl)ethoxycarbonylamino]-3-isoxazolyl}phenyl)-2-methylpentanoic acid (Compound 34)

can be mentioned.

When the compound of the present invention can form a salt, a pharmaceutically acceptable salt is preferable. As such pharmaceutically acceptable salt, for the acidic group in the formula, such as carboxyl group and the like, for example, an ammonium salt, salts with alkali metals such as sodium, potassium, and the like, salts with alkaline earth metals such as calcium, magnesium, and the like, aluminum salt, zinc salt, salts with organic amines such as triethylamine, ethanolamine, morpholine, pyrrolidine, piperidine, piperazine, dicyclohexylamine, and the like, and salts with basic amino acids such as arginine, lysine, and the like can be mentioned.

For the basic group when a basic group is present in formula I, salts with inorganic acids such as hydrochloric acid, sulfuric acid, phosphoric acid, nitric acid, hydrobromic acid, and the like, salts with organic carboxylic acids such as acetic acid, citric acid, benzoic acid, maleic acid, fumaric acid, tartaric acid, succinic acid, tannic acid, butyric acid, hibenzic acid, pamoic acid, enanthic acid, decanoic acid, teoclic acid, salicylic acid, lactic acid, oxalic acid, mandelic acid, malic acid, and the like, and salts with organic sulfonic acids such as methanesulfonic acid, benzenesulfonic acid, p-toluenesulfonic acid, and the like can be mentioned. As a method for forming a salt, mixing the compound of the present invention with a necessary acid or base at a suitable amount ratio in a solvent or dispersing agent, or cation exchange or anion exchange of a salt in other form is carried out.

The compound of the present invention includes solvates thereof, such as hydrates, alcohol addition products, and the like.

The compound of the present invention encompasses an optical isomer thereof, a stereoisomer thereof, a regioisomer thereof, a tautomer thereof, a rotational isomer thereof, and mixtures thereof at an optional ratio, when they are present. These can be each obtained as a single product by synthesis methods and separation methods known per se.

For example, an optical isomer can be obtained by the use of an optically active synthetic intermediate, or a racemate of the synthetic intermediate or the final product can be subjected to optical resolution according to a conventional method.

The compound of the present invention can be converted to a prodrug. In the present invention, the term prodrug means a compound that is converted in the body to produce the compound of the present invention. For example, when the active compound contains a carboxyl group or a phosphoric acid group, an ester thereof, an amide thereof, and the like can be mentioned, and when the active compound contains a carboxyl group, a group that is converted to a carboxyl group by oxidative metabolism, such as hydroxymethyl group and the like can be mentioned. In addition, when the active compound contains an amino group, an amide thereof, a carbamate thereof, and the like can be mentioned. When the active compound contains a hydroxyl group, an ester thereof, a carbonate thereof, a carbamate thereof, and the like can be mentioned. When the compound of the present invention is converted to a prodrug, it may be bonded to amino acid or sugars.

The metabolite in the present invention is a compound obtained by conversion of the compound of the present invention due to a metabolic enzyme and the like in the living organisms. For example, a compound wherein a hydroxyl group has been introduced by metabolism onto the benzene ring of the compound of the present invention, a compound wherein an alkoxy group of the compound of the present invention has been converted to a hydroxyl group by metabolism, a compound wherein an N!O bond of the isoxazole ring of the compound of the present invention has been cleaved by metabolism, and the like can be mentioned. In addition, a compound wherein a carboxylic acid moiety of the compound of the present invention, or a hydroxyl group of the compound of the present invention, which has been added by metabolism, is bonded to glucuronic acid, glucose, or amino acid and the like can be mentioned.

Since the compounds of the present invention and pharmaceutically acceptable salts thereof (hereinafter to be simply referred to as the compounds of the present invention) have low toxicity and inhibit the physiological activity of LPA, they can be used as pharmaceutical agents. For example, they can be used as agents for the prophylaxis or treatment of diseases in which inhibition of the physiological activity of LPA is useful for the prophylaxis or treatment thereof (disease in which LPA receptor participates, and the like). More specifically, they can be used as agents for the prophylaxis or treatment of fibrosis of organs (liver, kidney, lung, and the like), hepatic disease (acute and chronic hepatitis, liver fibrosis, liver cirrhosis, portal hypertension, regenerative failure, non-alcoholic steatohepatitis (NASH), liver hypofunction, hepatic blood flow disorder, and the like), cell proliferative disease (cancer (solid tumor, solid tumor metastasis, vascular fibroma, myeloma, multiple myeloma, Kaposi's sarcoma, leukemia, and the like) and invasive metastasis of cancer cell and the like), inflammatory disease (psoriasis, nephropathy, pneumonia, and the like), gastrointestinal tract disease (irritable bowel syndrome (IBS), inflammatory bowel disease (IBD), abnormal pancreatic secretion, and the like), renal disease, urinary tract-associated disease (benign prostatic hyperplasia or symptoms associated with neuropathic bladder disease, spinal cord tumor, hernia of intervertebral disk, spinal canal stenosis, symptoms derived from diabetes, lower urinary tract disease (obstruction of lower urinary tract and the like), inflammatory disease of lower urinary tract, dysuria, frequent urination, and the like), pancreas disease, abnormal angiogenesis-associated disease (arterial obstruction and the like), brain-associated disease (cerebral infarction, cerebral hemorrhage, and the like) or peripheral neuropathy, and the like. Particularly, they can be used as agents for the prophylaxis or treatment of fibrosis of organs (liver, kidney, lung, and the like) or liver diseases.

The compounds of the present invention and salts thereof can be administered as they are, or as a pharmaceutical composition containing various pharmaceutically acceptable carriers according to a method known per se, orally or parenterally (e.g., routes via intravenous, subcutaneous, intramuscular, suppository, intestinal infusion, ointment, plaster, sublingual, instillation, inhalation, etc.) to a mammal (human, mouse, rat, rabbit, dog, cat, bovine, pig, monkey, etc.). While the dose for the above-mentioned object is determined depending on the objective treatment effect, administration method, treatment period, age, body weight, and the like, when an oral or parenteral route is employed, the daily dose for an adult is generally 1 µg to 10 g by oral administration, and 0.01 µg to 1 g by parenteral administration. The content of the compound of the present invention in the above-mentioned pharmaceutical composition is about 0.01 wt % to 100 wt % of the whole composition.

As a pharmaceutically acceptable carrier for the pharmaceutical composition of the present invention, various organic or inorganic carrier substances conventionally used as materials for preparation can be mentioned. For example, excipients, lubricants, bindesr, disintegrants, water-soluble polymers, basic inorganic salts for solid preparations; solvents, dissolution aids, suspending agents, isotonicity agents, buffers, soothing agents, and the like for liquid preparations can be mentioned. Where necessary, general additives, such as preservatives, antioxidants, coloring agents, sweetening agents, souring agents, bubbling agents, flavors, and the like can also be used.

As the dosage form of such pharmaceutical compositions, for example, tablets, powders, pills, granules, capsules, suppositories, liquids, sugar coatings, depots, syrups, suspensions, emulsions, troches, sublingual tablets, adhesive agents, intraorally disintegrants (tablets), inhalants, intestinal infusions, ointments, plasters, tapes, and eye drops can be mentioned, and a pharmaceutical composition can be produced using ordinary preparation auxiliaries and according to a conventional method.

The pharmaceutical composition of the present invention can be produced according to a method conventionally used in the technical field of preparations, such as a method described, for example, in the Japanese Pharmacopoeia and the like. Concrete production methods of the preparation are described in detail in the following.

For example, when the compound of the present invention is formed as an oral preparation, an excipient, and where necessary, a binder, disintegrant, lubricant, coloring agent, flavoring agent, and the like are added, and the mixture is processed according to a conventional method to give, for example, a tablet, powder, pill, granule, capsule, suppository, solution, sugar coating agent, depot, syrup, and the like. As the excipient, for example, lactose, cornstarch, sucrose, glucose, sorbit, crystalline cellulose, and the like can be used, as the binder, for example, polyvinyl alcohol, polyvinyl ether, ethylcellulose, methylcellulose, gum arabic, tragacanth, gelatin, shellac, hydroxypropylcellulose, hydroxypropyl starch, polyvinylpyrrolidone, and the like can be used, as the disintegrant, for example, starch, agar, gelatin powder, crystalline cellulose, calcium carbonate, sodium hydrogencarbonate, calcium citrate, dextran, pectin, and the like can be used, as the lubricant, for example, magnesium stearate, talc, polyethylene glycol, silica, hydrogenated vegetable oil, and the like can be used, as the coloring agent, those permitted to be added to pharmaceutical products can be used, and as the flavoring agent, cocoa powder, menthol, aromatic powder, mentha oil, borneo camphor, powdered cinnamon bark, and the like are used. It is naturally permissible to appropriately apply a sugar coating, gelatin coating, and other necessary coating to these tablets and granules.

When an injection is to be prepared, a pH adjusting agent, buffer, stabilizer, preservative, and the like are added where necessary, and the mixture is processed according to a conventional method to give a subcutaneous, intramuscular, or intravenous injection.

The compound of the present invention can be used appropriately along with one or more other pharmaceutical agents depending on the desired object. For example, when the compound of the present invention is used for liver fibrosis, it can be used for the treatment concurrently with commercially available drugs for liver diseases, such as interferon, glycyrrhizin, and urso™. In the case of concurrent use, the dose thereof is appropriately determined according to the kind and efficacy of the pharmaceutical agent to be concurrently used, administration method, treatment period, age, body weight, and the like.

While the production methods of the compounds of the present invention are explained in the following, the production methods of the compounds of the present invention are not limited to those mentioned below. In addition, the functional groups other than the reaction site may be protected in advance as necessary before carrying out the below-mentioned reactions and deprotected at a suitable stage. In each step, moreover, the reaction may be carried out according to the methods generally employed, and isolation and purification can be performed by a method conventionally employed, such as crystallization, recrystallization, column chromatography, thin layer chromatography, preparative HPLC, and the like, which are selected as appropriate or used in combination.

The symbols used for the explanation of the production methods are shown in the following. Each symbol is as defined above unless otherwise specified.

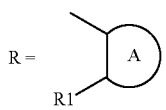

R'=carbamate group, carboxylic acid ester group, and the like,

R", R'''=group forming carboxylate (lower alkyl group such as methyl group, ethyl group, and the like, etc.), and X=halogen atom (fluorine atom, chlorine atom, bromine atom, and iodine atom)

As shown in the following schemes, compound (I-1) encompassed in the compound of the present invention can be produced by Curtius reaction (reaction A) from carboxylic acid, Hofmann reaction (reaction B) according to a reference (*J. Org. Chem.*, 1993, vol. 58, p. 2478 and references cited in this reference), rearrangement reaction (reaction C) according to a reference (*J. Heterocyclic. Chem.*, 1972, 837 and *J. Heterocyclic. Chem.*, 1972, 577), and the like. Furthermore, the optically active final compound can be produced using an optically active alcohol (R3OH) to be used for these reactions.

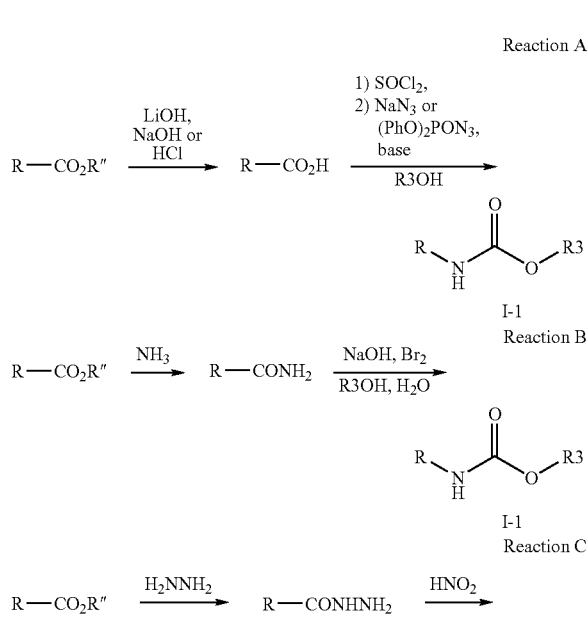

Reaction A

Reaction B

Reaction C

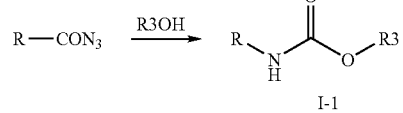

Azolecarboxylic acid, diazolecarboxylic acid, and their esters to be used as starting materials can be produced according to known methods shown below.

1. General Production Methods of Isoxazolecarboxylate and Isoxazolecarboxylic Acid.

Isoxazolecarboxylate represented by formula (b) can be produced by a method similar to the method described in WO0240458, which is shown in the following scheme. To be specific, the 1,3-dicarbonyl compound obtained by reacting a ketone with a dialkyl carbonate is reacted with N,N-dimethylformamide dimethylacetal to give hydroxyacrylate. This compound is further treated with hydroxylamine hydrochloride to give isoxazolecarboxylate represented by formula (b).

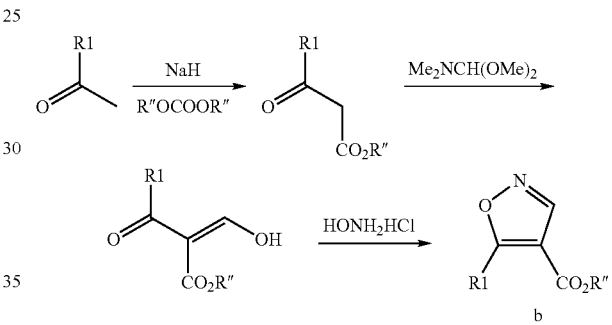

In addition, isoxazolecarboxylate represented by formula (c) can be produced according to a method described in *J. Heterocyclic. Chem.*, 2000, vol. 37, p. 75, which is shown in the following scheme. To be specific, a vinyl ester obtained by reacting propargylate with p-nitrobenzoic acid in the presence of a suitable base (e.g., N-methylmorpholine and the like) is reacted with a chlorooxime form obtained by treating oxime with a suitable chlorinating reagent (e.g., N-chlorosuccinimide and the like) to give isoxazolecarboxylate represented by formula (c).

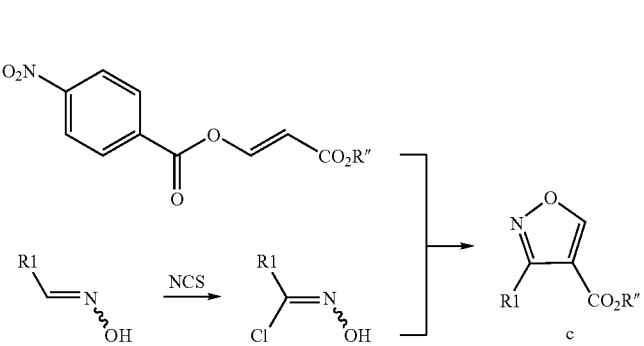

The isoxazolecarboxylate (formula (c)) can also be produced by a method similar to the method described in *Bull. Chem. Soc. Jpn.*, 1999, vol. 72(10), p. 2277. To be specific, an oximecarboxylic acid is reacted with propargylate in the presence of cerium (IV) ammonium nitrate (CAN) to give isoxazolecarboxylate.

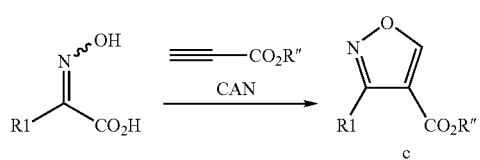

The isoxazolecarboxylate (formula (c)) can also be produced by a method similar to the method described WO9828282. To be specific, an oxime is converted to chlorooxime with N-chlorosuccinimide and then reacted with vinyl carboxylate to give the isoxazolecarboxylate represented by formula (c).

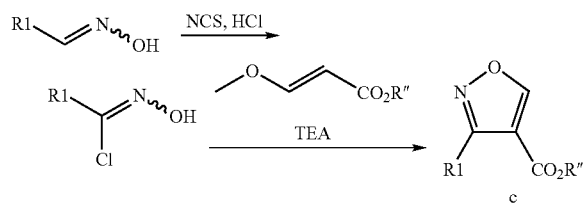

2. General Production Methods of Isothiazolecarboxylate and Isothiazolecarboxylic Acid.

Isothiazolecarboxylic acid represented by formula (d) can be produced by a method similar to the method described in *Bull. Chem. Soc. Jpn.*, 1968, vol. 41, p. 965, which is shown in the following scheme. To be specific, a suitable nitrile is reacted with n-propionitrile in the presence of sodium, and the resulting imine is further reacted with thionyl chloride to give isothiazolenitrile. This compound is treated with concentrated sulfuric acid and sodium sulfite to give the isothiazolecarboxylic acid represented by formula (d).

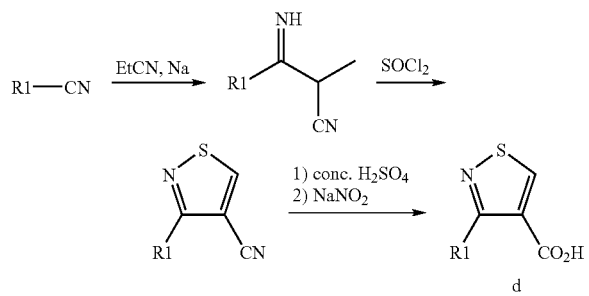

Isothiazolecarboxylate represented by formula (e) can be produced by a known method shown in the following scheme. That is, according to the method described in U.S. Pat. No. 5,087,631, α-bromocarboxylic acid is reacted with potassium thioacetate and the resulting α-thioacetylcarboxylic acid is treated with ammonia to give α-mercaptocarboxylic acid. This compound is further treated with t-butyl nitrite and then dicyclohexylcarbodiimide (DCC) to give 5-membered ring compound (f), which is reacted with propargylate by a method similar to the method described in *Tetrahedron Lett.*, 1971, vol. 12(17), p. 1281, to give the isothiazolecarboxylate represented by formula (e).

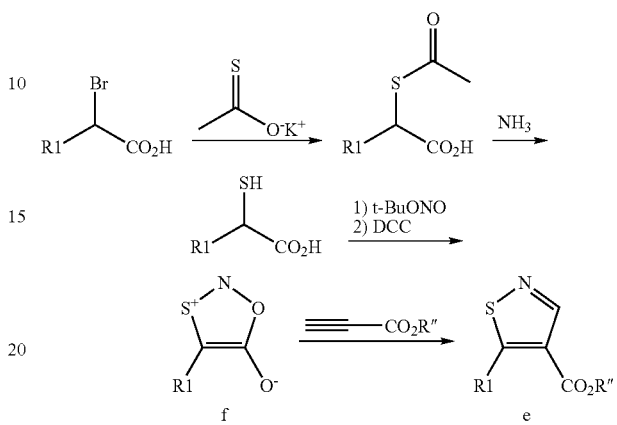

Isothiazolecarboxylate represented by formula (e) can also be produced by a method similar to the method described in *Tetrahedron Lett.*, 1971, vol. 12(17), p. 1281, which is shown in the following scheme. The 5-membered ring compound (f) obtained by the above-mentioned method is reacted with acetylenedicarboxylate to give isothiazoledicarboxylate, which is subjected to hydrolysis, and then decarboxylation reaction to give the isothiazolecarboxylic acid represented by formula (e).

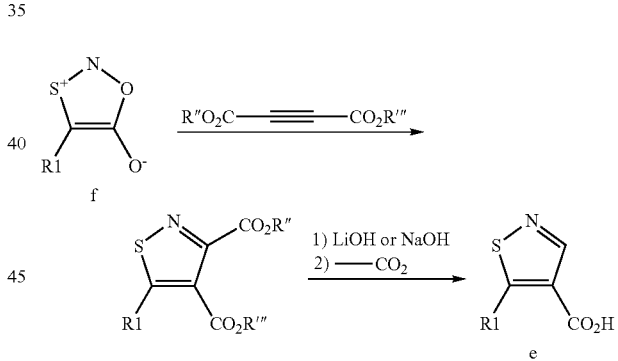

The 5-membered ring compound (f) used here can also be produced according to a method described in *Chem. Ber.*, 1972, vol. 105, p. 188, which is shown in the following scheme. To be specific, α-hydroxycarboxylic acid is reacted with thionyl chloride to give α-chlorocarboxylic acid, which is then reacted with hydrogen sulfide in the presence of a base to give α-mercaptocarboxylic acid. This compound is reacted with ethyl nitrite and dicyclohexylcarbodiimide (DCC) to give the 5-membered ring compound represented by formula (f).

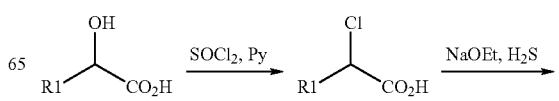

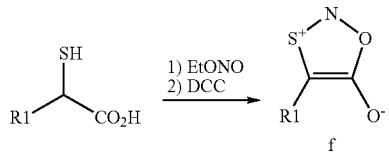

3. General Production Methods of Oxadiazolecarboxylate and Oxadiazolcarboxylic Acid.

1,2,3-Oxadiazolecarboxylate represented by formula (g) can be produced by a known method shown in the following scheme. To be specific, the oxime form obtained by treating β-ketocarboxylate with sodium nitrite in the presence of acetic acid by a method similar to the method described in *J. Am. Chem. Soc.*, 1938, vol. 60, p. 1328, is reduced by a method similar to the method described in *Chem. Ber.*, 1903, vol. 36, p. 3612, to give the amine form. This compound is treated with nitrous acid by a method similar to the method described in *Chem. Ber.*, 1903, vol. 36, p. 3612, to give the 1,2,3-oxadiazolecarboxylate represented by formula (g).

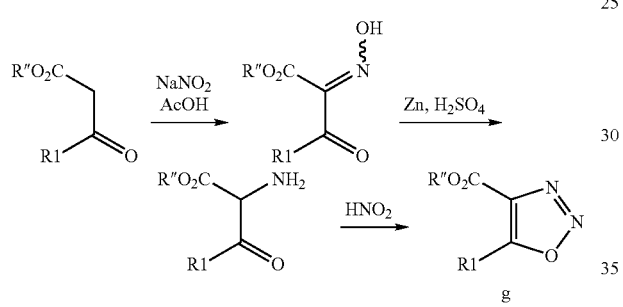

1,2,5-Oxadiazolecarboxylic acid represented by formula (h) can be produced by a known method shown in the following scheme. To be specific, a cyanomethylketone form is treated with sodium nitrite in acetic acid by a method similar to the method described EP 0 389 189 to give the oxime form. This compound is further reacted with hydroxylamine hydrochloride in an aqueous sodium hydroxide solution by a method similar to the method described in *Gazz. Chim. Ital.*, 1931, vol. 61, p. 943, to give the isoxazolone represented by formula (V). This compound is treated with sodium carbonate by a method similar to the method described in *Chem. Ber.*, 1892, vol. 25, p. 2142, to give the 1,2,5-oxadiazolecarboxylic acid represented by formula (h).

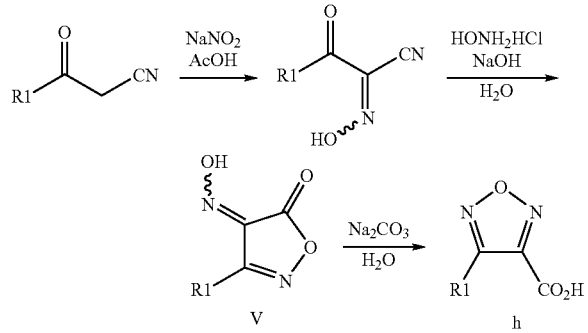

4. General Production Methods of N-oxy-oxadiazolecarboxylate and N-oxy-oxadiazolecarboxylic acid.

N-Oxy-1,2,5-oxadiazolecarboxylic acid represented by formula (I-a,b) can be produced by a method similar to the method described in *Liebigs Ann. Chem.*, 1991, 1211), which is shown in the following scheme. To be specific, a substituted allyl alcohol is reacted with sodium nitrite in acetic acid to give the N-oxy-1,2,5-oxadiazolylmethanol (J-a).

This compound is subjected to Jones oxidization to give the N-oxy-1,2,5-oxadiazolecarboxylic acid represented by formula (I-a). In addition, by heating the N-oxy-1,2,5-oxadiazolylmethanol represented by formula (J-a) in a solvent, the N-oxy-1,2,5-oxadiazolylmethanol represented by formula (J-b) can be produced. This compound is further subjected to Jones oxidization to give the N-oxy-1,2,5-oxadiazolecarboxylic acid represented by formula (I-b).

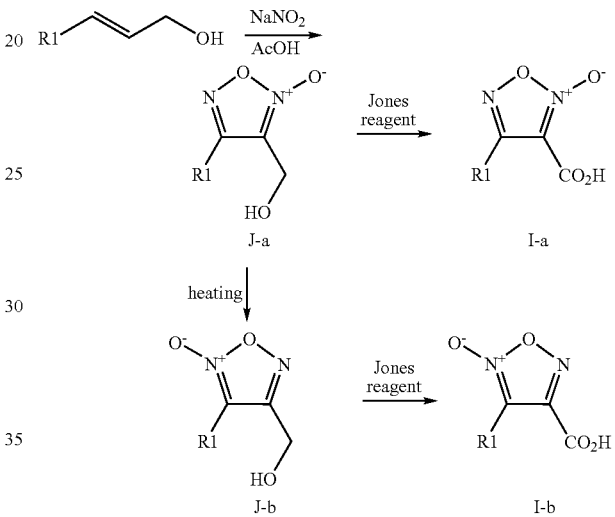

N-Oxy-1,2,5-oxadiazolecarboxylate represented by formula (K-a, b) can also be produced by a method similar to the method described in *Chem. Ber.*, 1895, vol. 28, p. 2675 or *J. Heterocyclic. Chem.*, 1972, 577, which is shown in the following scheme. By treating the dioxime form with nitrous acid to give the N-oxy-1,2,5-oxadiazolecarboxylate represented by formula (K-b). This compound is heated in a solvent to give the N-oxy-1,2,5-oxadiazolecarboxylate represented by formula (K-a).

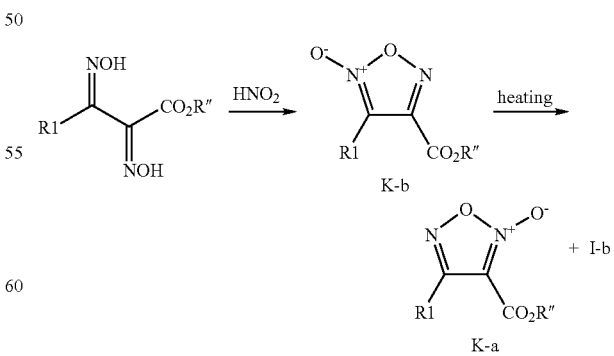

N-Oxy-1,2,5-oxadiazolecarboxylic acid represented by formula (I-a) can also be produced by a method similar to the method described in *Liebigs. Ann. Chem.*, 1990, 335, which is shown in the following scheme. To be specific, the isoxazolone represented by formula (V) is treated with potassium hypochlorite and hydrochloric acid to give the N-oxy-1,2,5-oxadiazolecarboxylic acid represented by formula (I-a).

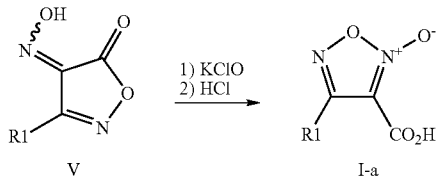

5. General Production Methods of Thiadiazolecarboxylate and Thiadiazolecarboxylic Acid.

1,2,3-Thiadiazolecarboxylic acid represented by formula (L) can be produced by a known method shown in the following scheme. To be specific, an acylhydrazone is treated with thionyl chloride by a method similar to the method described in *Can. J. Chem.*, 1968, vol. 46, p. 1057, to give a 1,2,3-thiadiazole. This compound is treated with carbon dioxide in the presence of methyl lithium by a method similar to the method described in *Synthesis*, 1985, 945, to give the 1,2,3-thiadiazolecarboxylic acid represented by formula (L).

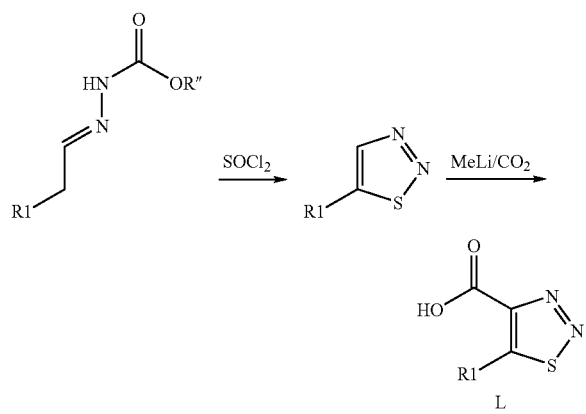

1,2,3-Thiadiazolecarboxylate represented by formula (M) can be produced by a method similar to the method described in *Chem. Ber.*, 1916, vol. 49, p. 1978, which is shown in the following scheme. To be specific, a diazoacetate is treated with a carbonyl halide to give a diazoketone, which is further treated with hydrogen sulfide to give the 1,2,3-thiadiazolecarboxylate represented by formula (M).

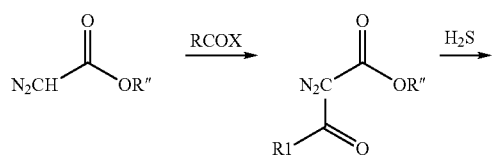

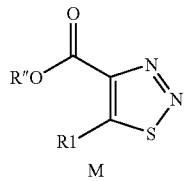

In addition, 1,2,3-thiadiazolecarboxylic acid represented by formula (L) can also be produced by a method similar to the method described in *Annalen*, 1904, vol. 333, p. 4, which is shown in the following scheme. To be specific, the 1,2,3-oxadiazolecarboxylic acid produced by the aforementioned method is reacted with ammonium sulfide to give the 1,2,3-thiodiazolecarboxylic acid represented by formula (L).

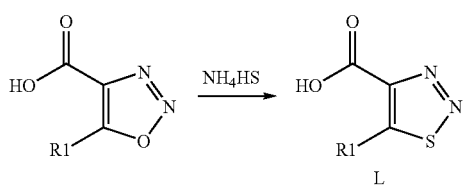

1,2,5-Thiadiazolecarboxylate represented by formula (N) can be produced by a method similar to the method described in *J. Heterocyclic. Chem.*, 1979, 1009, which is shown in the following scheme. To be specific, a substituted acetylenecarboxylate is treated with tetrasulfur tetranitride to give the 1,2,5-thiadiazolecarboxylate represented by formula (N).

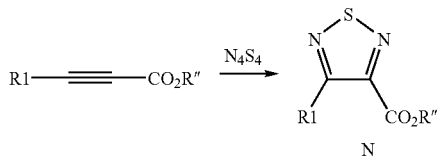

1,2,5-Thiadiazolecarboxylic acid represented by formula (O) can be produced by a known method shown in the following scheme. To be specific, a diaminocarboxylic acid produced by a method similar to the method described in *Liebigs Ann. Chem.*, 1977, 1183, is treated with sulfur chloride by a method similar to the method described in *J. Org. Chem.*, 1967, vol. 32(9), p. 2823, to give 1,2,5-thiadiazolecarboxylic acid represented by formula (O).

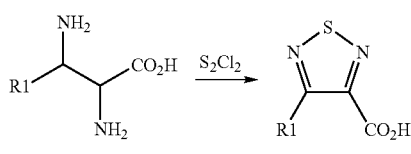

1,2,5-Thiadiazolecarboxylate represented by formula (N) can be produced by a method similar to the method described in *Heterocycles* 2001, vol. 55(1), p. 75, which is shown in the following scheme. To be specific, an α-halooxime form obtained by treating an α-haloketone with hydroxylamine hydrochloride is treated with potassium cyanide to give an isoxazole. This compound is treated with tetrasulfur tetranitride or tetrasulfur tetranitride antimony pentachloride to give a thiadiazolecarboxamide, which is then treated with trifluoroborane to give the 1,2,5-thiadiazolecarboxylate represented by formula (N).

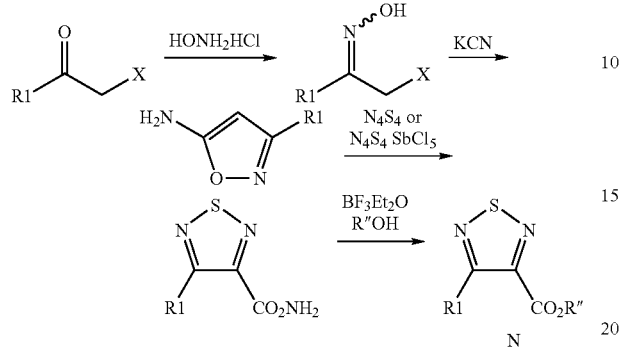

6. Others

A compound represented by the following formula (P) can be produced by condensing compound (R) or (S), wherein Y is a suitable leaving group such as a chloro group, a bromine group, an iodine group, a tosyl group, a mesyl group, and the like, with a suitable nucleophilic agent (T) or (U), wherein Y' is an oxygen atom, a nitrogen atom, a sulfur atom, or a carbon atom activated with an electron-withdrawing substituent, under basic conditions. A compound (P) wherein Y' is a nitrogen atom can also be produced by reductive amination reaction and the like, and a compound (P) wherein Y' is an oxygen atom can also be produced by Mitsunobu reaction and the like.

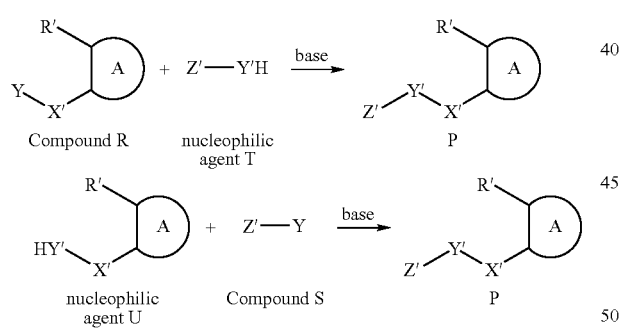

A compound represented by the following formula (I-2) wherein R2 is a substituted or unsubstituted lower alkyl group, a substituted or unsubstituted aralkyl group and the like, which is encompassed in the compound of the present invention, can be produced, for example, according to a method described in *Chem. Pharm. Bull.*, 1981, vol. 29(6), p. 1743, by condensing a compound represented by formula (I-1) with compound (W), (wherein Y is a suitable leaving group such as a chloro group, a bromine group, an iodine group, a tosyl group, a mesyl group, and the like), under basic conditions.

Moreover, a compound represented by formula (I-2) can also be produced utilizing the Mitsunobu reaction between a compound represented by formula (I-1) and a suitable alcohol (Z), and the like.

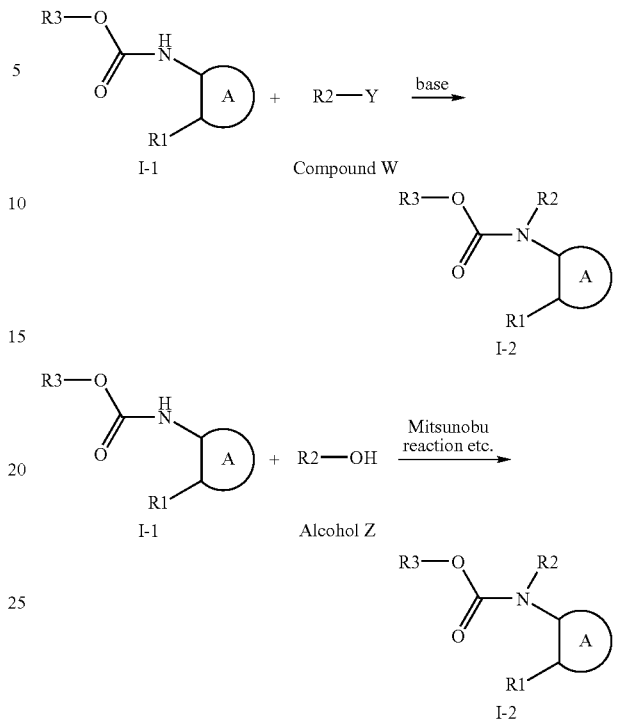

In addition, a compound represented by the following formula (I-3), which is encompassed in the compound of the present invention, can be produced by a method described in *Tetrahedron Lett.*, 2001, vol. 42, p. 755.

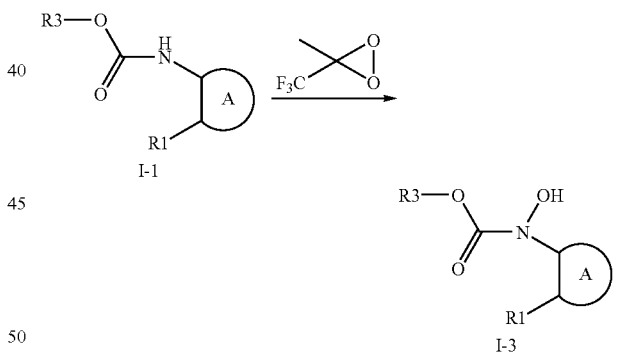

Almost in the same manner as in the above-mentioned method described, or adding a method obvious to those skilled in the art, the following representative examples of the present invention can be synthesized. In each structural formula, R1 is any of the substituents shown in Table 1 and Table 2, and R3 is any of the substituents shown in

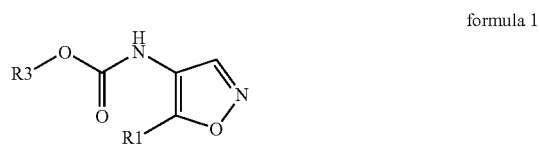

formula 1

-continued

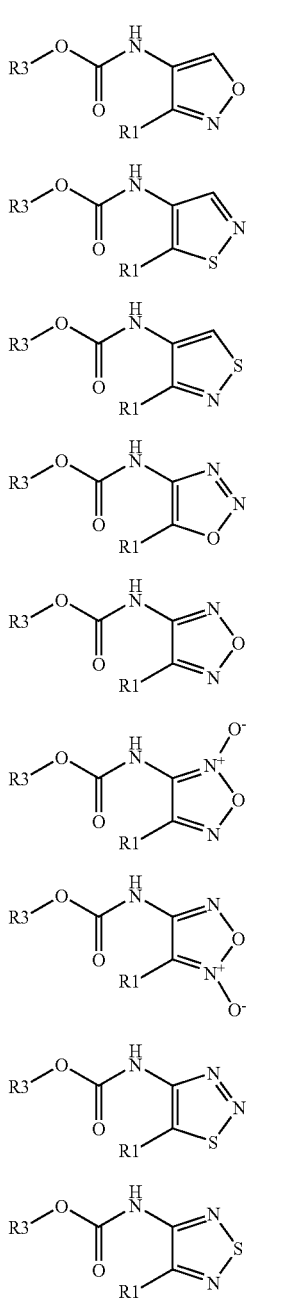

formula 2
formula 3
formula 4
formula 5
formula 6
formula 7
formula 8
formula 9
formula 10

Other features of the invention will become apparent in the course of the following descriptions of exemplary embodiments which are given for illustration of the invention and are not intended to be limiting thereof.

EXAMPLES

Example 1

Synthesis of methyl 3-(4-{4-[1-(2-chlorophenyl) ethoxycarbonylamino]-3-isoxazolyl}benzylsulfanyl) propionate (Compound 1)

The title compound was synthesized by the following two methods (Synthesis Methods A or B).

Synthesis Method A.

(Step A-1) Synthesis of 2-methoxycarbonylvinyl 4-nitrobenzoate

4-Nitrobenzoic acid (10 g, 59.8 mmol) and methyl propargylate (5.5 g, 65.8 mmol) were dissolved in acetonitrile (100 ml), N-methylmorpholine (3 g, 30 mmol) was added, and the mixture was stirred overnight at 40° C. The reaction mixture was concentrated under reduced pressure, and the residue was washed with ether to give the title compound (12.6 g, 50.2 mmol, 83.9%).

$^1$H-NMR(300 MHz, CDCl$_3$) δ=3.80(3H, s), 5.98(1H, d, J=12.6 Hz), 8.25-8.38(4H, m), 8.52(1H, d, J=12.6 Hz).

(Step A-2) Synthesis of 4-methylbenzaldehyde oxime

4-Methylbenzaldehyde (20 g, 166 mmol), hydroxylamine hydrochloride (12.7 g, 183 mmol), and sodium acetate (23.1 g, 282 mmol) were dissolved in a mixed solvent of ethanol (400 ml) and water (150 ml), and the mixture was stirred at 80° C. for 2 hours. The reaction mixture was concentrated under reduced pressure, water was added, and the mixture was extracted with ethyl acetate. The organic layer was washed with saturated aqueous sodium chloride solution, dried over anhydrous sodium sulfate, and concentrated under reduced pressure to give the title compound (20.6 g, 152 mmol, 91.8%).

$^1$H-NMR(300 MHz, CDCl$_3$) δ=2.39(3H, s), 7.21(2H, d, J=7.8 Hz), 7.47(2H, d, J=8.4 Hz), 8.05(1H bs), 8.15(1H, s).

(Step A-3) Synthesis of methyl 3-p-tolyl-isoxazole-4-carboxylate

N-Chlorosuccinimide (9.87 g, 73.4 mmol) and pyridine (175 mg, 2.2 mmol) were dissolved in chloroform (100 ml), 4-methylbenzaldehyde oxime (10 g, 73.4 mmol) was added, and the mixture was stirred until it became clear. A solution of 2-methoxycarbonylvinyl 4-nitrobenzoate (9.22 g, 36.7 mmol) and triethylamine (12.9 g, 128 mmol) in chloroform (180 ml) was slowly added dropwise at 0° C. over 2 hours, and the mixture was stirred overnight at room temperature. Saturated aqueous sodium hydrogencarbonate solution was added, and the mixture was extracted with dichloromethane. The extract was dried over anhydrous sodium sulfate, and the solvent was evaporated under reduced pressure. The residue was purified by column chromatography (hexane:ethyl acetate=5:95) to give the title compound (1.56 g, 7.19 mmol, 19.6%).

$^1$H-NMR(300 MHz, CDCl$_3$) δ=2.41(3H, s), 3.83(3H, s), 7.27(2H, d, J=9.0 Hz), 7.67(2H, d, J=8.4 Hz), 8.98(1H, s).

MS(ESI) m/z 218(M+H)$^+$.

(Step A-4) Synthesis of 3-p-tolyl-isoxazole-4-carboxylic acid

Methyl 3-p-tolyl-isoxazole-4-carboxylate (3.1 g, 14.3 mmol) was dissolved in THF (50 ml), 2N aqueous lithium hydroxide solution (50 ml) was added, and the mixture was stirred for 4 hours. Then, 1N hydrochloric acid (150 ml) was added at 0° C., and the mixture was extracted with ethyl acetate. The extract was dried over anhydrous sodium sulfate. The solvent was evaporated under reduced pressure to give the title compound (2.89 g, 14.3 mmol, 100%).

$^1$H-NMR(300 MHz, CDCl$_3$) δ=2.42(3H, s), 7.28(2H, d, J=7.5 Hz), 7.66(2H, d, J=8.1 Hz), 9.09(1H, s).

MS(ESI) m/z 204(M+H)$^+$.

(Step A-5) Synthesis of 1-(2-chlorophenyl)ethyl(3-p-tolyl-4-isoxazolyl)carbamate 3-p-Tolyl-isoxazole-4-carboxylic acid (2 g, 9.90 mmol), 1-(2-chlorophenyl)ethanol (4.65 g, 29.7 mmol), diphenylphosphoryl azide (3.06 g, 11.9 mmol), and triethylamine (1.10 g, 10.9 mmol) were dissolved in toluene (60 ml), and the mixture was stirred at 90° C. for 1 hour. Saturated aqueous sodium hydrogencarbonate solution was added, and the mixture was extracted with ethyl acetate. The extract was dried over anhydrous sodium sulfate. The solvent was evaporated under reduced pressure, and the residue was purified by column chromatography (hexane:ethyl acetate=80:20-10:90) to give the title compound (2.07 g, 5.80 mmol, 58.6%).

$^1$H-NMR(300 MHz, CDCl$_3$) δ=1.58(3H, d, J=6.6 Hz), 2.45(3H, s), 6.25(1H, q, J=6.6 Hz), 6.41(1H, s), 7.10-7.60 (8H, m), 8.89(1H, s).

MS(ESI) m/z 357(M+H)$^+$.

(Step A-6) Synthesis of 1-(2-chlorophenyl)ethyl[3-(4-bromomethylphenyl)-isoxazolyl]carbamate 1-(2-Chlorophenyl)ethyl(3-p-tolyl-4-isoxazolyl)carbamate (2.07 g, 5.80 mmol), N-bromosuccinimide (1.55 g, 8.70 mmol), and anhydrous perbenzoic acid (187 mg, 0.58 mmol) were dissolved in benzene (50 ml), and the mixture was refluxed overnight. To the reaction mixture was added 20% aqueous sodium thiosulfate solution, and the mixture was extracted with ethyl acetate. The organic layer was washed with saturated aqueous sodium chloride solution and dried over anhydrous sodium sulfate. The solvent was evaporated under reduced pressure, and the residue was purified by column chromatography (hexane:ethyl acetate=95:5-85:15) to give the title compound (1.62 g, 3.73 mmol, 64.4%).

$^1$H-NMR(300 MHz, DMSO-d$_6$) δ=1.51(3H, s), 4.77(2H, s), 6.08(1H, m), 7.15-7.80(8H, m), 9.12(1H, s), 9.44(1H, m).

(Step A-7) Synthesis of methyl 3-(4-{4-[1-(2-chlorophenyl)ethoxycarbonylamino]-3-isoxazolyl}benzylsulfanyl)propionate To a solution of 1-(2-chlorophenyl)ethyl[3-(4-bromomethylphenyl)-isoxazolyl]carbamate (615 mg, 1.41 mmol) in dichloromethane (18 ml) were added triethylamine (855 mg, 8.47 mmol) and methyl 3-mercaptopropionate (445 mg, 4.23 mmol), and the mixture was stirred overnight at room temperature. Water was added, and the mixture was extracted with ethyl acetate. The organic layer was washed with saturated aqueous sodium chloride solution and dried over anhydrous sodium sulfate. The solvent was evaporated under reduced pressure, and the residue was purified by silica gel chromatography (hexane:ethyl acetate=2:1) to give the title compound (58.5 mg, 0.123 mmol, 8.7%).

Synthesis Method B (Step B-1) Synthesis of 4-chloromethylbenzaldehyde

Under an argon atmosphere, 4-chloromethylbenzoic acid (15.08 g, 88.40 mmol) was dissolved in THF (150 ml), and 1M borane-THF complex (135 ml, 135.00 mmol) was slowly added dropwise under ice-cooling. The mixture was stirred at room temperature for 2 hours, 1N sulfuric acid (160 ml) was added, and the mixture was stirred for 1 hour and extracted with ethyl acetate. The organic layer was washed with saturated brine and dried over anhydrous sodium sulfate. The solvent was evaporated under reduced pressure, and the obtained crude product was dissolved in dichloromethane (300 ml). Manganese dioxide (76.94 g, 885.0 mmol) was added, and the mixture was stirred overnight at room temperature. After filtration through celite, the filtrate was concentrated under reduced pressure to give the title compound (11.93 g, 87%).

$^1$H-NMR(300 MHz, CDCl$_3$) δ=4.64(2H, s), 7.57(2H, d, J=6.9 Hz), 7.89(2H, d, J=6.9 Hz), 10.03(1H, s).

(Step B-2) Synthesis of 4-chloromethylbenzaldehyde oxime

4-Chloromethylbenzaldehyde (11.93 g, 77.17 mmol) was dissolved in ethanol (200 ml), hydroxylamine hydrochloride (10.73 g, 154.41 mmol) was added, and the mixture was stirred at 50° C. for 3 hours. Ethanol was evaporated under reduced pressure, water was added, and the mixture was extracted with ethyl acetate. The extract was washed with saturated brine and dried over anhydrous sodium sulfate. The solvent was evaporated under reduced pressure to give the title compound (12.69 g, 97%).

$^1$H-NMR(300 MHz, CDCl$_3$) δ=4.59(2H, s), 7.40(2H, d, J=7.2 Hz), 7.57(2H, d, J=7.2 Hz), 7.85-8.10(1H, m), 8.14(H, s).

(Step B-3) Synthesis of N-hydroxy-4-chloromethylbenzenecarboxyimidoyl chloride

4-Chloromethylbenzaldehyde oxime (12.69 g, 74.82 mmol) was dissolved in DMF (250 ml), N-chlorosuccinimide (12.00 g, 89.87 mmol), and then 4N hydrogen chloride in 1,4-dioxane (120 ml) were added, and the mixture was stirred at room temperature for 30 min. Water was added, and the mixture was extracted with ethyl acetate. The organic layer was washed with water and saturated brine and dried over anhydrous sodium sulfate. The solvent was evaporated under reduced pressure to give the title compound (15.27 g, 100%).

$^1$H-NMR(300 MHz, CDCl$_3$) δ=4.60(2H, s), 7.43(2H, d, J=7.5 Hz), 7.84(2H, d, J=7.5 Hz), 8.12-8.19(1H, m).

(Step B-4) Synthesis of methyl 3-(4-chloromethylphenyl)isoxazole-4-carboxylate

N-Hydroxy-4-chloromethylbenzenecarboxyimidoyl chloride (15.27 g, 74.82 mmol) was dissolved in dichloromethane (300 ml), methyl 3-methoxyacrylate (10.43 g, 89.82 mmol) was added, and triethylamine (21 ml, 151 mmol) was slowly added dropwise. The mixture was stirred overnight at room temperature. Water was added, and the mixture was extracted with dichloromethane. The extract was washed with saturated brine and dried over anhydrous sodium sulfate. The solvent was evaporated under reduced pressure, and the obtained crude product was purified by silica gel chromatography (hexane:ethyl acetate=5:1) to give the title compound (9.67 g, 51%).

$^1$H-NMR(300 MHz, CDCl$_3$) δ=3.84(3H, s), 4.63(2H, s), 7.49(2H, d, J=6.9 Hz), 7.70(2H, d, J=6.9 Hz), 9.01(1H, s).

(Step B-5) Synthesis of 3-(4-chloromethylphenyl)isoxazole-4-carboxylic acid

Methyl 3-(4-chloromethylphenyl)isoxazole-4-carboxylate (7.59 g, 30.16 mmol) was dissolved in THF-water (2:1, 225 ml), lithium hydroxide monohydrate (5.06 g, 120.6 mmol) was added, and the mixture was stirred at room temperature for 6 hours. THF was evaporated under reduced pressure, 2N hydrochloric acid was added to weakly acidify the reaction mixture, and the mixture was extracted with ethyl acetate. The organic layer was washed with saturated brine and dried over anhydrous sodium sulfate. The solvent was evaporated under reduced pressure to give the title compound (7.14 g, 100%).

¹H-NMR(300 MHz, CDCl₃) δ=4.70(2H, s), 7.52(2H, d, J=8.4 Hz), 7.77(2H, d, J=8.4 Hz), 9.31(1H, s).

(Step B-6) Synthesis of 1-(2-chlorophenyl)ethyl[3-(4-chloromethylphenyl)isoxazolyl]-carbamate 3-(4-Chloromethylphenyl)isoxazole-4-carboxylic acid (5.78 g, 24.32 mmol), 1-(2-chlorophenyl)ethanol (7.66 g, 48.91 mmol), diphenylphosphoryl azide (8.11 g, 29.47 mmol), and triethylamine (3.71 g, 36.66 mmol) were dissolved in toluene (70 ml), and the mixture was stirred at 90° C. for 2 hours. The solvent was evaporated under reduced pressure, water was added, and the mixture was extracted with ethyl acetate. The organic layer was washed with saturated brine and dried over anhydrous sodium sulfate. The solvent was evaporated under reduced pressure, and the obtained crude product was purified by silica gel chromatography (hexane:ethyl acetate=4:1) to give the title compound (6.78 g, 71%).
¹H-NMR(300 MHz, CDCl₃) δ=1.57(3H, d, J=6.6 Hz), 4.62(2H, s), 6.23(1H, q, J=6.6 Hz), 6.36(1H, brs), 7.20-7.62 (8H, m), 8.89(1H, s).
MS(ESI) m/z 391(M+H)⁺.

(Step B-7) Synthesis of methyl 3-(4-{4-[1-(2-chlorophenyl)ethoxycarbonylamino]-3-isoxazolyl}benzylsulfanyl)propionate 1-(2-Chlorophenyl)ethyl[3-(4-chloromethylphenyl)isoxazolyl]carbamate (3.51 g, 8.97 mmol) was dissolved in dichloromethane (70 ml), methyl 3-mercaptopropionate (4.46 g, 37.11 mmol) and triethylamine (5.45 g, 53.86 mmol) were added, and the mixture was stirred overnight at room temperature. The solvent was evaporated under reduced pressure, and the residue was purified by silica gel chromatography (hexane:ethyl acetate=4:1) to give the title compound (2.80 g, 66%). The ¹H-NMR and MS spectrum of the compound obtained here matched with the spectrum of the compound obtained in Example 1, Step A-7.

Example 2

Synthesis of 3-(4-{4-[1-(2-chlorophenyl)ethoxycarbonylamino]-3-isoxazolyl}benzylsulfanyl)propionic acid (Compound 2)

To a solution of methyl 3-(4-{4-[1-(2-chlorophenyl) ethoxycarbonylamino]-3-isoxazolyl}benzylsulfanyl)propionate (37 mg, 0.078 mmol) obtained according to Example 1 in tetrahydrofuran (1 ml) was added 1N lithium hydroxide solution (1 ml), and the mixture was stirred at room temperature for 2 hours. 1N Hydrochloric acid (1.5 ml) was added, and the mixture was partitioned by adding ethyl acetate (3 ml). The organic layer was washed with saturated aqueous sodium chloride solution and dried over anhydrous sodium sulfate. The solvent was evaporated under reduced pressure to give the title compound (35.0 mg, 0.076 mmol, 97%).

Example 3

Synthesis of 3-(4-{4-[(1R)-1-(2-chlorophenyl) ethoxycarbonylamino]-3-isoxazolyl}benzylsulfanyl) propionic acid (Compound 3)

The title compound was synthesized by a method utilizing optical resolution of a racemate by chromatography using an optically active column (Synthesis Method A) and a method utilizing the Curtius reaction using (1R)-1-(2-chlorophenyl) ethanol (Synthesis Method B).

Synthesis Method A.

(Step A-1) Synthesis of methyl 3-(4-{4-[(1R)-1-(2-chlorophenyl)ethoxycarbonylamino]-3-isoxazolyl}benzylsulfanyl)propionate by optical resolution Methyl 3-(4-{4-[1-(2-chlorophenyl)ethoxycarbonylamino]-3-isoxazolyl}benzylsulfanyl)propionate (110 mg, 0.232 mmol) was subjected to optical resolution by high performance liquid chromatography (HPLC) (hexane:ethanol=8:2) using CHIRALCEL OD column (2 cm I.D.×25 cm L; DAICEL CHEMICAL IND., LTD) to give the title compound (R form, 54 mg, 49%) along with its S form (55 mg, 50%). The optical purity was determined by HPLC analysis using an optically active column.

R Form:
MS(ESI) m/z 475(M+H)⁺.

optical purity=98% ee (HPLC analysis: CHIRALCEL OD (0.46 cm I.D.×25 cm L), hexane:ethanol=85:15, flow rate=1.0 ml/min, retention time 9.54 min)

S Form:

optical purity=90% ee (HPLC analysis: CHIRALCEL OD (0.46 cm I.D.×25 cm L), hexane:ethanol=85:15, flow rate=1.0 ml/min, retention time 10.91 min)

(Step A-2) Synthesis of 3-(4-{4-[(1R)-1-(2-chlorophenyl)ethoxycarbonylamino]-3-isoxazolyl}benzylsulfanyl)propionic acid The title compound (58 mg, 0.126 mmol, 100%) was obtained from methyl 3-(4-{4-[(1R)-1-(2-chlorophenyl) ethoxycarbonylamino]-3-isoxazolyl}benzylsulfanyl)-propionate (42 mg, 0.0885 mmol) according to the method of Example 2.

Synthesis Method B.

(Step B-1) Synthesis of (R)-1-(2-chlorophenyl)ethanol

Reaction was carried out using 2'-chloroacetophenone (11.90 g, 76.77 mmol) and (+)-B-chlorodiisopinocamphenylborane ((+)-DIP-Cl) (25.00 g, 77.88 mmol) and according to *J. Org. Chem.*, 1985, vol. 50, p. 5446; and 1988, vol. 53, p. 2916, to give the title compound (8.81 g, 72%). The optical purity was determined by HPLC analysis using an optically active column after conversion to the acetate (using acetic anhydride and triethylamine in dichloromethane).

$[\alpha]_D$=57.8° (CH₂Cl₂, c=1.83)

optical purity=92% ee (HPLC analysis: CHIRALCEL OD (0.46 cm I.D.×25 cm L), hexane:ethanol=99:1, flow rate=1.0 ml/min, retention time R form 4.85 min (peak area 96.1%), S form 5.84 min (peak area 3.9%)

(Step B-2) Synthesis of 3-(4-{4-[(1R)-1-(2-chlorophenyl)ethoxycarbonylamino]-3-isoxazolyl}benzylsulfanyl)propionic acid Reactions similar to those of Step B-6 and B-7 of Example 1 were carried out using 3-(4-chloromethylphenyl)isoxazole-4-carboxylic acid synthesized in Step B-5 of Example 1 and (R)-1-(2-chlorophenyl)ethanol, and hydrolysis was further carried out in the same manner as in Example 2 to give the title compound. The $^1$H-NMR and MS spectrum of the compound obtained here matched with the spectrum of the compound obtained in Step A-2 of Example 3.

Example 4

Synthesis of N-acetyl-S-(4-{4-[1-(2-chlorophenyl)ethoxycarbonylamino]-3-isoxazolyl}benzyl)-L-cysteine (Compound 4)

Reaction similar to that of Step B-7 of Example 1 was carried out using Compound 1 and N-acetyl-L-cysteine to give the title compound.

Example 5

Synthesis of 2-(4-{4-[1-(2-chlorophenyl)ethoxycarbonylamino]-3-isoxazolyl}benzylsulfanyl)ethanesulfonic acid (Compound 5)

Reaction similar to that of Step B-7 of Example 1 was carried out using Compound 1 (100 mg, 0.256 mmol) and sodium 2-mercaptoethanesulfonate (127 mg, 0.774 mmol) to give the title compound (50 mg, 39%).

Example 6

Synthesis of 3-(4-{4-[(1R)-1-(2-bromophenyl)ethoxycarbonylamino]-3-isoxazolyl}benzylsulfanyl)propionic acid (Compound 6)

(Step 1) Synthesis of (1R)-1-(2-bromophenyl)ethyl [3-(4-chloromethylphenyl)-isoxazolyl]carbamate Reaction was carried out according to the method of Step B-6 of Example 1 using 3-(4-chloromethylphenyl)isoxazole-4-carboxylic acid (compound of Step B-5 of Example 1) (748 mg, 3.17 mmol) and (R)-1-(2-bromophenyl)ethanol (744 mg, 3.70 mmol) to give the title compound (649 mg, 47%).

(Step 2) Synthesis of methyl 3-(4-{4-[(1R)-1-(2-bromophenyl)ethoxycarbonylamino]-3-isoxazolyl}benzylsulfanyl)propionate Reaction was carried out according to the method of Step B-7 of Example 1 using (1R)-1-(2-bromophenyl)ethyl[3-(4-chloromethylphenyl)isoxazolyl]carbamate (287 mg, 8.97 mmol) and methyl 3-mercaptopropionate (240 mg, 2.00 mmol) to give the title compound (284 mg, 83%).
MS(ESI) m/z 519(M+H)$^+$, 521(M+2+H)$^+$.

(Step 3) Synthesis of 3-(4-{4-[(1R)-1-(2-bromophenyl)ethoxycarbonylamino]-3-isoxazolyl}benzylsulfanyl)propionic acid Reaction was carried out in the same manner as in Example 2 using methyl 3-(4-{4-[(1R)-1-(2-bromophenyl)ethoxycarbonylamino]-3-isoxazolyl}benzylsulfanyl)-propionate (138 mg, 0.266 mmol) to give the title compound (70 mg, 52%).

Example 7

Synthesis of N-acetyl-S-(4-{4-[(1R)-1-(2-bromophenyl)-ethoxycarbonylamino]-3-isoxazolyl}benzyl)-L-cysteine (Compound 7)

Reaction was carried out in the same manner as in Step B-7 of Example 1 using (1R)-1-(2-bromophenyl)ethyl[3-(4-chloromethylphenyl)isoxazolyl]carbamate (compound of Step 1 of Example 6)(102 mg, 0.234 mmol) and N-acetyl-L-cysteine to give the title compound (88 mg, 67%).

Example 8

Synthesis of 3-(4-{4-[1-(2-chloro-1-cyclopentenyl)ethoxycarbonylamino]-3-isoxazolyl}benzylsulfanyl) propionic acid (Compound 8)

(Step 1) Synthesis of 2-chloro-1-cyclopentenecarbaldehyde

Under an argon atmosphere, cyclopentanone (500 mg, 5.94 mmol) was dissolved in anhydrous toluene (10 ml), anhydrous dimethylformamide (687 μl, 8.91 mmol) and phosphorus oxychloride (830 μl, 8.91 mmol) were added dropwise, and the mixture was stirred at room temperature for 2 hours. Water (15 ml) was added, and the mixture was stirred for 30 minutes. 4N Aqueous sodium hydroxide solution (9 ml) was added, and the mixture was extracted with ethyl acetate. The organic layer was washed with saturated aqueous sodium chloride solution and dried over anhydrous sodium sulfate. The solvent was evaporated under reduced pressure to give the title compound (636 mg, 4.87 mmol, 82.0%).

(Step 2) Synthesis of 1-(2-chloro-1-cyclopentenyl)ethanol

Under an argon atmosphere, 2-chloro-1-cyclopentenecarbaldehyde (630 mg, 4.82 mmol) was dissolved in anhydrous tetrahydrofuran (19 ml), methylmagnesium bromide (1.4M toluene solution, 4.1 ml) was added dropwise at 0° C., and the mixture was stirred at room temperature for 30 minutes. Isopropanol (2 ml) was added at 0° C., and the solvent was evaporated under reduced pressure. 1N Hydrochloric acid was added, and the mixture was extracted with ethyl acetate. The organic layer was washed with saturated aqueous sodium chloride solution and dried over anhydrous sodium sulfate. The solvent was evaporated under reduced pressure, and the residue was purified by silica gel chromatography (hexane: ethyl acetate=10:1-6:1) to give the title compound (294 mg, 2.01 mmol, 41.6%).

(Step 3) Synthesis of 1-(2-chloro-1-cyclopentenyl) ethyl[3-(4-chloromethylphenyl)-4-isoxazolyl]carbamate The title compound (435 mg, 1.14 mmol, 67.9%) was obtained from 3-(4-chloromethylphenyl)isoxazole-4-carboxylic acid (500 mg, 2.10 mmol) and 1-(2-chloro-1-cyclopentenyl)ethanol (243 mg, 1.68 mmol) according to the method of Step B-6 of Example 1.
MS(ESI) m/z 381(M+H)$^+$.

(Step 4) Synthesis of methyl 3-(4-{4-[1-(2-chloro-1-cyclopentenyl)-ethoxycarbonylamino]-3-isoxazolyl}benzylsulfanylpropionate The title compound (324 mg, 0.697 mmol, 70.4%) was obtained from 1-(2-chloro-1-cyclopentenyl)ethyl[3-(4-chloromethyl-phenyl)-4-isoxazolyl]carbamate (375 mg, 0.989 mmol) and methyl 3-mercaptopropionate (329 μl, 2.97 mmol) according to the method of Step B-7 of Example 1.
MS(ESI) m/z 465(M+H)$^+$.

(Step 5) Synthesis of 3-(4-{4-[1-(2-chloro-1-cyclopentenyl)ethoxycarbonylamino]-3-isoxazolyl}benzylsulfanyl)propionic acid The title compound (56.3 mg, 0.125 mmol, 58.1%) was obtained from methyl 3-(4-{4-[1-(2-chloro-1-cyclopentenyl)ethoxycarbonylamino]-3-isoxazolyl}-benzylsulfanyl)propionate (100 mg, 0.215 mmol) according to the method of Example 2.

Example 9

Synthesis of 3-(4-{4-[(1R)-1-(2-chloro-1-cyclopentenyl)ethoxycarbonyl-amino]-3-isoxazolyl}benzylsulfanyl)propionic acid (Compound 9)

(Step 1) Synthesis of methyl 3-(4-{4-[(1R)-1-(2-chloro-1-cyclopentenyl)-ethoxycarbonylamino]-3-isoxazolyl}benzylsulfanylpropionate Methyl 3-(4-{4-[1-(2-chloro-1-cyclopentenyl)ethoxycarbonylamino]-3-isoxazolyl}benzylsulfanylpropionate (156 mg, 0.336 mmol) was subjected to optical resolution by high performance liquid chromatography (HPLC) (hexane:isopropanol=9:1) using a CHIRALCEL OD column (2 cm I.D.× 25 cm L; DAICEL CHEMICAL IND., LTD) to give the title compound (R form, 30 mg, 19%) along with its S form (38 mg, 25%). The optical purity was determined by HPLC analysis using an optically active column.

R Form:
MS(ESI) m/z 465(M+H)$^+$.
$[\alpha]_D$=−27.6° (MeOH, c=0.590)

optical purity=95% ee (HPLC: CHIRALCEL OD (0.46 cm I.D.×25 cm L), hexane:isopropanol=9:1, flow rate=1.0 ml/min, retention time 16.34 min)

S Form:
$[\alpha]_D$=25.5° (MeOH, c=0.675)

optical purity=93% ee (HPLC: CHIRALCEL OD (0.46 cm I.D.×25 cm L), hexane:isopropanol=9:1, flow rate=1.0 ml/min, retention time 18.54 min)

(Step 2) Synthesis of 3-(4-{4-[(1R)-1-(2-chloro-1-cyclopentenyl)ethoxycarbonylamino]-3-isoxazolyl}benzylsulfanyl)propionic acid The tide compound (20.5 mg, 0.0455 mmol, 96.7%) was obtained from methyl 3-(4-{4-[(1R)-1-(2-chloro-1-cyclopentenyl)ethoxycarbonylamino]-3-isoxazolyl}-benzylsulfanylpropionate (21.9 mg, 0.0471 mmol) according to the method of Example 2.

Example 10

Synthesis of 3-(4-{4-[1-(2-chloro-1-cyclohexenyl)ethoxycarbonylamino]-3-isoxazolyl}benzylsulfanyl)propionic acid (Compound 10)

(Step 1) Synthesis of 2-chloro-1-cyclohexenecarbaldehyde

The title compound (1.32 g, 9.13 mmol, 92.3%) was obtained from cyclohexanone (1.0 g, 10.2 mmol) according to a method similar to that of Step 1 of Example 8.

(Step 2) Synthesis of 1-(2-chloro-1-cyclohexenyl)ethanol

The tide compound (335 mg, 2.09 mmol, 46.3%) was obtained from 2-chloro-1-cyclohexenecarbaldehyde (650 mg, 4.50 mmol) according to a method similar to that of Step 2 of Example 8.

(Step 3) Synthesis of 1-(2-chloro-1-cyclohexenyl)ethyl[3-(4-chloromethylphenyl)-4-isoxazolyl]carbamate The title compound (521 mg, 1.32 mmol, 78.4%) was obtained from 3-(4-chloromethylphenyl)isoxazole-4-carboxylic acid (500 mg, 2.10 mmol) and 1-(2-chloro-1-cyclohexenyl)ethanol (270 mg, 1.68 mmol) according to the method of Step B-6 of Example 1.
MS(ESI) m/z 396(M+H)$^+$.

(Step 4) Synthesis of methyl 3-(4-{4-[1-(2-chloro-1-cyclohexenyl)ethoxycarbonylamino]-3-isoxazolyl}benzylsulfanyl)propionate The title compound (437 mg, 0.913 mmol, 79.6%) was obtained from 1-(2-chloro-1-cyclohexenyl)ethyl[3-(4-chloromethylphenyl)-4-isoxazolyl]carbamate (435 mg, 1.15 mmol) and methyl 3-mercaptopropionate (380 μl, 3.44 mmol) according to the method of Step B-7 of Example 1.
MS(ESI) m/z 479(M+H)$^+$.

(Step 5) Synthesis of 3-(4-{4-[1-(2-chloro-1-cyclohexenyl)ethoxycarbonylamino]-3-isoxazolyl}benzylsulfanyl)propionic acid The title compound (94.7 mg, 0.204 mmol, 94.9%) was obtained from methyl 3-(4-{4-[1-(2-chloro-1-cyclohexenyl)ethoxycarbonylamino]-3-isoxazolyl}benzyl-sulfanylpropionoate (103 mg, 0.215 mmol) according to the method of Example 2.

Example 11

Synthesis of 3-(4-{4-[1-(2-chlorophenyl)ethoxycarbonylamino]-3-isoxazolyl}benzylsulfonyl)propionic acid (Compound 11)

(Step 1) Synthesis of methyl 3-(4-{4-[1-(2-chlorophenyl)ethoxycarbonylamino]-3-isoxazolyl}benzylsulfonyl)propionate To a solution of methyl 3-(4-{4-[1-(2-chlorophenyl)ethoxycarbonylamino]-3-isoxazolyl}benzylsulfanyl)propionate (Compound 1) (82 mg, 0.173 mmol) in dichloromethane (10 ml) was added m-chloroperbenzoic acid (92 mg, 0.533 mmol), and the mixture was stirred at room temperature for 2 hours. 1N Sodium carbonate aqueous solution was added to the reaction mixture, and the mixture was extracted with dichloromethane. The organic layer was washed with saturated brine and dried over anhydrous sodium sulfate. The solvent was evaporated under reduced pressure, and the obtained crude product was purified by silica gel chromatography (hexane:ethyl acetate=4:1) to give the title compound (83 mg, 95%).

MS (ESI) m/z 507 (M+H)$^+$.

(Step 2) Synthesis of 3-(4-{4-[1-(2-chlorophenyl)ethoxycarbonylamino]-3-isoxazolyl}-benzylsulfonyl)propionic acid Reaction similar to that of Example 2 was carried out using methyl 3-(4-{4-[1-(2-chlorophenyl)ethoxycarbonylamino]-3-isoxazolyl}benzylsulfonyl)propionate to give the title compound (24 mg, 30%).

Example 12

Synthesis of 3-(4-{4-[(1R)-1-(2-bromophenyl)ethoxycarbonylamino]-3-isoxazolyl}benzylsulfonyl)propionic acid (Compound 12)

Reaction similar to that of Example 11 was carried out using methyl 3-(4-{4-[(1R)-1-(2-bromophenyl)ethoxycarbonylamino]-3-isoxazolyl}benzylsulfanyl)propionate (compound of Step 2 of Example 6) to give the title compound (55 mg, 76%).

Example 13

Synthesis of 3-(4-{4-[1-(2-chloro-1-cyclohexenyl)ethoxycarbonylamino]-3-isoxazolyl}benzylsulfonyl)propionic acid (Compound 13)

Reaction similar to that of Example 11 was carried out using methyl 3-(4-{4-[1-(2-chloro-1-cyclohexenyl)ethoxycarbonylamino]-3-isoxazolyl}benzylsulfanyl)propionate (compound of Step 4 Example 10) to give the title compound (6.2 mg, 11%).

Example 14

Synthesis of {[2-(4-{4-[1-(2-chlorophenyl)ethoxycarbonylamino]-3-isoxazolyl}phenyl)ethyl]thio}acetic acid (Compound 14)

(Step 1) Synthesis of 4-(2-chloroethyl)benzaldehyde 4-(2-Chloroethyl)benzoic acid (2.00 g, 10.83 mmol) was dissolved in THF (40 ml) under an argon atmosphere, and 1M borane-THF complex (16 ml, 16.00 mmol) was slowly added dropwise under ice-cooling. After stirring at room temperature for 2 hours, 1N sulfuric acid (36 ml) was added, and the mixture was stirred for 1 hour and extracted with ethyl acetate. The organic layer was washed with saturated brine and dried over anhydrous sodium sulfate. The solvent was evaporated under reduced pressure, and the obtained crude product was dissolved in dichloromethane (50 ml). Manganese dioxide (10.00 g) was added, and the mixture was stirred overnight at room temperature. After filtration through celite, the filtrate was concentrated under reduced pressure to give the title compound (1.71 g, 91%).

(Step 2) Synthesis of 4-(2-chloroethyl)benzaldehyde oxime 4-(2-Chloroethyl)benzaldehyde (1.70 g, 10.08 mmol) was dissolved in ethanol (35 ml), hydroxylamine hydrochloride (1.05 g, 15.11 mmol) was added, and the mixture was stirred at 50° C. for 2 hours. Ethanol was evaporated under reduced pressure, and water was added. The mixture was extracted with ethyl acetate. The extract was washed with saturated brine and dried over anhydrous sodium sulfate. The solvent was evaporated under reduced pressure to give the title compound (1.75 g, 95%).

(Step 3) Synthesis of N-hydroxy-4-(2-chloroethyl)benzenecarboxyimidoyl chloride 4-(2-Chloroethyl)benzaldehyde oxime (1.74 g, 9.48 mmol) was dissolved in DMF (40 ml), N-chlorosuccinimide (1.52 g, 11.38 mmol), and then 4N hydrogen chloride in 1,4-dioxane (20 ml) were added, and the mixture was stirred at room temperature for 1 hour. Water was added, and the mixture was extracted with ethyl acetate. The organic layer was washed with water and saturated brine and dried over anhydrous sodium sulfate. The solvent was evaporated under reduced pressure to give the title compound (2.07 g, 100%).

(Step 4) Synthesis of methyl 3-(4-(2-chloroethyl)phenyl)isoxazole-4-carboxylate

N-Hydroxy-4-(2-chloroethyl)benzenecarboxyimidoyl chloride (2.07 g, 9.48 mmol) was dissolved in dichloromethane (5 ml), methyl 3-methoxyacrylate (1.32 g, 11.37 mmol) was added, and triethylamine (1.92 g, 18.97 mmol) was slowly added dropwise. The mixture was stirred overnight at room temperature. Water was added, and the mixture was extracted with dichloromethane. The extract was washed with saturated brine and dried over anhydrous sodium sulfate. The solvent was evaporated under reduced pressure, and the obtained crude product was purified by silica gel chromatography (hexane:ethyl acetate=5:1) to give the title compound (1.46 g, 58%).

MS(ESI) m/z 266 (M+H)$^+$.

(Step 5) Synthesis of 3-(4-(2-chloroethyl)phenyl)isoxazole-4-carboxylic acid

Methyl 3-(4-(2-chloroethyl)phenyl)isoxazole-4-carboxylate (1.46 g, 5.49 mmol) was dissolved in THF-water (2:1, 30 ml), lithium hydroxide monohydrate (922 mg, 21.97 mmol) was added, and the mixture was stirred at room temperature for 6 hours. THF was evaporated under reduced pressure, 2N hydrochloric acid was added to weak-acidify the reaction mixture, and the mixture was extracted with ethyl acetate. The organic layer was washed with saturated brine and dried over anhydrous sodium sulfate. The solvent was evaporated under reduced pressure to give the title compound (1.38 g, 100%).

MS (ESI) m/z 252 (M+H)$^+$.

(Step 6) Synthesis of 1-(2-chlorophenyl)ethyl[3-(4-(2-chloroethyl)phenyl)isoxazolyl]-carbamate 3-(4-(2-Chloroethyl)phenyl)isoxazole-4-carboxylic acid (710 mg, 2.82 mmol), 1-(2-chlorophenyl)ethanol (530 mg, 3.38 mmol), diphenylphosphoryl azide (930 mg, 3.38 mmol), and triethylamine (1.43 g, 14.13 mmol) were dissolved in toluene (15 ml), and the mixture was stirred at 90° C. for 1 hour. The solvent was evaporated under reduced pressure, and water was added. The mixture was extracted with ethyl acetate. The organic layer was washed with saturated brine and dried over anhydrous sodium sulfate. The solvent was evaporated under reduced pressure, and the obtained crude product was purified by silica gel chromatography (hexane: ethyl acetate=5:1) to give the title compound (963 mg, 84%).

MS (ESI) m/z 405 (M+H)$^+$.

(Step 7) Synthesis of methyl {[2-(4-{4-[1-(2-chlorophenyl)ethoxycarbonylamino]-3-isoxazolyl}phenyl)ethyl]thio}acetate 1-(2-Chlorophenyl)ethyl[3-(4-(2-chloroethyl)phenyl)isoxazolyl]carbamate (481 mg, 1.19 mmol) was dissolved in chloroform (10 ml), methyl thioglycolate (379 mg, 3.57 mmol), and triethylamine (600 mg, 5.93 mmol) were added, and the mixture was stirred overnight at 50° C. The solvent was evaporated under reduced pressure and the residue was purified by silica gel chromatography (hexane:ethyl acetate=4:1) to give the title compound (190 mg, 34%).

MS (ESI) m/z 475 (M+H)$^+$.

(Step 8) Synthesis of {[2-(4-{4-[1-(2-chlorophenyl)ethoxycarbonylamino]-3-isoxazolyl}phenyl)ethyl]thio}acetic acid Reaction similar to that of Example 2 was carried out using methyl {[2-(4-{4-[1-(2-chlorophenyl)ethoxycarbonylamino]-3-isoxazolyl}phenyl)ethyl]thio}acetate (183 mg, 0.385 mmol) to give the title compound (123 mg, 69%).

Example 15

Synthesis of {3-[2-(4-{4-[1-(2-chlorophenyl)ethoxycarbonylamino]-3-isoxazolyl}phenyl)ethyl]thio}propionic acid (Compound 15)

(Step 1) Synthesis of methyl {3-[2-(4-{4-[1-(2-chlorophenyl)ethoxycarbonylamino]-3-isoxazolyl}phenyl)ethyl]thio}propionate Reaction similar to that of Step 7 of Example 14 was carried out using 1-(2-chlorophenyl)ethyl[3-(4-(2-chloroethyl)phenyl)isoxazolyl]carbamate (481 mg, 1.19 mmol) obtained in Step 6 of Example 14 and methyl 3-mercaptopropionate (430 mg, 3.58 mmol) to give the title compound (44 mg, 8%).

MS(ESI) m/z 489(M+H)$^+$.

(Step 2) Synthesis of {3-[2-(4-{4-[1-(2-chlorophenyl)ethoxycarbonylamino]-3-isoxazolyl}phenyl)ethyl]thio}propionic acid Reaction similar to that of Example 2 was carried out using methyl {3-[2-(4-{4-[1-(2-chlorophenyl)ethoxycarbonylamino]-3-isoxazolyl}phenyl)ethyl]thio}propionate (44 mg, 0.090 mmol) to give the title compound (29 mg, 68%).

Example 16

Synthesis of {[2-(4-{4-[1-(2-chlorocyclopentenyl)ethoxycarbonylamino]-3-isoxazolyl}phenyl)ethyl]thio}acetic acid (Compound 16)

(Step 1) Synthesis of 1-(2-chlorocyclopentenyl)ethyl {3-[4-(2-chloroethyl)phenyl]isoxazolyl}carbamate Reaction similar to that of Step B-6 of Example 1 was carried out using 3-(4-(2-chloroethyl)phenyl)isoxazole-4-carboxylic acid (308 mg, 1.22 mmol) and 1-(2-chlorocyclopentenyl)ethanol (270 mg, 1.84 mmol) to give the title compound (482 mg, 100%).

MS(ESI) m/z 395(M+H)$^+$.

(Step 2) Synthesis of methyl {[2-(4-{4-[1-(2-chlorocyclopentenyl)ethoxycarbonylamino]-3-isoxazolyl}phenyl)ethyl]thio}acetate Reaction similar to that of Step 7 of Example 14 was carried out using 1-(2-chlorocyclopentenyl)ethyl {3-[4-(2-chloroethyl)phenyl]isoxazolyl}carbamate (482 mg, 1.22 mmol) to give the title compound (69 mg, 12%).

MS(ESI) m/z 465(M+H)$^+$.

(Step 3) Synthesis of {[2-(4-{4-[1-(2-chlorocyclopentenyl)ethoxycarbonylamino]-3-isoxazolyl}phenyl)ethyl]thio}acetic acid Reaction similar to that of Example 2 was carried out using methyl {[2-(4-{4-[1-(2-chlorocyclopentenyl)ethoxycarbonylamino]-3-isoxazolyl}phenyl)ethyl]thio}acetate (69 mg, 0.148 mmol) to give the title compound (36 mg, 54%).

Example 17

Synthesis of {[2-(4-{4-[1-(2-chlorocyclohexenyl)ethoxycarbonylamino]-3-isoxazolyl}phenyl)ethyl]thio}acetic acid (Compound 17)

(Step 1) Synthesis of 1-(2-chlorocyclohexenyl)ethyl [3-(4-(2-chloroethyl)phenyl)-isoxazolyl]carbamate Reaction similar to that of Step B-6 of Example 1 was carried out using 3-(4-(2-chloroethyl)phenyl)isoxazole-4-carboxylic acid (262 mg, 1.04 mmol) and 1-(2-chlorocyclohexenyl)ethanol (256 mg, 1.59 mmol) to give the title compound (396 mg, 93%).

MS(ESI) m/z 409(M+H)$^+$.

(Step 2) Synthesis of methyl {[2-(4-{4-[1-(2-chlorocyclohexenyl)ethoxycarbonylamino]-3-isoxazolyl}phenyl)ethyl]thio}acetate Reaction similar to that of Step 7 of Example 14 was carried out using 1-(2-chlorocyclohexenyl)ethyl[3-(4-(2-chloroethyl)phenyl)isoxazolyl]carbamate (396 mg, 0.97 mmol) to give the title compound (108 mg, 23%).

MS(ESI) m/z 479(M+H)$^+$.

(Step 3) Synthesis of {[2-(4-{4-[1-(2-chlorocyclohexenyl)ethoxycarbonylamino]-3-isoxazolyl}phenyl)ethyl]thio}acetic acid Reaction similar to that of Example 2 was carried out using methyl {[2-(4-{4-[1-(2-chlorocyclohexenyl)ethoxycarbonylamino]-3-isoxazolyl}phenyl)ethyl]thio}acetate (100 mg, 0.209 mmol) to give the title compound (79 mg, 81%).

Example 18

Synthesis of 3-(4-{4-[1-(2-chlorophenyl)ethoxycarbonylamino]-5-isoxazolyl}benzylsulfanyl)propionic acid (Compound 18)

(Step 1) Synthesis of tert-butyl 3-(tert-butyldimethylsilyl)oxy-3-(4-chloromethylphenyl)propionate Under an argon atmosphere, to a suspension (50 ml) of Bu$_2$Sn(OTf)$_2$ (690 mg, 1.30 mmol) in dichloromethane was added dropwise a solution (10 ml) of 4-chloromethylbenzaldehyde (2.00 g, 12.94 mmol) in dichloromethane at −78° C., then a solution (10 ml) of 1-tert-butoxy-1-[(tert-butyldimethylsilyl)oxy]ethene (6.10 g, 26.47 mmol) in dichloromethane was added dropwise, and the mixture was stirred for 2 hours. Water was added, and the mixture was extracted with dichloromethane. The extract was washed with saturated brine and dried over anhydrous sodium sulfate. The solvent was evaporated under reduced pressure, and the obtained crude product was purified by silica gel chromatography (hexane:ethyl acetate=19:1) to give the title compound (4.96 g, 100%).

(Step 2) Synthesis of tert-butyl 3-hydroxy-3-(4-{[(3-methoxy-3-oxopropyl)thio]-methyl}phenyl)propionate To a solution (40 ml) of tert-butyl 3-(tert-butyldimethylsilyl)oxy-3-(4-chloromethylphenyl)propionate (3.25 g, 8.44 mmol) in chloroform were added methyl 3-mercaptopropionate (1.12 g, 9.32 mmol), triethylamine (2.4 ml, 17.29 mmol), and tetrabutylammonium iodide (156 mg, 0.42 mmol), and the mixture was stirred overnight at 50° C. The solvent was evaporated under reduced pressure and water was added. The mixture was extracted with ethyl acetate, and the extract was washed with saturated brine and dried over anhydrous sodium sulfate. The solvent was evaporated under reduced pressure again. The obtained crude product was dissolved in THF (35 ml), 1M tetrabutylammonium fluoride-THF solution (8.5 ml, 8.50 mmol) was added, and the mixture was stirred at room temperature for 4 hours. The solvent was evaporated under reduced pressure, water was added, and the mixture was extracted with ethyl acetate. The organic layer was washed with saturated brine and dried over anhydrous sodium sulfate. The solvent was evaporated under reduced pressure, and the obtained crude product was purified by silica gel chromatography (hexane:ethyl acetate=3:1) to give the title compound (711 mg, 24%).

(Step 3) Synthesis of tert-butyl 3-(4-{[(3-methoxy-3-oxopropyl)thio]methyl}phenyl)-3-oxopropionate To a solution (15 ml) of tert-butyl 3-hydroxy-3-(4-{[(3-methoxy-3-oxopropyl)thio]methyl}phenyl)propionate (695 mg, 1.96 mmol) in dichloromethane were added sodium acetate (810 mg, 9.87 mmol) and pyridinium dichromate (885 mg, 2.35 mmol), and the mixture was stirred overnight at room temperature. Ethyl ether was added to the reaction mixture, and the mixture was filtered. The filtrate was concentrated under reduced pressure, and the obtained crude product was purified by silica gel chromatography (hexane:ethyl acetate=5:1) to give the title compound (494 mg, 71%).

(Step 4) Synthesis of tert-butyl 5-(4-{[(3-methoxy-3-oxopropyl)thio]methyl}-phenyl)isoxazole-4-carboxylate To tert-butyl 3-(4-{[(3-methoxy-3-oxopropyl)thio]methyl}phenyl)-3-oxopropionate (472 mg, 1.34 mmol) was added N,N-dimethylformamide dimethylacetal (5 ml), and the mixture was stirred at 100° C. for 1 hour. The solvent was evaporated under reduced pressure, and the residue was dissolved in ethanol (10 ml). Hydroxylamine hydrochloride (280 mg, 4.03 mmol) was added, and the mixture was stirred at 70° C. for 2 hours. The solvent was evaporated under reduced pressure and water was added. The mixture was extracted with ethyl acetate, and the extract was washed with saturated brine and dried over anhydrous sodium sulfate. The solvent was evaporated under reduced pressure, and the obtained crude product was purified by silica gel chromatography (hexane:ethyl acetate=5:1) to give the title compound (330 mg, 65%).

(Step 5) Synthesis of 5-(4-{[(3-methoxy-3-oxopropyl)thio]methyl}phenyl)isoxazole-4-carboxylic acid To tert-butyl 5-(4-{[(3-methoxy-3-oxopropyl)thio]methyl}phenyl)isoxazole-4-carboxylate (300 mg, 0.80 mmol) was added 4N hydrogen chloride in 1,4-dioxane (10 ml), and the mixture was stirred overnight at 100° C. The solvent was evaporated under reduced pressure to give the title compound (250 mg, 98%).

(Step 6) Synthesis of methyl 3-(4-[4-[1-(2-chlorophenyl)ethoxycarbonylamino]-5-isoxazolyl]benzylsulfanyl)propionate Reaction similar to that of Step B-6 of Example 1 was carried out using 5-(4-{[(3-methoxy-3-oxopropyl)thio]methyl}phenyl)isoxazole-4-carboxylic acid (81 mg, 0.25 mmol) and 1-(2-chlorophenyl)ethanol (57 mg, 0.36 mmol) to give the title compound (24 mg, 20%).

MS(ESI) m/z 475(M+H)$^+$.

(Step 7) Synthesis of 3-(4-[4-[1-(2-chlorophenyl)ethoxycarbonylamino]-5-isoxazolyl]-benzylsulfanyl) propionic acid To a solution (1 ml) of methyl 3-(4-[4-[1-(2-chlorophenyl)ethoxy-carbonylamino]-5-isoxazolyl]benzylsulfanyl)propionate (22 mg, 0.046 mmol) in ethanol was added 2N hydrochloric acid (2 ml), and the mixture was stirred at 50° C. for 4 hours. The solvent was evaporated under reduced pressure, and water was added. The mixture was extracted with ethyl acetate, and the extract was dried over anhydrous sodium sulfate. The solvent was evaporated under reduced pressure, and the obtained crude product was purified by silica gel chromatography (dichloromethane:methanol=9:1) to give the title compound (10 mg, 47%).

Example 19

Synthesis of 5-(4-{4-[1-(2-chlorophenyl)ethoxycarbonylamino]-3-isoxazolyl}phenyl)-4-pentanoic acid (Compound 19)

(Step 1) Synthesis of 4-iodobenzaldehyde oxime

The title compound (1.58 g, 6.40 mmol, 96.3%) was obtained from 4-iodobenzaldehyde (1.54 g, 6.63 mmol) according to a method similar to that of Step B-2 of Example 1.

MS(ESI) m/z 248(M+H)$^+$.

(Step 2) Synthesis of N-hydroxy-4-iodobenzenecarboxyimidoyl chloride

The title compound (1.79 g, 6.36 mmol, 100%) was obtained from 4-iodobenzaldehyde oxime (1.57 g, 6.36 mmol) according to a method similar to that of Step B-3 of Example 1.

MS(ESI) m/z 282(M+H)$^+$.

(Step 3) Synthesis of methyl 3-(4-iodophenyl)isoxazole-4-carboxylate

The title compound (1.14 g, 3.47 mmol, 54.7%) was obtained from N-hydroxy-4-iodobenzenecarboxyimidoyl chloride (1.79 g, 6.36 mmol) according to a method similar to that of Step B-4 of Example 1.

MS(ESI) m/z 330(M+H)$^+$.

(Step 4) Synthesis of
3-(4-iodophenyl)isoxazole-4-carboxylic acid

The title compound (1.22 g, 3.87 mmol, 100%) was obtained from methyl 3-(4-iodophenyl)isoxazole-4-carboxylate (1.14 g, 3.47 mmol) according to a method similar to that of Step B-5 of Example 1.

MS(ESI) m/z 316(M+H)$^+$.

(Step 5) Synthesis of 1-(2-chlorophenyl)ethyl[3-(4-iodophenyl)-4-isoxazolyl]carbamate The title compound (394 mg, 0.841 mmol, 87.9%) was obtained from 3-(4-iodophenyl)isoxazole-4-carboxylic acid (430 mg, 1.37 mmol) and 2-chloro-α-methyl-benzylalcohol (127 μl, 0.956 mmol) according to the method of Step B-6 of Example 1.

MS(ESI) m/z 469(M+H)$^+$.

(Step 6) Synthesis of methyl 5-(4-{4-[1-(2-chlorophenyl)ethoxycarbonylamino]-3-isoxazolyl}phenyl)-4-pentenoate 1-(2-Chlorophenyl)ethyl[3-(4-iodophenyl)-4-isoxazolyl]carbamate (250 mg, 0.534 mmol) was dissolved in a mixed solvent of diethylisopropylamine (2.5 ml) and 1,4-dioxane (12.5 ml), ethyl 4-pentenate (96 mg, 0.748 mmol), tri-o-tolylphosphine (65 mg, 0.214 mmol), and palladium acetate (12 mg, 0.0534 mmol) were added. The mixture was stirred at 100° C. for 4 hours. 1N Hydrochloric acid was added, and the mixture was extracted with ethyl acetate. The organic layer was washed with saturated aqueous sodium chloride solution and dried over anhydrous sodium sulfate. The solvent was evaporated under reduced pressure to give the title compound (159 mg, 0.340 mmol, 63.6%).

MS(ESI) m/z 469(M+H)$^+$.

(Step 7) Synthesis of methyl 5-(4-{4-[1-(2-chlorophenyl)ethoxycarbonylamino]-3-isoxazolyl}phenyl)-4-pentanoate Methyl 5-(4-{4-[1-(2-chlorophenyl)ethoxycarbonylamino]-3-isoxazolyl}-phenyl)-4-pentenoate (160 mg, 0.299 mmol) was dissolved in ethyl acetate (10 ml), and palladium carbon (dry, 25 mg) was added. The mixture was hydrogenated at room temperature for 1 hour. After filtration through celite, the solvent was evaporated under reduced pressure to give the title compound (148 mg, 0.315 mmol, 92.2%).

MS(ESI) m/z 471(M+H)$^+$.

(Step 8) Synthesis of 5-(4-{4-[1-(2-chlorophenyl)ethoxycarbonylamino]-3-isoxazolyl}phenyl)-4-pentanoic acid The title compound (63.3 mg, 0.143 mmol, 73.3%) was obtained from methyl 5-(4-{4-[1-(2-chlorophenyl)ethoxycarbonylamino]-3-isoxazolyl}phenyl)-4-pentanoate (92 mg, 0.195 mmol) according to the method of Example 2.

Example 20

Synthesis of 3-(4-{4-[1-(2-chlorophenyl)ethoxycarbonylamino]-3-isoxazolyl}benzyloxycarbonylamino) propionic acid (Compound 20)

(Step 1) Synthesis of methyl 3-(4-{4-[1-(2-chlorophenyl)ethoxycarbonylamino]-3-isoxazolyl}benzyloxycarbonylamino)propionate 1-(2-Chlorophenyl)ethyl[3-(4-chloromethylphenyl)-4-isoxazolyl]carbamate (1.0 g, 2.56 mmol) obtained in Step B-6 of Example 1 was dissolved in N,N-dimethylformamide (30 ml), methyl 3-aminopropionate hydrochloride (1.07 g, 7.67 mmol) and potassium carbonate (2.12 g, 15.3 mmol) were added, and the mixture was stirred overnight at 50° C. 1N Hydrochloric acid was added at 0° C. to weak-acidify the reaction system, and the mixture was extracted 3 times with ethyl acetate. The organic layer was washed with saturated aqueous sodium hydrogencarbonate solution and saturated aqueous sodium chloride solution, and dried over anhydrous sodium sulfate. The solvent was evaporated under reduced pressure, and the residue was purified by column chromatography (methanol:dichloromethane=1:20) to give the title compound (138 mg, 11%).

MS(ESI) m/z 502(M+H)$^+$.

(Step 2) Synthesis of 3-(4-{4-[1-(2-chlorophenyl)ethoxycarbonylamino]-3-isoxazolyl}benzyloxycarbonylamino)propionic acid The title compound (94.6 mg, quant.) was obtained from methyl 3-(4-{4-[1-(2-chlorophenyl)ethoxycarbonylamino]-3-isoxazolyl}benzyloxycarbonylamino)propionate (97.5 mg, 0.194 mmol) according to a method similar to that of Example 2.

Example 21

Synthesis of 4-[(4-{4-[1-(2-chlorophenyl)ethoxycarbonylamino]-3-isoxazolyl}phenyl)amino]-(2R)-2-hydroxy-4-oxobutanoic acid (Compound 21)

(2R)-2-Acetoxy-4-[(4-{4-[1-(2-chlorophenyl)ethoxycarbonylamino]-3-isoxazolyl}phenyl)amino]-4-oxobutanoic acid (132 mg, 0.256 mmol) was dissolved in methanol (2.5 ml), 1N aqueous sodium hydroxide solution (2.5 ml) was added, and the mixture was stirred at room temperature for 1 hour. 1N Hydrochloric acid (2.6 ml) was added at 0° C. to weak-acidify the reaction system, and the mixture was extracted with ethyl acetate. The organic layer was washed with saturated aqueous sodium chloride solution and dried over anhydrous sodium sulfate. The solvent was evaporated under reduced pressure to give the title compound (111 mg, 92%).

Example 22

Synthesis of 4-[4-({[1-(2-chlorophenyl)ethoxy]carbonyl}amino)-3-isoxazolyl]phenyl acetate (Compound 22)

(Step 1) Synthesis of
4-(tert-butyldimethylsilyloxy)benzaldehyde oxime

Reaction similar to that of Step B-2 of Example 1 was carried out using 4-(tert-butyldimethylsilyloxy)benzaldehyde to give the title compound.

(Step 2) Synthesis of 4-(tert-butyldimethylsilyloxy)-N-hydroxybenzenecarboxyimidoyl chloride Reaction similar to that of Step B-3 of Example 1 was carried out using 4-(tert-butyldimethylsilyloxy)benzaldehyde oxime to give the title compound.

(Step 3) Synthesis of methyl 3-(4-[tert-butyldimethylsilyloxy]phenyl)isoxazole-4-carboxylate Reaction similar to that of Step B-4 of Example 1 was carried out using 4-(tert-butyldimethylsilyloxy)-N-hydroxybenzenecarboxyimidoyl chloride to give the title compound.

(Step 4) Synthesis of
3-(4-hydroxyphenyl)isoxazole-4-carboxylic acid

Reaction similar to that of Step B-5 of Example 1 was carried out using methyl 3-(4-[tert-butyldimethylsilyloxy] phenyl)isoxazole-4-carboxylate to give the title compound.

(Step 5) Synthesis of
3-(4-acetoxyphenyl)isoxazole-4-carboxylic acid

To a solution (120 ml) of 3-(4-hydroxyphenyl)isoxazole-4-carboxylic acid (1.39 g, 6.77 mmol) in dichloromethane were added acetic anhydride (2.07 g, 20.28 mmol), triethylamine (3.43 g, 33.90 mmol), and 4-N,N-dimethylaminopyridine (84 mg, 0.676 mmol), and the mixture was stirred at room temperature for 1 hour. The reaction mixture was concentrated under reduced pressure and water was added. The mixture was extracted with ethyl acetate, washed with saturated brine, and dried over anhydrous sodium sulfate. The solvent was evaporated under reduced pressure, and the obtained crude product was purified by silica gel column chromatography (ethyl acetate) to give the title compound (1.50 g, 78%).

(Step 6) Synthesis of 4-[4-({[1-(2-chlorophenyl) ethoxy]carbonyl}amino)-3-isoxazolyl]phenyl acetate Reaction similar to that of Step B-6 of Example 1 was carried out using 3-(4-acetoxyphenyl)isoxazole-4-carboxylic acid to give the title compound.

Example 23

Synthesis of 1-(2-chlorophenyl)ethyl 3-(4-hydroxyphenyl)-4-isoxazolylcarbamate (Compound 23)

To a solution (20 ml) of 4-[4-({[1-(2-chlorophenyl)ethoxy] carbonyl}amino)-3-isoxazolyl]phenyl acetate (2.11 g, 5.26 mmol) in tetrahydrofuran was added 1M aqueous sodium hydroxide solution (7.0 ml), and the mixture was stirred at room temperature for 7 hours. The reaction mixture was concentrated under reduced pressure, and water was added. The mixture was neutralized with 1M hydrochloric acid and extracted with ethyl acetate. The organic layer was washed with saturated brine and dried over anhydrous sodium sulfate. The solvent was evaporated under reduced pressure to give the title compound (1.82 g, 96%).

Example 24

Synthesis of 5-(4-{4-[1-(2-chlorophenyl)ethoxycarbonylamino]-3-isoxazolyl}phenoxy)pentanoic acid (Compound 24)

(Step 1) Synthesis of ethyl 5-(4-{4-[1-(2-chlorophenyl)ethoxycarbonylamino]-3-isoxazolyl}phenoxy) pentanoate To a solution (2 ml) of 1-(2-chlorophenyl)ethyl 3-(4-hydroxyphenyl)-4-isoxazolylcarbamate (80 mg, 0.223 mmol) in N,N-dimethylformamide were added potassium carbonate (60 mg, 0.435 mmol) and ethyl 5-bromovalerate (60 mg, 0.287 mmol), and the mixture was stirred at 100° C. for 1 hour. Water was added, the mixture was extracted with ethyl acetate, and the extract was washed with saturated brine and dried over anhydrous sodium sulfate. The solvent was evaporated under reduced pressure, and the obtained residue was purified by silica gel column chromatography (hexane:ethyl acetate=4:1) to give the title compound (59 mg, 55%).

(Step 2) Synthesis of 5-(4-{4-[1-(2-chlorophenyl) ethoxycarbonylamino]-3-isoxazolyl}phenoxy)pentanoic acid The title compound (31 mg, 57%) was obtained from ethyl 5-(4-{4-[1-(2-chlorophenyl)ethoxycarbonylamino]-3-isoxazolyl}phenoxy)pentanoate (58 mg, 0.12 mmol) according to a method similar to that of Example 2.

Example 25

Synthesis of 4-[(4-{4-[1-(2-chlorophenyl)ethoxycarbonylamino]-3-isoxazolyl}phenyl)amino]-4-oxobutanoic acid (Compound 25)

(Step 1) Synthesis of 4-nitrobenzaldehyde oxime

Reaction similar to that of Step B-2 of Example 1 was carried out using 4-nitrobenzaldehyde to give the title compound.

(Step 2) Synthesis of
N-hydroxy-4-nitrobenzenecarboxyimidoyl chloride

Reaction similar to that of Step B-3 of Example 1 was carried out using 4-nitrobenzaldehyde oxime to give the title compound.

(Step 3) Synthesis of methyl
3-(4-nitrophenyl)isoxazole-4-carboxylate

Reaction similar to that of Step B-4 of Example 1 was carried out using N-hydroxy-4-nitrobenzenecarboxyimidoyl chloride to give the title compound.

(Step 4) Synthesis of
3-(4-nitrophenyl)isoxazole-4-carboxylic acid

Reaction similar to that of Step B-5 of Example 1 was carried out using methyl 3-(4-nitrophenyl)isoxazole-4-carboxylate to give the title compound.

(Step 5) Synthesis of 1-(2-chlorophenyl)ethyl[3-(4-nitrophenyl)-4-isoxazolyl]carbamate Reaction similar to that of Step B-6 of Example 1 was carried out using 3-(4-nitrophenyl)isoxazole-4-carboxylic acid to give the title compound.

(Step 6) Synthesis of 1-(2-chlorophenyl)ethyl[3-(4-aminophenyl)-4-isoxazolyl]carbamate To a solution of 1-(2-chlorophenyl)ethyl[3-(4-nitrophenyl)-4-isoxazolyl]-carbamate in ethanol was added 5% Pd—C, and hydrogenation reaction was carried out at room temperature for 1 hour. The reaction mixture was filtered, and the filtrate was concentrated under reduced pressure and purified by silica gel column chromatography (hexane:ethyl acetate=3:1) to give the title compound.

(Step 7) Synthesis of 4-[(4-{4-[1-(2-chlorophenyl) ethoxycarbonylamino]-3-isoxazolyl}phenyl)amino]-4-oxobutanoic acid 1-(2-Chlorophenyl)ethyl[3-(4-aminophenyl)-4-isoxazolyl]carbamate and succinic anhydride were dissolved in acetone, and the mixture was stirred overnight at room temperature. The reaction mixture was concentrated under reduced pressure, and the residue was purified by reversed phase HPLC to give the title compound.

Example 26

Synthesis of (2R)-2-acetoxy-4-[(4-{4-[1-(2-chlorophenyl)ethoxy-carbonylamino]-3-isoxazolyl}phenyl)amino]-4-oxobutanoic acid (Compound 26)

The title compound (188 mg, 87%) was obtained from 1-(2-chlorophenyl)ethyl [3-(4-aminophenyl)-4-isoxazolyl] carbamate (150 mg, 0.42 mmol) obtained in Step 6 of Example 25 and (S)-(−)-O-2-acetoxysuccinic anhydride (133 mg, 0.84 mmol) according to a method similar to that of Step 7 of Example 25.

Example 27

Synthesis of {[2-(4-{4-[(1R)-1-(2-chlorophenyl)ethoxycarbonylamino]-3-isoxazolyl}phenyl)ethyl]thio}acetic acid (Compound 27)

Reaction similar to that of Example 14 was carried out using (1R)-1-(2-chlorophenyl)ethanol to give the title compound.

Example 28

Synthesis of 3-(4-{4-[(1R)-1-(2-chlorophenyl)ethoxycarbonylamino]-3-isoxazolyl}benzylsulfonyl)propionic acid (Compound 28)

Reaction similar to that of Example 11 was carried out using (1R)-1-(2-chlorophenyl)ethanol to give the title compound.

Example 29

Synthesis of {3-[2-(4-{4-[(1R)-1-(2-chlorophenyl)ethoxycarbonylamino]-3-isoxazolyl}phenyl)ethyl]thio}propionic acid (Compound 29)

Reaction similar to that of Example 15 was carried out using (1R)-1-(2-chlorophenyl)ethanol to give the title compound.

Example 30

Synthesis of 5-(4-{4-[(1R)-1-(2-chlorophenyl)ethoxycarbonylamino]-3-isoxazolyl}phenyl)-4-pentenoic acid (Compound 30)

According to methods similar to those of Step 5 and Step 6 of Example 19 using 3-(4-iodophenyl)isoxazole-4-carboxylic acid and (R)-2-chloro-α-methylbenzyl alcohol, methyl 5-(4-{4-[(1R)-1-(2-chlorophenyl)ethoxycarbonylamino]-3-isoxazolyl}phenyl)-4-pentenoate was synthesized, which was reacted in the same manner as in Example 2 to give the title compound.

Example 31

Synthesis of 5-(4-{4-[(1R)-1-(2-chlorophenyl)ethoxycarbonylamino]-3-isoxazolyl}phenyl)-4-pentanoic acid (Compound 31)

Reactions similar to those of Step 7 and Step 8 of Example 19 were carried out using methyl 5-(4-{4-[(1R)-1-(2-chlorophenyl)ethoxycarbonylamino]-3-isoxazolyl}phenyl)-4-pentenoate obtained in Example 30 to give the title compound.

Example 32

Synthesis of 6-(4-{4-[(1R)-1-(2-chlorophenyl)ethoxycarbonylamino]-3-isoxazolyl}phenyl)hexanoic acid (Compound 32)

(Step 1) Synthesis of 3-[4-(5-methoxycarbonyl-1-pentenyl)phenyl]isoxazole-4-carboxylic acid 3-(4-Iodophenyl)isoxazole-4-carboxylic acid (315 mg, 1.0 mmol) was dissolved in a mixed solvent of 1,4-dioxane (5 ml) and diethylisopropylamine (2.5 ml), methyl 5-hexenoate (179 mg, 1.4 mmol), tri-(o-tolyl)phosphine (122 mg, 0.4 mmol) and palladium acetate (22.4 mg, 0.1 mmol) were added, and the mixture was stirred overnight at 100° C. 1N Hydrochloric acid was added, and the mixture was extracted once with ethyl acetate. The organic layer was washed with saturated aqueous sodium chloride solution and dried over anhydrous sodium sulfate. The solvent was evaporated under reduced pressure, and the residue was purified by silica gel chromatography (hexane:ethyl acetate=7:3-6:4) to give the title compound (250 mg, 79%).

MS(ESI) m/z 316(M+H)$^+$.

(Step 2) Synthesis of methyl 6-(4-{4-[(1R)-1-(2-chlorophenyl)ethoxycarbonylamino]-3-isoxazolyl}phenyl)-5-hexenoate The title compound (99 mg, 27%) was obtained from 3-[4-(5-methoxycarbonyl-1-pentenyl)phenyl]isoxazole-4-carboxylic acid (250 mg, 0.79 mmol) and (1R)-1-(2-chlorophenyl)ethanol (149 mg, 0.95 mmol) according to methods similar to those of Step 5 and Step 6 of Example 19.

MS(ESI) m/z 469(M+H)$^+$.

(Step 3) Synthesis of 6-(4-{4-[(1R)-1-(2-chlorophenyl)ethoxycarbonylamino]-3-isoxazolyl}phenyl) hexanoic acid Reactions similar to those of Step 7 and Step 8 of Example 19 were carried out using methyl 6-(4-{4-[(1R)-1-(2-chlorophenyl)ethoxycarbonylamino]-3-isoxazolyl}-phenyl)-5-hexenoate to give the title compound.

Example 33

Synthesis of 5-(4-{4-[1-(2-chlorophenyl)ethoxycarbonylamino]-3-isoxazolyl}phenyl)-3,3-dimethylpentanoic acid (Compound 33)

Reactions similar to those of Step 6 to 8 of Example 19 were carried out using 1-(2-chlorophenyl)ethyl[3-(4-iodophenyl)-4-isoxazolyl]carbamate and methyl 3,3-dimethyl-4-pentenoate to give the title compound.

Example 34

Synthesis of 5-(4-{4-[(1R)-1-(2-chlorophenyl)ethoxycarbonylamino]-3-isoxazolyl}phenyl)-2-methylpentanoic acid (compound 34)

Reactions similar to those of Step 6 to 8 of Example 19 were carried out using 1-(2-chlorophenyl)ethyl[3-(4-iodophenyl)-4-isoxazolyl]carbamate and ethyl 2-methyl-4-pentenoate to give the title compound.

The structural formulas and physicochemical data of the compounds of Example 1 to 34 are shown in Table 4 to 10. In the Tables, the following abbreviations are used. Ex: Example No., Dat: physicochemical data.

Experimental Example 1

(1) Establishment of Myofibroblast Like Cell Strain Derived from Rat Hepatic Stellate Cell Fraction A stellate cell fraction was obtained from the liver of male Wistar rat according to a conventional method (*European J. Biochem.*, 1993, vol. 213, p. 815). After subculture for several generations, the cell was cloned by limiting dilution. Well grown 24 clones that formed colonies were isolated. These clones were stained with αSMA antibody and confirmed to be all positive and to have Myofibroblast like properties. The $Ca^{2+}$ increase, cell growth, and the like, stimulated by LPA were examined in these clones and one kind of clone superior in the reactivity with LPA was selected and used for the measurement of activity in the following Examples.

(2) Measurement of Cell Activation (Intracellular $Ca^{2+}$ Concentration Increasing Action)-Inhibitory Activity The above-mentioned cells were cultured overnight in a 384 well plate at 24,000 cells/well and the medium was removed. An assay buffer (0.1% BSA, 20 mM HEPES, 1×HBSS, 2.5 mM Probenecid) containing 4 μM of Fluo-3, AM (Biotium) was added, and the cells were stained at 37° C. for 1 hour. Following the buffer containing the dye reagent was removed, and an assay buffer was added, intracellular $Ca^{2+}$ concentration was measured with FLIPR (Molecular Devices). Adding a test substance and LPA at the final concentration of 5 μM, the inhibitory action of the test substance on the increase in the intracellular $Ca^{2+}$ concentration by LPA was examined. The increase in the intracellular $Ca^{2+}$ concentration by LPA addition without test substance was taken as 100%, that without the addition of LPA was taken as 0%, and the substrate's concentration ($IC_{50}$) at inhibiting increase in the intracellular $Ca^{2+}$ concentration by 50% was determined.

The results are summarized in Table 11.

TABLE 1

| No. | R1 |
|---|---|
| 1 | 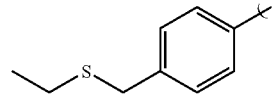 |
| 2 | 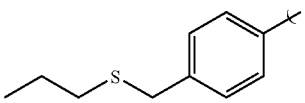 |
| 3 | 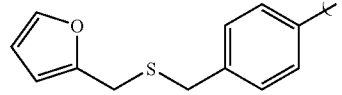 |
| 4 | 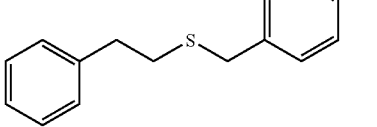 |

TABLE 1-continued

| No. | R1 |
|---|---|
| 5 | 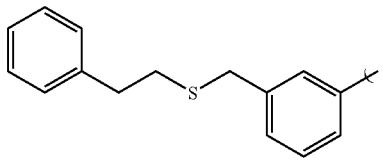 |
| 6 | 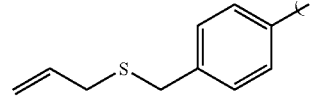 |
| 7 | 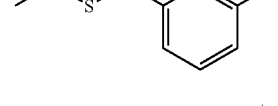 |
| 8 | 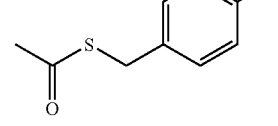 |
| 9 | 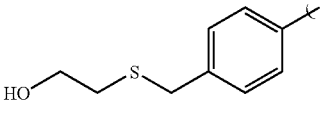 |
| 10 | 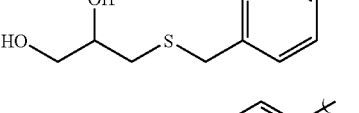 |
| 11 | 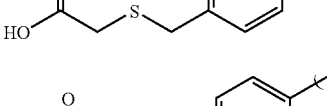 |
| 12 | 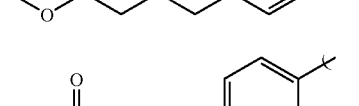 |
| 13 |  |
| 14 | 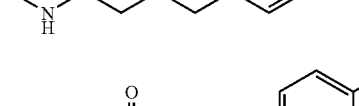 |
| 15 |  |

TABLE 1-continued
| No. | R1 |
|---|---|
| 16 | 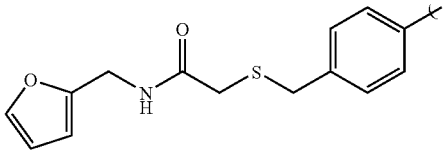 |
| 17 | 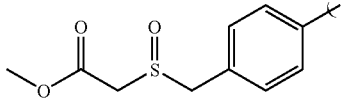 |
| 18 | 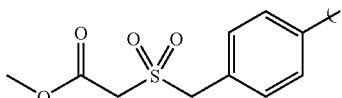 |
| 19 | 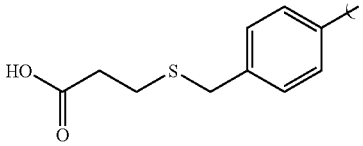 |
| 20 | 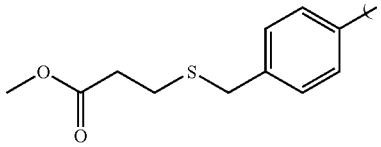 |
| 21 | 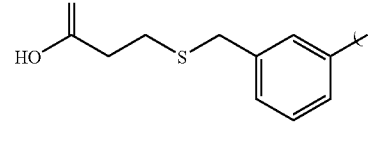 |
| 22 | 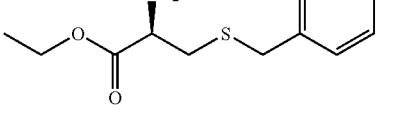 |
| 23 | 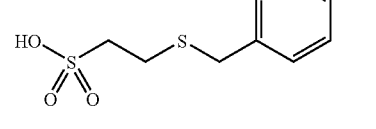 |
| 24 | 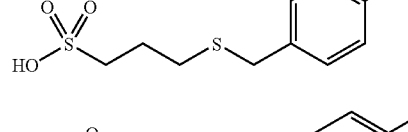 |
| 25 | 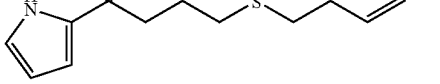 |
TABLE 1-continued
| No. | R1 |
|---|---|
| 26 | 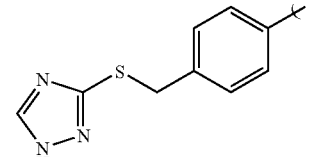 |
| 27 | 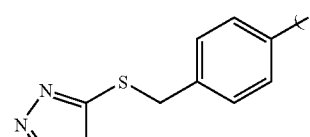 |
| 28 | 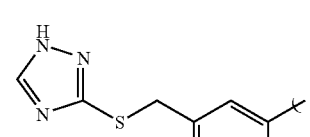 |
| 29 | 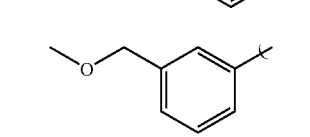 |
| 30 | 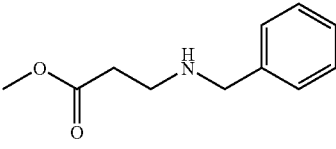 |
| 31 | 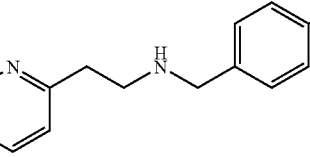 |
| 32 | 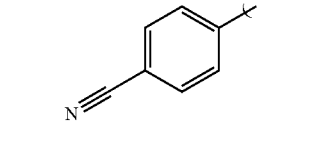 |
| 33 | 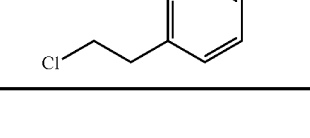 |
TABLE 2
| No. | R1 |
|---|---|
| 34 | 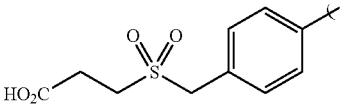 |

TABLE 2-continued
| No. | R1 |
|---|---|
| 35 | 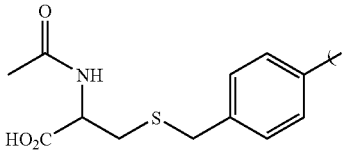 |
| 36 | 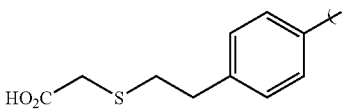 |
| 37 | 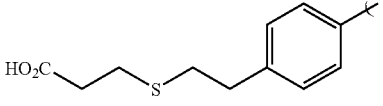 |
| 38 | 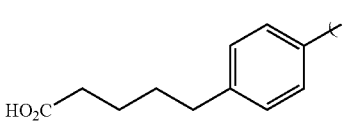 |
| 39 | 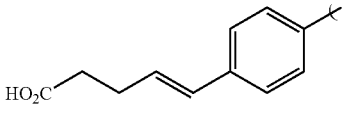 |
| 40 | 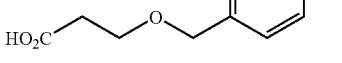 |
| 41 | 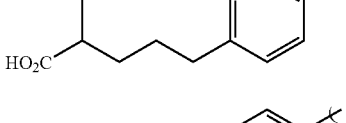 |
| 42 | 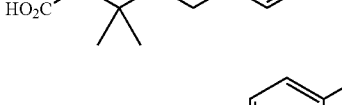 |
| 43 | 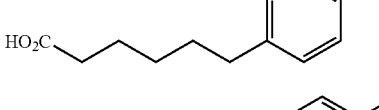 |
| 44 | 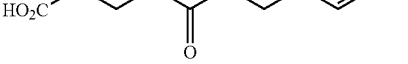 |
| 45 | 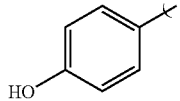 |
| 46 | 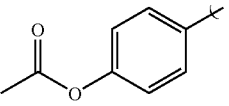 |
| 47 | 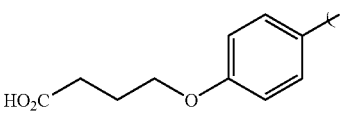 |
| 48 | 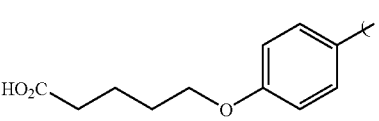 |
| 49 | 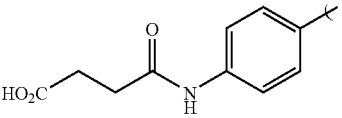 |
| 50 | 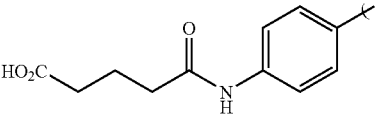 |
| 51 | 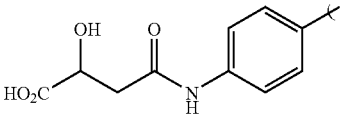 |
| 52 | 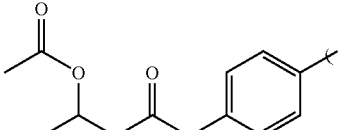 |
TABLE 3
| No. | R3 |
|---|---|
| 1 | 1-(2-fluorophenyl)ethyl |
| 2 | 1-(2-bromophenyl)ethyl |
| 3 | 1-(2-chlorophenyl)ethyl |
| 4 | 2,2,2-trifluoro-1-phenylethyl |
| 5 | 1-(2-chloro-1-cyclopentenyl)ethyl |
| 6 | 1-(2-chloro-1-cyclohexenyl)ethyl |
| 7 | 1-(4-chloro-3-thienyl)ethyl |

TABLE 4

| Ex | Structure | Dat |
|---|---|---|
| 1 | 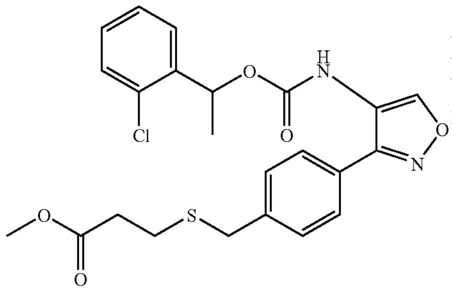 | $^1$H-NMR (300 MHz, CDCl$_3$) δ = 1.58(3H, d, J=6.3 Hz), 2.59(2H, t, J=6.9 Hz), 2.74(2H, t, J=6.9 Hz), 3.69(3H, s), 3.80(2H, s), 6.25(1H, q, J=6.6 Hz), 6.35-6.45(1H, m), 7.15-7.60(8H, m), 8.85-8.95(1H, m).<br>MS(ESI) m/z 475(M + H)$^+$. |
| 2 | 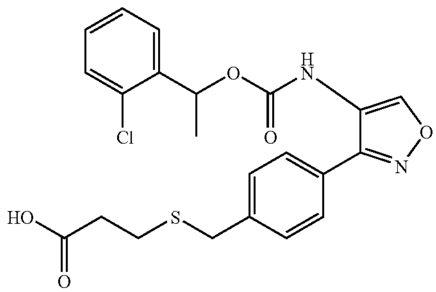 | $^1$H-NMR(300 MHz CDCl$_3$) δ = 1.58(3H, d, J=6.6 Hz), 2.55-2.78(6H, m), 3.81(2H, s), 6.24(1H, q, J=6.6 Hz), 6.37-6.45(1H, m), 7.20-7.60(8H, m), 8.85-8.95(1H, m).<br>MS(ESI) m/z 461 (M + H)$^+$. |
| 3 | 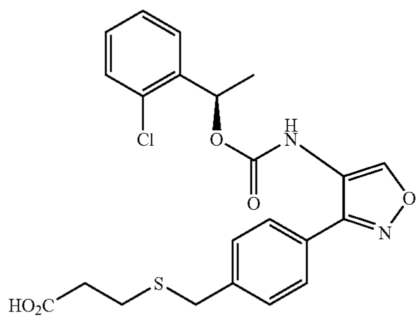 | $^1$H-NMR(300 MHz, CDCl$_3$) δ = 1.58(3H, d, J=6.6 Hz), 2.55-2.78(4H, m), 3.80(2H, s), 6.24 (1H, q, J=6.6 Hz), 6.37-6.45(1H, m), 7.20-7.60(8H, m), 8.85-8.95(1H, m).<br>MS (ESI) m/z 461(M + H)$^+$.<br>[α]$_D$ = 39.5° (MeOH, c = 0.585) |
| 4 | 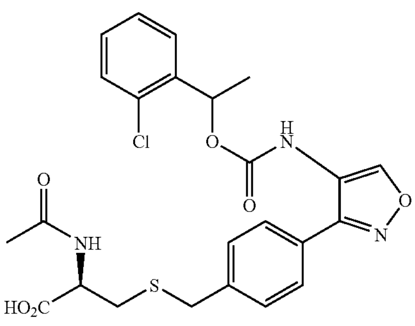 | $^1$H-NMR(300 MHz, CD$_3$OD) δ 1.53(3H, d, J=5.4 Hz), 2.00(3H, s), 2.81(1H, dd, J=13.8, 7.2 Hz), 3.00(1H, dd, J=13.8, 4.5 Hz), 3.83(2H, s), 4.43-4.50(1H, m), 6.12-6.20(1H, m), 7.22-7.65(8H, m), 8.84(1H, s).<br>MS(ESI) m/z 518(M + H)$^+$. |
| 5 | 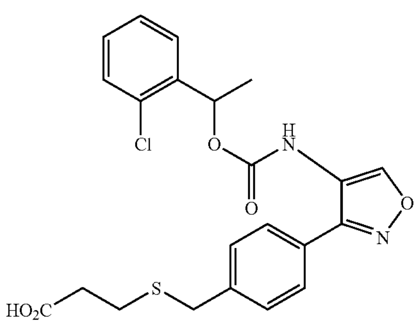 | $^1$H-NMR(300 MHz, CD$_3$OD) δ = 1.53(3H, d, J=6.3 Hz), 2.76-2.86(2H, m), 2.98-3.06(2H, m), 3.82(2H, s), 6.15(1H, q, J=6.3 Hz), 7.22-7.70(8H, m), 8.84(1H, s).<br>MS(ESI) m/z 497(M + H)$^+$. |

TABLE 5

| Ex | Structure | Dat |
|---|---|---|
| 6 | 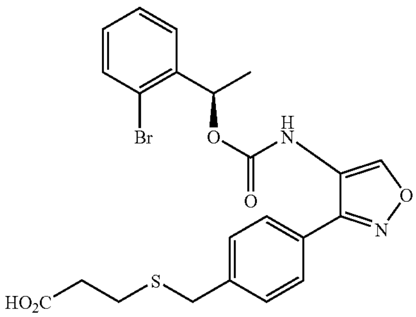 | $^1$H-NMR(300 MHz, CDCl$_3$) δ = 1.57(3H, d, J=6.6 Hz), 2.59-2.66(2H, m), 2.70-2.77(2H, m), 3.80(2H, s), 6.19(1H, q, J=6.6 Hz), 6.45(1H, brs), 7.14-7.59(8H, m), 8.91(1H, s).<br>MS(ESI) m/z 505(M + H)$^+$., 507(M + 2 + H)$^+$. |
| 7 | 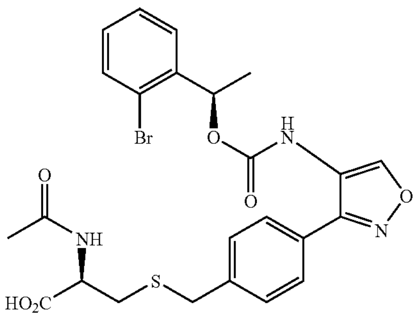 | $^1$H-NMR(300 MHz, CDCl$_3$) δ = 1.56(3H, d, J=6.6 Hz), 2.05(3H, s), 2.82-3.08(2H, m), 3.80(2H, s), 4.42-4.52(1H, m), 6.17(1H, q, J=6.6 Hz), 6.57(1H, brs), 7.12-7.60(8H, m), 8.91(1H, s).<br>MS(ESI) m/z 562(M + H)$^+$., 564(M + 2 + H)$^+$. |
| 8 | 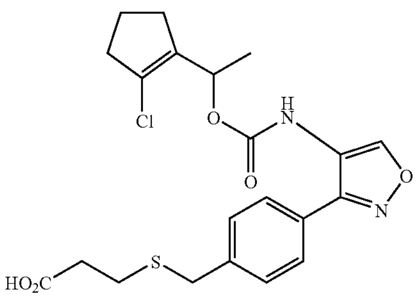 | $^1$H-NMR(300 MHz, CDCl$_3$) δ = 1.37(3H, d, J=6.6 Hz), 1.94(2H, qui, J=7.5 Hz), 2.30-2.78(8H, m), 3.80(2H, s), 5.77(1H, q, J=6.6Hz), 6.25-6.37(1H, m), 7.45-7.60(4H, m), 8.90-8.98(1H, m).<br>MS (ESI) m/z 451(M + H)$^+$. |
| 9 | 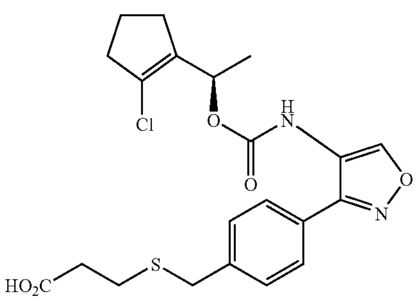 | $^1$H-NMR(300 MHz, CDCl$_3$) δ = 1.37(3H, d, J=6.6 Hz), 1.94(2H, qui, J=7.5 Hz), 2.30-2.78(8H, m), 3.80(2H, s), 5.77(1H, q, J=6.6 Hz), 6.25-6.37(1H, m), 7.45-7.60(4H, m), 8.90-8.98(1H, m).<br>MS(ESI) m/z 451(M + H)$^+$.<br>[α]$_D$ = −33.4° (MeOH, c = 0.815) |
| 10 | 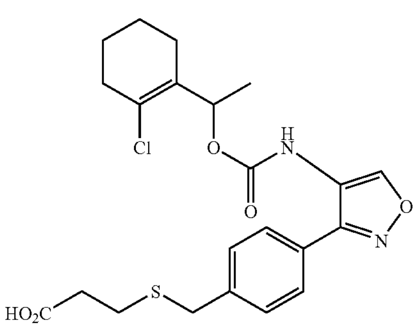 | $^1$H-NMR(300 MHz, CDCl$_3$) δ = 1.35(3H, d, J=6.6 Hz), 1.50-2.76(12H, m), 3.80(2H, s), 5.97(1H, q, J=6.3 Hz), 6.22-6.35(1H, m), 7.45-7.60(4H, m), 8.90-8.98(1H, m).<br>MS(ESI) m/z 465(M + H)$^+$. |

TABLE 6

| Ex | Structure | Dat |
|---|---|---|
| 11 | 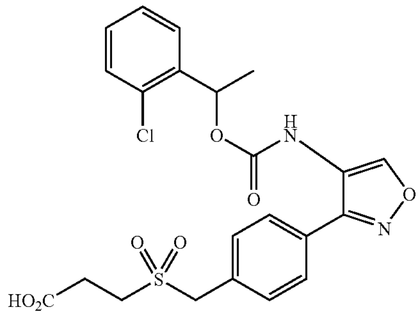 | ¹H-NMR(300 MHz, CD₃OD) δ = 1.58(3H, d, J=6.6 Hz), 2.80(2H, t, J=7.5 Hz), 3.38(2H, t, J=7.5 Hz), 4.52(2H, s), 6.16(1H, q, J=6.6 Hz), 7.22-7.75(8H, m), 8.87(1H, s).<br>MS(ESI) m/z 493(M + H)⁺. |
| 12 | 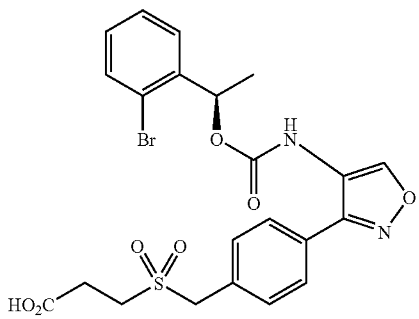 | ¹H-NMR(300 MHz, CD₃OD) δ = 1.52(3H, m), 2.81 (2H, t, J=4.8 Hz), 3.36(2H, t, J=4.8 Hz), 4.53(2H, s), 6.08(1H, m), 7.17(1H, m), 7.35-7.78(8H, m), 8.87(1H, s).<br>MS(ESI) m/z 537(M + H)⁺., 539(M + 2 + H)⁺. |
| 13 | 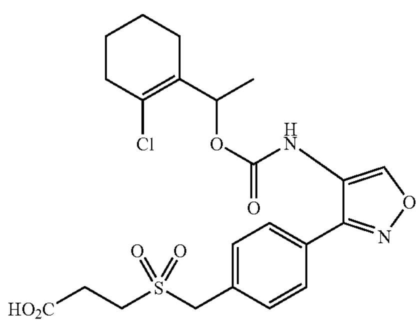 | ¹H-NMR(300 MHz, CD₃OD) δ = 1.32(3H, d, J=6.3 Hz), 1.50-1.68(4H, m), 2.05-2.12(2H, m), 2.28-2.39(2H, m), 2.81(2H, t, J=7.5 Hz), 3.37(2H, t, J=7.5 Hz), 4.53(2H, s), 5.85(1H, brs), 7.43-7.78(4H, m), 8.87(1H, s).<br>MS(ESI) m/z 497(M + H)⁺. |
| 14 | 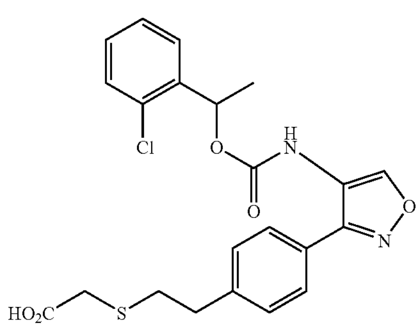 | ¹H-NMR(300 MHz, CDCl₃) δ = 1.55(3H, d, J=6.0 Hz), 2.95(4H, s), 3.25(2H, s), 6.21(1H, q, J=6.0 Hz), 6.67(1H, brs), 7.15-7.56(8H, m), 8.44(1H, brs), 8.86(1H, s).<br>MS(ESI) m/z 461(M + H)⁺. |

TABLE 6-continued

| Ex | Structure | Dat |
|---|---|---|
| 15 | 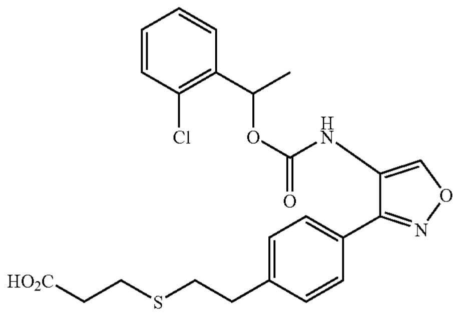 | ¹H-NMR(300 MHz, CDCl₃) δ = 1.59(3H, d, J=6.6 Hz), 2.66-3.01(8H, m), 6.24(1H, q, J=6.6 Hz), 6.53(1H, brs), 7.20-7.59(8H, m), 8.89(1H, s). MS(ESI) m/z 475(M + H)⁺. |

TABLE 7

| Ex | Structure | Dat |
|---|---|---|
| 16 | 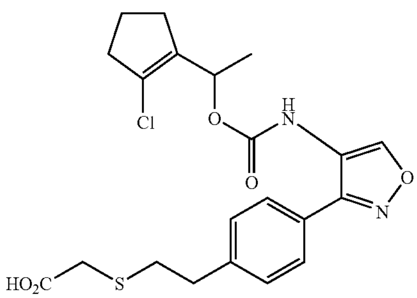 | ¹H-NMR(300 MHz, CDCl₃) δ = 1.35(3H, d, J=6.6 Hz), 1.87-1.98(2H, m), 2.35-2.48(2H, m), 2.52-2.64(2H, m), 2.93-3.03(4H, m), 3.27(2H, s), 5.76(1H, q, J=6.6 Hz), 6.36(1H, brs), 7.36(2H, d, J=7.5 Hz), 7.53(2H, d, J=7.5 Hz), 8.92(1H, s). MS(ESI) m/z 451(M + H)⁺ |
| 17 | 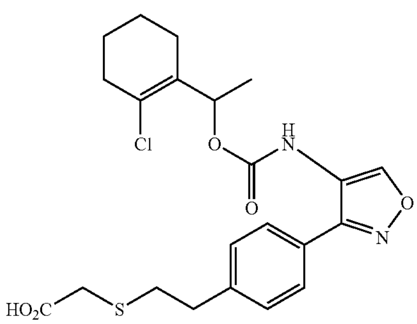 | ¹H-NMR(300 MHz, CDCl₃) δ = 1.34(3H, d, J=6.6 Hz), 1.55-1.72(4H, m), 2.05-2.12(2H, m), 2.33-2.39(2H, m), 2.93-3.03(4H, m), 3.28(2H, s), 5.96(1H, q, J=6.6 Hz), 6.31(1H, brs), 7.38(2H, d, J=7.8 Hz), 7.54(2H, d, J=7.8 Hz), 8.94(1H, s). MS(ESI) m/z 465(M + H)⁺ |
| 18 | 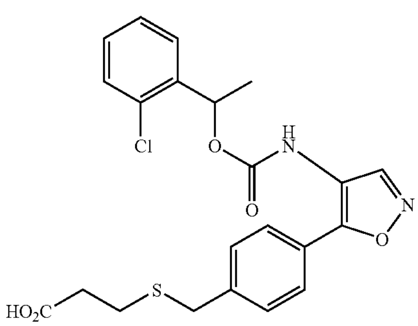 | ¹H-NMR(300 MHz, CDCl₃) δ = 1.54-1.62(3H, m), 2.56-2.65(2H, m), 2.67-2.72(2H, m), 3.78(2H, s), 6.26(1H, q, J=6.6 Hz), 6.48(1H, brs), 7.22-7.68(8H, m), 8.72(1H, s). MS(ESI) m/z 461(M + H)⁺. |

TABLE 7-continued

| Ex | Structure | Dat |
|----|-----------|-----|
| 19 | 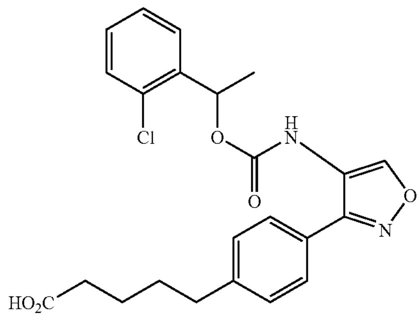 | $^1$H-NMR(300 MHz, DMSO-d$_6$) δ = 1.42-1.66(7H, m), 2.23(2H, t, J=6.9 Hz), 2.63(2H, t, J=6.9 Hz), 5.90-6.02(1H, m), 7.20-7.52(8H, m), 9.06(1H, s), 9.25-9.35(1H, m). MS(ESI) m/z 443(M + H)$^+$. |

TABLE 8

| Ex | Structure | Dat |
|----|-----------|-----|
| 20 | 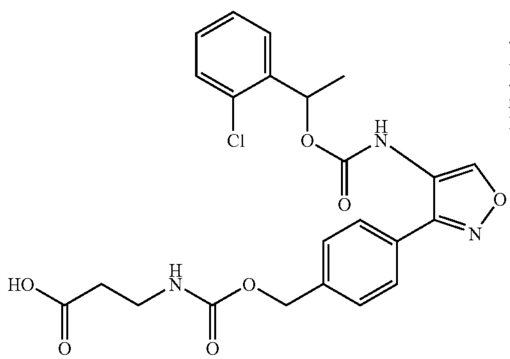 | $^1$H-NMR(300 MHz, CDCl$_3$) δ = 1.57(3H, d, J=6.6 Hz), 2.53-2.67(2H, m), 3.40-3.55(2H, m), 5.17(2H, s), 5.25-5.38(1H, m), 6.24(1H, q, J=6.6 Hz), 6.38-6.48(1H, m), 7.18-7.65(8H, m), 8.85-8.95(1H, m). MS(ESI) m/z 488(M + H)$^+$. |
| 21 | 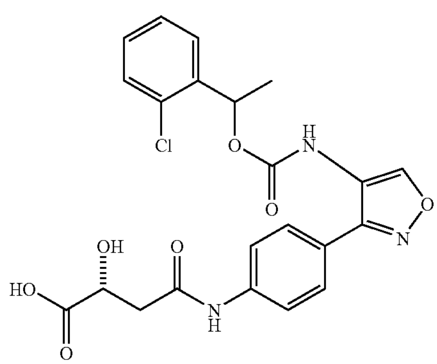 | $^1$H-NMR(300 MHz, CDCl$_3$) δ = 1.54(3H, d, J=6.3 Hz), 2.67-3.07(2H, m), 4.43-4.60(1H, m), 6.12-6.25(1H, m), 6.78-6.88(1H, m), 7.15-7.67(8H, m), 8.78-8.88(1H, m), 8.94(1H, s). MS(ESI) m/z 474(M + H)$^+$. |
| 22 | 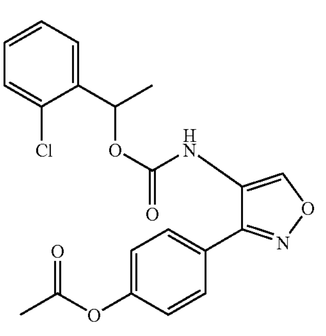 | $^1$H-NMR(300 MHz, CDCl$_3$) δ = 1.58(3H, d, J=6.3 Hz), 2.35(3H, s), 6.24(1H, q, J=6.3 Hz), 6.43(1H, brs), 7.20-7.68(8H, m), 8.90(1H, s). MS(ESI) m/z 401(M + H)$^+$. |

TABLE 8-continued

| Ex | Structure | Dat |
|---|---|---|
| 23 | 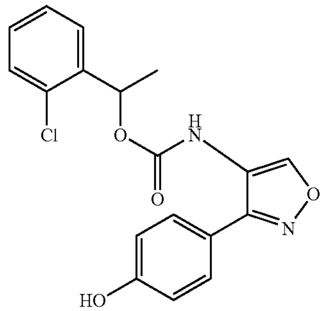 | ¹H-NMR(300 MHz, CDCl₃) δ = 1.54(3H, d, J=6.3 Hz), 2.67-3.07(2H, m), 4.43-4.60(1H, m), 6.12-6.25(1H, m), 6.78-6.88(1H, m), 7.15-7.67(8H, m), 8.78-8.88(1H, m), 8.94(1H, s). MS(ESI) m/z 359(M + H)⁺. |
| 24 | 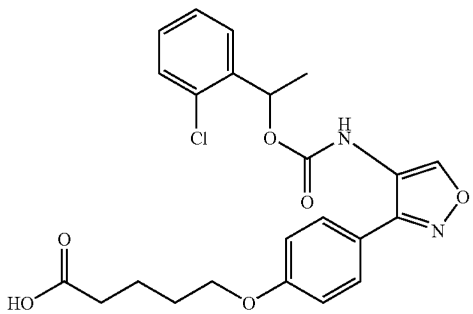 | ¹H-NMR(300 MHz, CDCl₃) δ = 1.58(3H, d, J=6.3 Hz), 1.77-1.95(4H, m), 2.43-2.52(2H, m), 4.02-4.10(2H, m), 6.24(1H, q, J=6.3 Hz), 6.32-6.42(1H, m), 6.95-7.56(8H, m), 8.83-8.92(1H, m). MS(ESI) m/z 459(M + H)⁺. |

TABLE 9

| Ex | Structure | Dat |
|---|---|---|
| 25 | 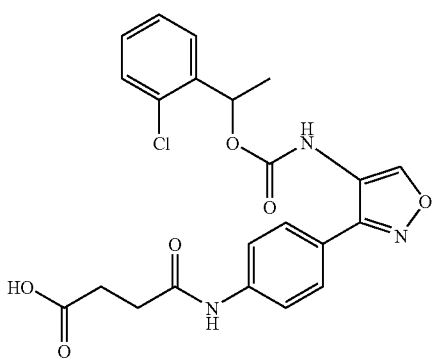 | ¹H-NMR(300 MHz, DMS0-d₆) δ = 1.40-1.48(3H, m), 2.47-2.60(4H, m), 5.88-5.97(1H, m), 7.20-7.80(8H, m), 9.00(1H, s), 9.24(1H, brs), 10.12(1H, s). MS(ESI) m/z 458(M + H)⁺. |
| 26 | 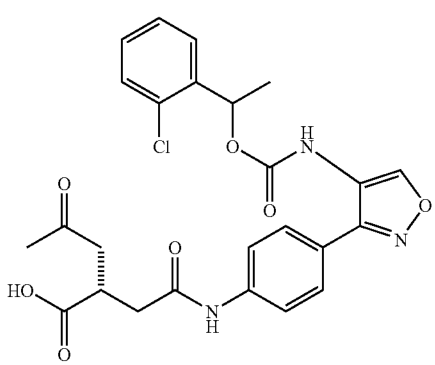 | ¹H-NMR(300 MHz, DMSO-d₆) δ = 1.42-1.55(3H, m), 2.04(3H, s), 2.64–2.94(2H, m), 5.25–5.38(1H, m), 5.90–6.05(1H, m), 7.07–7.75(8H, m), 9.06(1H, s), 9.25–9.38(1H, m), 10.32(1H, s). MS(ESI) m/z 516(M + H)⁺. |

TABLE 9-continued
| Ex | Structure | Dat |
|---|---|---|
| 27 | 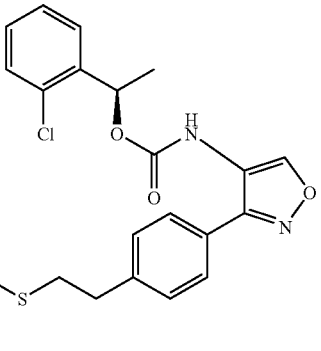 | $^1$H-NMR(300 MHz, CDCl$_3$) δ = 1.55(3H, d, J=6.0 Hz), 2.95(4H, s), 3.25(2H, s), 6.21(1H, q, J=6.0 Hz), 6.67(1H, brs), 7.15–7.56(8H, m), 8.44(1H, brs), 8.86(1H, s). MS(ESI) m/z 461(M + H)$^+$. [α]$_D$ = −37.1° (c = 2.15, MeOH) |
| 28 | 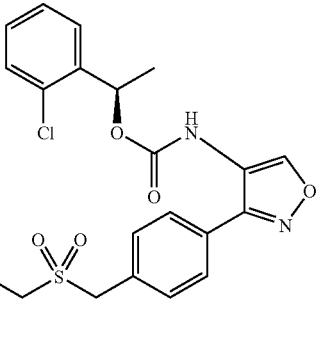 | $^1$H-NMR(300 MHz, CD$_3$OD) δ = 1.58(3H, d, J=6.6 Hz), 2.80(2H, t, J=7.5 Hz), 3.38(2H, t, J=7.5 Hz), 4.52(2H, s), 6.16(1H, q, J=6.6 Hz), 7.22–7.75(8H, m), 8.87(1H, s). MS(ESI) m/z 493(M + H)$^+$. |
| 29 | 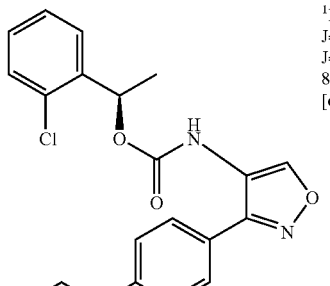 | $^1$H-NMR(300 MHz, CDCl$_3$) δ = 1.59(3H, d, J=6.6 Hz), 2.66–3.01(8H, m), 6.24(1H, q, J=6.6 Hz), 6.53(1H, brs), 7.20–7.59(8H, m), 8.89(1H, s). MS(ESI) m/z 475(M + H)$^+$. [α]$_D$ = −42.7° (c = 1.02, MeOH) |
TABLE 10
| Ex | Structure | Dat |
|---|---|---|
| 30 | 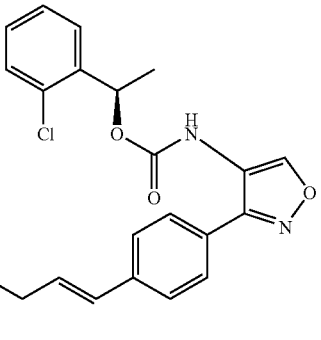 | $^1$H-NMR(300 MHz, CDCl$_3$) δ = 1.58(3H, d, J=6.3 Hz), 2.58(4H, s), 6.18-6.58(4H, m), 7.18-7.70(8H, m), 8.89(1H, s). MS(ESI) m/z 441(M + H)$^+$. |

TABLE 10-continued

| Ex | Structure | Dat |
|---|---|---|
| 31 | 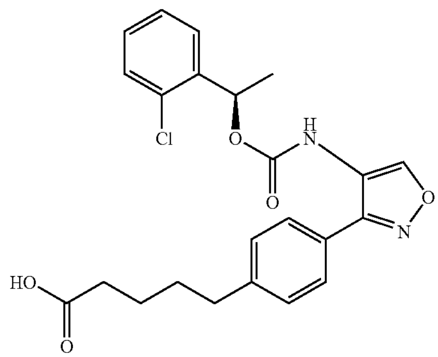 | ¹H-NMR(300 MHz, CDCl₃) δ = 1.58(3H, d, J=6.9 Hz), 1.73(4H, m, 2.41(2H, m), 2.73(2H, m), 6.24(1H, q, J=6.6 Hz), 6.41(1H, bs), 7.15-7.60(8H, m), 8.89(1H, s). MS(ESI) m/z 443(M + H)⁺. |
| 32 | 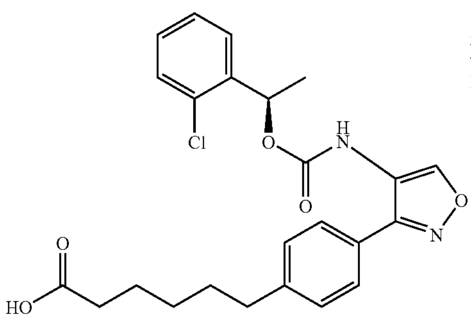 | ¹H-NMR(300 MHz, CDCl₃) δ = 1.00-1.78(9H, m), 2.34(2H, m), 2.69(2H, t, J=7.5 Hz), 6.24(1H, t, J=6.3 Hz), 7.20-7.56(8H, m), 8.89(1H, s). MS(ESI) m/z 457(M + H)⁺. |
| 33 | 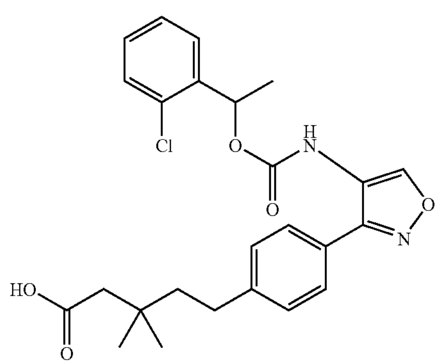 | ¹H-NMR(300 MHz, DMSO-d₆) δ = 1.03(6H, s), 1.40-1.62(5H, m), 2.18(2H, s), 2.59(2H, m), 5.95(1H, m), 7.22-7.62(8H, m), 9.05(1H, s), 9.30(1H, bs). MS(ESI) m/z 471 (M + H)⁺. |
| 34 | 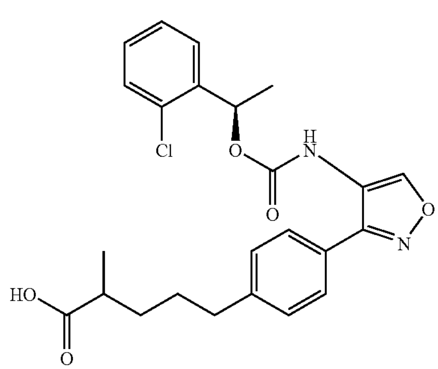 | ¹H-NMR(300 MHz, CDCl₃) δ = 0.853(2H, m), 1.19(3H, d, J=6.9 Hz), 1.57(3H, d, J=6.3 Hz), 1.72(2H, m), 2.50(1H, q, J=6.9 Hz), 2.69(2H, t, J=6.9 Hz), 6.23(1H, q, J=6.3 Hz), 6.46(1H, s), 6.89-7.56(8H, m), 8.88(1H, s). MS(ESI) m/z 457(M + H)⁺. |

TABLE 11

| Compound No. | | IC$_{50}$ (nM) |
|---|---|---|
| Compounds described in WO 01/60819 | Example 115 | 836 |
| | Example 126 | 161 |
| Compounds of the present invention | Compound 2 | 51 |
| | Compound 3 | 22 |
| | Compound 4 | 65 |
| | Compound 5 | 74 |
| | Compound 6 | 22 |
| | Compound 7 | 59 |
| | Compound 8 | 29 |
| | Compound 9 | 26 |
| | Compound 10 | 56 |
| | Compound 11 | 115 |
| | Compound 12 | 68 |
| | Compound 13 | 104 |
| | Compound 14 | 146 |
| | Compound 15 | 44 |
| | Compound 16 | 32 |
| | Compound 17 | 62 |
| | Compound 18 | 81 |
| | Compound 19 | 47 |
| | Compound 20 | 83 |
| | Compound 21 | 84 |
| | Compound 22 | 140 |
| | Compound 23 | 116 |
| | Compound 24 | 131 |
| | Compound 25 | 73 |
| | Compound 26 | 141 |
| | Compound 27 | 19 |
| | Compound 28 | 36 |
| | Compound 29 | 29 |
| | Compound 30 | 107 |
| | Compound 31 | 76 |
| | Compound 32 | 114 |
| | Compound 33 | 119 |
| | Compound 34 | 102 |

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

What is claimed is:

1. An azole compound represented by formula I:

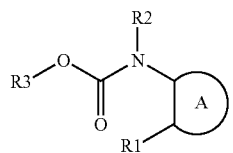

formula I wherein
ring A is

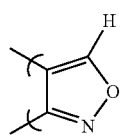

R1 is a phenyl group substituted with a group represented by formula III:

Z—Y—X—  formula III wherein
X is a methylene group or an ethylene group,
Y is a sulfur atom, a sulfinyl group, a sulfonyl group, an oxygen atom, a substituted or unsubstituted amino group, or a methylene group, and
Z is a substituted or unsubstituted lower alkyl group, a substituted or unsubstituted lower alkenyl group, a substituted or unsubstituted alkanoyl group, a substituted or unsubstituted triazolyl group, or a substituted or unsubstituted tetrazolyl group,
wherein the substituent of the group for Z is a carboxyl group, an alkoxycarbonyl group, a furyl group, a phenyl group, a hydroxyl group, a carbamoyl group, a carbamoyl group substituted by a lower alkyl group, a carbamoyl group substituted by a carboxy lower alkyl group, a carbamoyl group substituted by a lower alkyl group substituted by a furyl group, an amino group optionally substituted by an amino-protecting group, a sulfonic acid group, a pyrrolylcarbonyl group, a pyridyl group, or a halogen atom, and the group for Z optionally has the same or different multiple substituents selected from said substituents;
R2 is a hydrogen atom;
R3 is a group represented by the following formula II:

formula II wherein
R4 is chlorophenyl group, a bromophenyl group, a chlorocyclopentenyl group, or a chlorocyclohexenyl group;
R5 is a methyl group; and
R6 is a hydrogen atom,
or a pharmaceutically acceptable salt thereof.

2. An azole compound or pharmaceutically acceptable salt of claim 1, wherein
Y is a sulfur atom, a sulfonyl group, a methylene group, or an oxygen atom;
Z is a substituted methyl group, a substituted ethyl group, or a substituted propyl group,
wherein the substituent of the group for Z is a carboxyl group, an alkoxycarbonyl group, an acetylamino group, a sulfonic acid group, and a hydroxyl group, and the group for Z optionally has multiple substituents selected from said substituents.

3. A pharmaceutical composition, comprising a compound or pharmaceutically acceptable salt according to claim 1 and a pharmaceutically acceptable carrier.

4. A pharmaceutical composition, comprising a compound or pharmaceutically acceptable salt according to claim 2 and a pharmaceutically acceptable carrier.

* * * * *